United States Patent
Meyer et al.

(10) Patent No.: US 12,404,523 B2
(45) Date of Patent: Sep. 2, 2025

(54) ADENO-ASSOCIATED VIRUS DELIVERY OF CLN3 POLYNUCLEOTIDE

(71) Applicants: RESEARCH INSTITUTE AT NATIONWIDE CHILDREN'S HOSPITAL, Columbus, OH (US); OHIO STATE INNOVATION FOUNDATION, Columbus, OH (US)

(72) Inventors: Kathrin Meyer, Columbus, OH (US); Brian K. Kaspar, Columbus, OH (US); Kevin Foust, Columbus, OH (US)

(73) Assignees: RESEARCH INSTITUTE AT NATIONWIDE CHILDREN'S HOSPITAL, Columbus, OH (US); OHIO STATE INNOVATION FOUNDATION, Columbus, OH (US)

( * ) Notice: Subject to any disclaimer, the term of this patent is extended or adjusted under 35 U.S.C. 154(b) by 1062 days.

(21) Appl. No.: 17/427,010

(22) PCT Filed: Feb. 4, 2020

(86) PCT No.: PCT/US2020/016542
§ 371 (c)(1),
(2) Date: Jul. 29, 2021

(87) PCT Pub. No.: WO2020/163300
PCT Pub. Date: Aug. 13, 2020

(65) Prior Publication Data
US 2022/0127641 A1 Apr. 28, 2022

Related U.S. Application Data

(60) Provisional application No. 62/800,911, filed on Feb. 4, 2019.

(51) Int. Cl.
| | | |
|---|---|---|
| *C12N 15/86* | (2006.01) | |
| *A61P 3/00* | (2006.01) | |
| *A61P 25/00* | (2006.01) | |
| *C07K 14/47* | (2006.01) | |
| *C12N 7/00* | (2006.01) | |

(52) U.S. Cl.
CPC .............. *C12N 15/86* (2013.01); *A61P 3/00* (2018.01); *A61P 25/00* (2018.01); *C07K 14/47* (2013.01); *C12N 7/00* (2013.01); *C12N 2750/14143* (2013.01); *C12N 2750/14171* (2013.01)

(58) Field of Classification Search
CPC ........ C12N 15/86; C12N 7/00; C12N 2750/14143; C12N 2750/14171; A61P 3/00; A61P 25/00; C07K 14/47; A61K 48/00
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 9,434,928 B2 | 9/2016 | Mendell et al. |
| 10,876,134 B2 * | 12/2020 | Kielian ................... A61P 25/00 |
| 2005/0053922 A1 | 3/2005 | Schaffer et al. |
| 2009/0202490 A1 | 8/2009 | Schaffer et al. |
| 2020/0179467 A1 * | 6/2020 | Kaspar ................... A61P 25/00 |

FOREIGN PATENT DOCUMENTS

| | | | |
|---|---|---|---|
| WO | 95/13365 A1 | 5/1995 | |
| WO | 95/13392 A1 | 5/1995 | |
| WO | 96/17947 A1 | 6/1996 | |
| WO | 97/06243 A1 | 2/1997 | |
| WO | 97/08298 A1 | 3/1997 | |
| WO | 97/09441 A2 | 3/1997 | |
| WO | 97/21825 A1 | 6/1997 | |
| WO | 98/09657 A2 | 3/1998 | |
| WO | 99/11764 A2 | 3/1999 | |
| WO | 2014/022582 A1 | 2/2014 | |
| WO | WO-2016100575 A1 * | 6/2016 | ............. A61K 48/00 |
| WO | 2018/094251 A1 | 5/2018 | |

OTHER PUBLICATIONS

McCormack, P.L. "Iobitridol. A Review of Its Use as a Contrast Medium in Diagnostic Imaging." Clinical Drug Investigation, vol. 33 (2013), pp. 155-166 (Year: 2013).*
Castle, M.J. et al. "Physical positioning markedly enhances brain transduction after intrathecal AAV9 infusion." Science Advances, vol. 4 (2018), p. 2aau9859 (Year: 2018).*
PDF of Sequence listings from PCT-US15-66206 (downloaded from Espace.net/Global Dossier . (Year: 2016).*
PDF of NM_000086.2-*Homo sapiens* CLN3 mRNA (Year: 2006).*
Bosch et al., Self-Complementary AAV9 Gene Delivery Partially Corrects Pathology Associated with Juvenile Neuronal Ceroid Lipofuscinosis (CLN3), J. Neurosci., 36(37):9669-9682 (2016).
Cain et al., Gene Therapy Corrects Brain and Behavioral Pathologies in CLN6-Batten Disease, Mol. Ther., 27(10):1836-1847 (2019).
Carter, Adeno-associated virus vectors, Current Opinions in Biotechnology, 3(5):533-539 (1992).
Choudhury et al., In Vivo Selection Yields AAV-B1 Capsid for Central Nervous System and Muscle Gene Therapy, Mol. Ther., 24(7):1247-1257 (2016).

(Continued)

*Primary Examiner* — Neil P Hammell
*Assistant Examiner* — Alexandra Geraldine Dace Denito
(74) *Attorney, Agent, or Firm* — MARSHALL, GERSTEIN & BORUN LLP

(57) ABSTRACT

The present disclosure relates to recombinant adeno-associated virus (rAAV) delivery of a ceroid lipofuscinosis neuronal 3 (CLN3) polynucleotide. The disclosure provides rAAV and methods of using the rAAV for CLN3 gene therapy of the neuronal ceroid lipofuscinosis or CLN3-Batten Disease.

26 Claims, 38 Drawing Sheets

Specification includes a Sequence Listing.

(56) References Cited

OTHER PUBLICATIONS

Clark et al., A stable cell line carrying adenovirus-inducible rep and cap genes allows for infectivity titration of adeno-associated virus vectors, Gene. Therapy, 3(12):1124-1132 (1996).
Clark et al., Highly purified recombinant adeno-associated virus vectors are biologically active and free of detectable helper and wild-type viruses, Hum. Gene. Ther., 10(6):1031-1039 (1999).
Cotman et al., Cln3(Deltaex7/8) knock-in mice with the common JNCL mutation exhibit progressive neurologic disease that begins before birth, Hum. Mol. Genet., 11(22):2709-2721 (2002).
Cotman et al., The juvenile Batten disease protein, CLN3, and its role in regulating anterograde and retrograde post-Golgi trafficking, Clin. Lipidol., 7(1):79-91 (2012).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Gao et al., Clades of Adeno-associated Viruses Are Widely Disseminated in Human Tissues, J. Virol., 78:6381-6388 (2004).
Garg et al., Systemic delivery of MeCP2 rescues behavioral and cellular deficits in female mouse models of Rett syndrome, J. Neurosci. 33:13612-13620 (2013).
Giles et al., Deamidation of Amino Acids on the Surface of Adeno-Associated Virus Capsids Leads to Charge Heterogeneity and Altered Vector Function, Molecular Therapy, 26(12):2848-2862 (2018).
Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).
International Application No. PCT/US20/16542, International Preliminary Report on Patentability, mailed Aug. 19, 2021.
International Application No. PCT/US20/16542, International Search Report and Written Opinion, mailed May 27, 2020.
Kitzmüller et al., A function retained by the common mutant CLN3 protein is responsible for the late onset of juvenile neuronal ceroid lipofuscinosis, Human Molecular Genetics, 17(2):303-312 (2008).
Laughlin et al., Cloning of infectious adeno-associated virus genomes in bacterial plasmids, Gene., 23(1):65-73 (1983).
Lebkowski et al., 1988 Mol. Cell. Biol., 7:349 (1988).
Lerner et al., Isolation of a Novel Gene Underlying Batten Disease, CLN3, Cell. 82(6):949-57 (1995).
Marshall et al., A clinical rating scale for Batten disease: reliable and relevant for clinical trials, Neurology, 65(2):275-279 (2005).
Marsic et al., Vector Design Tour de Force: Integrating Combinatorial and Rational Approaches to Derive Novel Adeno-associated Virus Variants, Molecular Therapy, 22(11):1900-1909 (2014).
McCarty et al., Self-complementary recombinant adeno-associated virus (scAAV) vectors promote efficient transduction independently of DNA synthesis, Gene. Therapy, 8(16):1248-1254 (2001).
McLaughlin et al., Adeno-associated virus general transduction vectors: analysis of proviral structures, J. Virol., 62(6):1963-73 (1988).
Mole et al., Genetics of the neuronal ceroid lipofuscinoses (Batten disease), Biochim Biophys Acta—Mol Basis Dis., 1852(10):2237-2241 (2015).
Mole et al., New mutations in the neuronal ceroid lipofuscinosis genes, Eur. J. Paediatr. Neurol., 5:7-10 (2001).
Morgan et al., A murine model of variant late infantile ceroid lipofuscinosis recapitulates behavioral and pathological phenotypes of human disease, PLoS One, 8(11):e78694 (2013).
Mori et al., Two novel adeno-associated viruses from cynomolgus monkey: pseudotyping characterization of capsid protein, Virology, 330(2):375-383 (2004).
Munroe et al., Spectrum of mutations in the Batten disease gene, CLN3, Am. J. Hum. Genet., 61(2):310-316 (1997).
Muzyczka, Use of Adeno-Associated Virus as a General Transduction Vector for Mammalian Cells, Current Topics in Microbiology and Immunology, 158:97-129 (1992).
Osorio et al., Neurodevelopmental delay in the Cln3Deltaex7/8 mouse model for Batten disease, Genes. Brain Behav., 8(3):337-345 (2009).
Palmer et al., Mitochondrial ATP synthase subunit c storage in the ceroid-lipofuscinoses (Batten disease), Am. J. Med. Genet., 42(4):561-567 (1992).
Paul et al., Increased Viral Titer Through Concentration of Viral Harvests from Retroviral Packaging Lines, Human Gene Therapy, 4(5):609-615 (1993).
Perrin et al., An experimental rabies vaccine produced with a new BHK-21 suspension cell culture process: use of serum-free medium and perfusion-reactor system, Vaccine, 13(13):1244-1250 (1995).
Pontikis et al., Thalamocortical neuron loss and localized astrocytosis in the Cln3Deltaex7/8 knock-in mouse model of Batten disease, Neurobiol. Dis., 20(3):823-836 (2005).
Sambrook et al., Molecular Cloning: A Laboratory Manual, 2nd Ed., Cold Spring Harbor Laboratory, (1989).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Schenpp et al., Highly purified recombinant adeno-associated virus vectors. Preparation and quantitation, Methods Mol. Med., 69:427-443 (2002).
Seehafer et al., Immunosuppression alters disease severity in juvenile Batten disease mice, J. Neuroimmunol., 230(1-2):169-172 (2011).
Seehafer et al., You say lipofuscin, we say ceroid: defining autofluorescent storage material, Neurobiol. Aging., 27:576-588 (2006).
Seigel et al., Retinal pathology and function in a Cln3 knockout mouse model of juvenile Neuronal Ceroid Lipofuscinosis (batten disease), Mol Cell Neurosci., 19(4):515-27 (2002).
Senapathy et al., Molecular cloning of adeno-associated virus variant genomes and generation of infectious virus by recombination in mammalian cells, J. Biol. Chem., 259:4661-4666 (1984).
Sondhi et al., Partial Correction of the CNS Lysosomal Storage Defect in a Mouse Model of Juvenile Neuronal Ceroid Lipofuscinosis by Neonatal CNS Administration of an Adeno-Associated Virus Serotype rh.10 Vector Expressing the Human CLN3 Gene, Human Gene Therapy, 25(3):223-239 (2014).
Srivastava et al., Nucleotide sequence and organization of the adeno-associated virus 2 genome, J. Virol., 45(2):555-564 (1983).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
GenBank Accession No. AAC05337, CLN3 [*Homo sapiens*], dated Oct. 30, 2002.

\* cited by examiner

Figure 14 (SEQ ID NO: 4)
CLN3 - scAAV9.P546.CLN3

*AAV2 ITR*—P546—SV40intron—Human CLN3 cDNA—BGHpolyA—*AAV2 ITR*

*CTGCGCGCTCGCTCGCTCACTGAGGCCGCCCGGGCAAAGCCCGGGCGTCGGGCGACCTTTGGTCGCCCGGCCT*
*CAGTGAGCGAGCGAGCGCGCAGAGAGGGAGTGG*AATTCAATTCACGCGCCGGTACCGAATTCACGCGT<u>GAAC</u>
<u>AACGCCAGGCTCCTCAACAGGCAACTTTGCTACTTCTACAGAAAATGATAATAAAGAAATGCTGGTGAAGTCA</u>
<u>AATGCTTATCACAATGGTGAACTACTCAGCAGGGAGGCTCTAATAGGCGCCAAGAGCCTAGACTTCCTTAAGC</u>
<u>GCCAGAGTCCACAAGGGCCCAGTTAATCCTCAACATTCAAATGCTGCCCACAAAACCAGCCCCTCTGTGCCCTA</u>
<u>GCCGCCTCTTTTTTCCAAGTGACAGTAGAACTCCACCAATCCGCAGCTGAATGGGGTCCGCCTCTTTTCCCTGCC</u>
<u>TAAACAGACAGGAACTCCTGCCAATTGAGGGCGTCACCGCTAAGGCTCCGCCCCAGCCTGGGCTCCACAACCA</u>
<u>ATGAAGGGTAATCTCGACAAAGAGCAAGGGGTGGGGCGCGGGCGCGCAGGTGCAGCAGCACACAGGCTGGT</u>
<u>CGGGAGGGCGGGGCGCGACGTCTGCCGTGCGGGGTCCCGGCATCGGTTGCGCGCGCGCTCCCTCCTCTCGGA</u>
<u>GAGAGGGCTGTGGTAAAACCCGTCCGGAAAACGCGTCGAAGGGCGAATTCTGCAGATAACT</u><u>GGTAAGTTTAG</u>
<u>TCTTTTTTGTCTTTTATTTCAGGTCCCGGATCCGGTGGTGGTGCAAATCAAAGAACTGCTCCTCAGTCGATGTTG</u>
<u>CCTTTACTTCTAGG</u>CCTGTACGAAGTGTTACTACCGGATGGGAGGCTGTGCAGGCTCGCGGCGGCGCTTTT
CGGATTCCGAGGGGGAGGAGACCGTCCCGGAGCCCCGGCTCCCTCTGTTGGACCATCAGGGCGCGCATTGG
AAGAACGCGGTGGGCTTCTGGCTGCTGGGCCTTTGCAACAACTTCTCTTATGTGGTGATGCTGAGTGCCGCC
ACGACATCCTTAGCCACAAGAGGACATCGGGAAACCAGAGCCATGTGGACCCAGGCCCAACGCCGATCCCC
ACAACAGCTCATCACGATTTGACTGCAACTCTGTCTCTACGGCTGCTGTGCTCCTGGCGGACATCCTCCCCACA
CTCGTCATCAAATTGTTGGCTCCTCTTGGCCTTCACCTGCTGCCCTACAGCCCCGGGTTCTCGTCAGTGGGAT
TTGTGCTGCTGGAAGCTTCGTCCTGGTTGCCTTTTCTCATTCTGTGGGGACCAGCCTGTGTGGTGTGGTCTTCG
CTAGCATCTCATCAGGCCTTGGGGAGGTCACCTTCCTCTCCCTCACTGCCTTCTACCCCAGGGCCGTGATCTCC
TGGTGGTCCTCAGGGACTGGGGGAGCTGGGCTGCTGGGGGCCCTGTCCTACCTGGGCCTCACCCAGGCCGG
CCTCTCCCCTCAGCAGACCCTGCTGTCCATGCTGGGTATCCCTGCCCTGCTGCTGGCCAGCTATTTCTTGTTGCT
CACATCTCCTGAGGCCCAGGACCCTGGAGGGGAAGAAGAAGCAGAGAGCGCAGCCCGGCAGCCCCTCATAA
GAACCGAGGCCCCGGAGTCGAAGCCAGGCTCCAGCTCCAGCCTCTCCCTTCGGGAAAGGTGGACAGTGTTCA
AGGGTCTGCTGTGGTACATTGTTCCCTTGGTCGTAGTTTACTTTGCCGAGTATTTCATTAACCAGGGACTTTTT
GAACTCCTCTTTTTCTGGAACACTTCCCTGAGTCACGCTCAGCAATACCGCTGGTACCAGATGCTGTACCAGG
CTGGCGTCTTTGCCTCCCGCTCTTCTCTCCGCTGCTGTCGCATCCGTTTCACCTGGGCCCTGGCCCTGCTGCAGT
GCCTCAACCTGGTGTTCCTGCTGGCAGACGTGTGGTTCGGCTTTCTGCCAAGCATCTACCTCGTCTTCCTGATC
ATTCTGTATGAGGGGCTCCTGGGAGGCGCAGCCTACGTGAACACCTTCCACAACATCGCCCTGGAGACCAGT
GATGAGCACCGGGAGTTTGCAATGGCGGCCACCTGCATCTCTGACACACTGGGGATCTCCCTGTCGGGCTC
CTGGCTTTGCCTCTGCATGACTTCCTCTGCCAGCTCTCCTGACCTGCAGG<u>CCTCGACTGTGCCTTCTAGTTGCCA</u>
<u>GCCATCTGTTGTTTGCCCCTCCCCCGTGCCTTCCTTGACCCTGGAAGGTGCCACTCCCACTGTCCTTTCCTAATAA</u>
<u>AATGAGGAAATTGCATCGCATTGTCTGAGTAGGTGTCATTCTATTCGCATGCTGGGGAGAGATCGATCTG</u>*AGG*
*AACCCCTAGTGATGGAGTTGGCCACTCCCTCTCTGCGCGCTCGCTCGCTCACTGAGGCCGGGCGACCAAAGGTC*
*GCCCGACGCCCGGGCTTTGCCCGGGCGGCCTCAGTGAGCGAGCGAGCGCGCAGAGAGGGAGTGG*

Figure 15 (SEQ ID NO: 5)

Complete AAV.546.CLN3
```
GCCCAATACGCAAACCGCCTCTCCCCGCGCGTTGGCCGATTCATTAATGCAGCTGGCGTAATAGCGAAGAGGCCC
GCACCGATCGCCCTTCCCAACAGTTGCGCAGCCTGAATGGCGAATGGCGATTCCGTTGCAATGGCTGGCGGTAAT
ATTGTTCTGGATATTACCAGCAAGGCCGATAGTTTGAGTTCTTCTACTCAGGCAAGTGATGTTATTACTAATCAAAG
AAGTATTGCGACAACGGTTAATTTGCGTGATGGACAGACTCTTTTACTCGGTGGCCTCACTGATTATAAAAACACTT
CTCAGGATTCTGGCGTACCGTTCCTGTCTAAAATCCCTTTAATCGGCCTCCTGTTTAGCTCCCGCTCTGATTCTAACG
AGGAAAGCACGTTATACGTGCTCGTCAAAGCAACCATAGTACGCGCCCTGTAGCGGCGCATTAAGCGCGGCGGGT
GTGGTGGTTACGCGCAGCGTGACCGCTACACTTGCCAGCGCCCTAGCGCCCGCTCCTTTCGCTTTCTTCCCTTCCTT
TCTCGCCACGTTCGCCGGCTTTCCCCGTCAAGCTCTAAATCGGGGGCTCCCTTTAGGGTTCCGATTTAGTGCTTTAC
GGCACCTCGACCCCAAAAAACTTGATTAGGGTGATGGTTCACGTAGTGGGCCATCGCCCTGATAGACGGTTTTCG
CCCTTTGACGTTGGAGTCCACGTTCTTTAATAGTGGACTCTTGTTCCAAACTGGAACAACACTCAACCCTATCTCGG
TCTATTCTTTTGATTTATAAGGGATTTTGCCGATTTCGGCCTATTGGTTAAAAAATGAGCTGATTTAACAAAAATTTA
ACGCGAATTTTAACAAAATATTAACGCTTACAATTTAAATATTTGCTTATACAATCTTCCTGTTTTTGGGGCTTTTCT
GATTATCAACCGGGGTACATATGATTGACATGCTAGTTTTACGATTACCGTTCATCGCCCTGCGCGCTCGCTCGCTC
ACTGAGGCCGCCCGGGCAAAGCCCGGGCGTCGGGCGACCTTTGGTCGCCCGGCCTCAGTGAGCGAGCGAGCGCG
CAGAGAGGGAGTGGAATTCAATTCACGCGCCGGTACCGAATTCACGCGTGAACAACGCCAGGCTCCTCAACAGGC
AACTTTGCTACTTCTACAGAAAATGATAATAAAGAAATGCTGGTGAAGTCAAATGCTTATCACAATGGTGAACTAC
TCAGCAGGGAGGCTCTAATAGGCGCCAAGAGCCTAGACTTCCTTAAGCGCCAGAGTCCACAAGGGCCCAGTTAAT
CCTCAACATTCAAATGCTGCCCACAAAACCAGCCCCTCTGTGCCCTAGCCGCCTCTTTTTTCCAAGTGACAGTAGAA
CTCCACCAATCCGCAGCTGAATGGGGTCCGCCTCTTTTCCCTGCCTAAACAGACAGGAACTCCTGCCAATTGAGGG
CGTCACCGCTAAGGCTCCGCCCCAGCCTGGGCTCCACAACCAATGAAGGGTAATCTCGACAAAGAGCAAGGGGTG
GGGCGCGGGCGCGCAGGTGCAGCAGCACACAGGCTGGTCGGGAGGGCGGGGCGCGACGTCTGCCGTGCGGGG
TCCCGGCATCGGTTGCGCGCGCGCTCCCTCCTCTCGGAGAGAGGGCTGTGGTAAAACCCGTCCGGAAAACGCGTC
GAAGGGCGAATTCTGCAGATAACTGGTAAGTTTAGTCTTTTTTGTCTTTTATTTCAGGTCCCGGATCCGGTGGTGGT
GCAAATCAAAGAACTGCTCCTCAGTCGATGTTGCCTTTACTTCTAGGCCTGTACGGAAGTGTTACTACCGGTATGG
GAGGCTGTGCAGGCTCGCGGCGGCGCTTTTCGGATTCCGAGGGGGAGGAGACCGTCCCGGAGCCCCGGCTCCCT
CTGTTGGACCATCAGGGCGCGCATTGGAAGAACGCGGTGGGCTTCTGGCTGCTGGGCCTTTGCAACAACTTCTCTT
ATGTGGTGATGCTGAGTGCCGCCCACGACATCCTTAGCCACAAGAGGACATCGGGAAACCAGAGCCATGTGGACC
CAGGCCCAACGCCGATCCCCCACAACAGCTCATCACGATTTGACTGCAACTCTGTCTCTACGGCTGCTGTGCTCCTG
GCGGACATCCTCCCCACACTCGTCATCAAATTGTTGGCTCCTCTTGGCCTTCACCTGCTGCCCTACAGCCCCCGGGT
TCTCGTCAGTGGGATTTGTGCTGCTGGAAGCTTCGTCCTGGTTGCCTTTTCTCATTCTGTGGGGACCAGCCTGTGTG
GTGTGGTCTTCGCTAGCATCTCATCAGGCCTTGGGGAGGTCACCTTCCTCTCCCTCACTGCCTTCTACCCCAGGGCC
GTGATCTCCTGGTGGTCCTCAGGGACTGGGGGAGCTGGGCTGCTGGGGGCCCTGTCCTACCTGGGCCTCACCCAG
GCCGGCCTCTCCCCTCAGCAGACCCTGCTGTCCATGCTGGGTATCCCTGCCCTGCTGCTGGCCAGCTATTTCTTGTT
GCTCACATCTCCTGAGGCCCAGGACCCTGGAGGGGAAGAAGAAGCAGAGAGCGCAGCCCGGCAGCCCCTCATAA
GAACCGAGGCCCCGGAGTCGAAGCCAGGCTCCAGCTCCAGCCTCTCCCTTCGGGAAAGGTGGACAGTGTTCAAG
GGTCTGCTGTGGTACATTGTTCCCTTGGTCGTAGTTTACTTTGCCGAGTATTTCATTAACCAGGGACTTTTTGAACTC
CTCTTTTTCTGGAACACTTCCCTGAGTCACGCTCAGCAATACCGCTGGTACCAGATGCTGTACCAGGCTGGCGTCTT
TGCCTCCCGCTCTTCTCTCCGCTGCTGTCGCATCCGTTTCACCTGGGCCCTGGCCCTGCTGCAGTGCCTCAACCTGG
TGTTCCTGCTGGCAGACGTGTGGTTCGGCTTTCTGCCAAGCATCTACCTCGTCTTCCTGATCATTCTGTATGAGGGG
CTCCTGGGAGGCGCAGCCTACGTGAACACCTTCCACAACATCGCCCTGGAGACCAGTGATGAGCACCGGGAGTTT
GCAATGGCGGCCACCTGCATCTCTGACACACTGGGGATCTCCCTGTCGGGGCTCCTGGCTTTGCCTCTGCATGACT\
```

Figure 15 Cont.

TCCTCTGCCAGCTCTCCTGACCTGCAGGCCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGAAATTGCATCGCATTGTCT
GAGTAGGTGTCATTCTATTCGCATGCTGGGGAGAGATCGATCTGAGGAACCCCTAGTGATGGAGTTGGCCACTCC
CTCTCTGCGCGCTCGCTCGCTCACTGAGGCCGGGCGACCAAAGGTCGCCCGACGCCCGGGCTTTGCCCGGGCGGC
CTCAGTGAGCGAGCGAGCGCGCAGAGAGGGAGTGGCCCCCCCCCCCCCCCCCCGGCGATTCTCTTGTTTGCTCC
AGACTCTCAGGCAATGACCTGATAGCCTTTGTAGAGACCTCTCAAAAATAGCTACCCTCTCCGGCATGAATTTATCA
GCTAGAACGGTTGAATATCATATTGATGGTGATTTGACTGTCTCCGGCCTTTCTCACCCGTTTGAATCTTTACCTACA
CATTACTCAGGCATTGCATTTAAAATATATGAGGGTTCTAAAAATTTTTATCCTTGCGTTGAAATAAAGGCTTCTCC
CGCAAAAGTATTACAGGGTCATAATGTTTTTGGTACAACCGATTTAGCTTTATGCTCTGAGGCTTTATTGCTTAATTT
TGCTAATTCTTTGCCTTGCCTGTATGATTTATTGGATGTTGGAATCGCCTGATGCGGTATTTTCTCCTTACGCATCTG
TGCGGTATTTCACACCGCATATGGTGCACTCTCAGTACAATCTGCTCTGATGCCGCATAGTTAAGCCAGCCCCGAC
ACCCGCCAACACTATGGTGCACTCTCAGTACAATCTGCTCTGATGCCGCATAGTTAAGCCAGCCCCGACACCCGCC
AACACCCGCTGACGCGCCCTGACGGGCTTGTCTGCTCCCGGCATCCGCTTACAGACAAGCTGTGACCGTCTCCGGG
AGCTGCATGTGTCAGAGGTTTTCACCGTCATCACCGAAACGCGCGAGACGAAAGGGCCTCGTGATACGCCTATTTT
TATAGGTTAATGTCATGAGACAATAACCCTGATAAATGCTTCAATAATATTGAAAAAGGAAGAGTATGAGCCATAT
TCAACGGGAAACGTCGAGGCCGCGATTAAATTCCAACATGGATGCTGATTTATATGGGTATAAATGGGCTCGCGA
TAATGTCGGGCAATCAGGTGCGACAATCTATCGCTTGTATGGGAAGCCCGATGCGCCAGAGTTGTTTCTGAAACAT
GGCAAAGGTAGCGTTGCCAATGATGTTACAGATGAGATGGTCAGACTAAACTGGCTGACGGAATTTATGCCACTT
CCGACCATCAAGCATTTTATCCGTACTCCTGATGATGCATGGTTACTCACCACTGCGATCCCCGGAAAAACAGCGTT
CCAGGTATTAGAAGAATATCCTGATTCAGGTGAAAATATTGTTGATGCGCTGGCAGTGTTCCTGCGCCGGTTGCAC
TCGATTCCTGTTTGTAATTGTCCTTTTAACAGCGATCGCGTATTTCGCCTCGCTCAGGCGCAATCACGAATGAATAA
CGGTTTGGTTGATGCGAGTGATTTTGATGACGAGCGTAATGGCTGGCCTGTTGAACAAGTCTGGAAAGAAATGCA
TAAACTTTTGCCATTCTCACCGGATTCAGTCGTCACTCATGGTGATTTCTCACTTGATAACCTTATTTTTGACGAGGG
GAAATTAATAGGTTGTATTGATGTTGGACGAGTCGGAATCGCAGACCGATACCAGGATCTTGCCATCCTATGGAA
CTGCCTCGGTGAGTTTTCTCCTTCATTACAGAAACGGCTTTTTCAAAAATATGGTATTGATAATCCTGATATGAATA
AATTGCAGTTTCATTTGATGCTCGATGAGTTTTTCTAACTGTCAGACCAAGTTTACTCATATATACTTTAGATTGATT
TAAAACTTCATTTTTAATTTAAAAGGATCTAGGTGAAGATCCTTTTTGATAATCTCATGACCAAAATCCCTTAACGTG
AGTTTTCGTTCCACTGAGCGTCAGACCCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTGCCGGATCAAGAGCTACCAACTCTTT
TTCCGAAGGTAACTGGCTTCAGCAGAGCGCAGATACCAAATACTGTTCTTCTAGTGTAGCCGTAGTTAGGCCACCA
CTTCAAGAACTCTGTAGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCTACAGCGTGAGCTATGAGAAAGC
GCCACGCTTCCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACTTGAGCGTCGATT
TTTGTGATGCTCGTCAGGGGGCGGAGCCTATGGAAAAACGCCAGCAACGCGGCCTTTTTACGGTTCCTGGCCTTT
TGCTGGCCTTTTGCTCACATGTTCTTTCCTGCGTTATCCCCTGATTCTGTGGATAACCGTATTACCGCCTTTGAGTGA
GCTGATACCGCTCGCCGCAGCCGAACGACCGAGCGCAGCGAGTCAGTGAGCGAGGAAGCGGAAGAGC

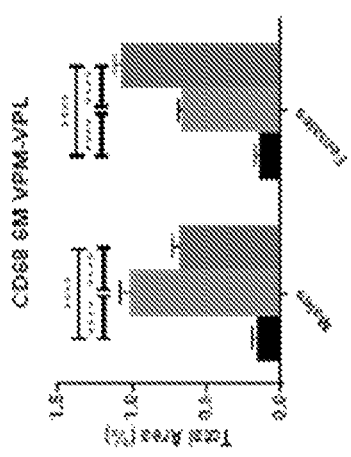
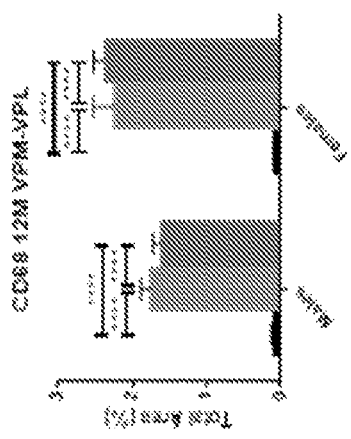
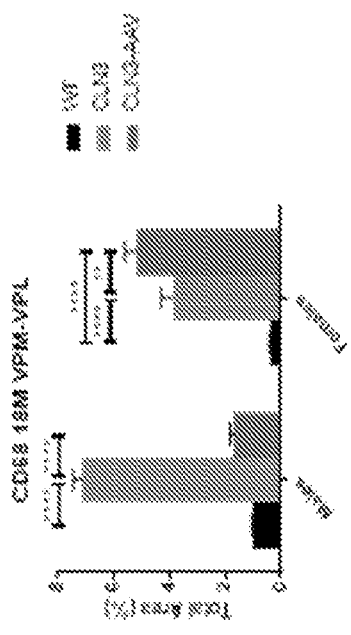
Figure 36
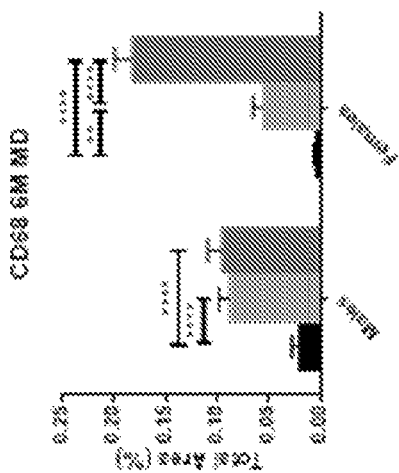
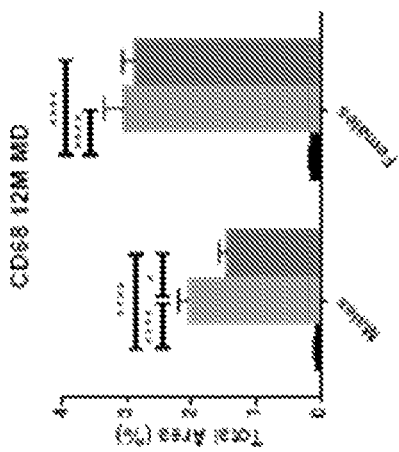
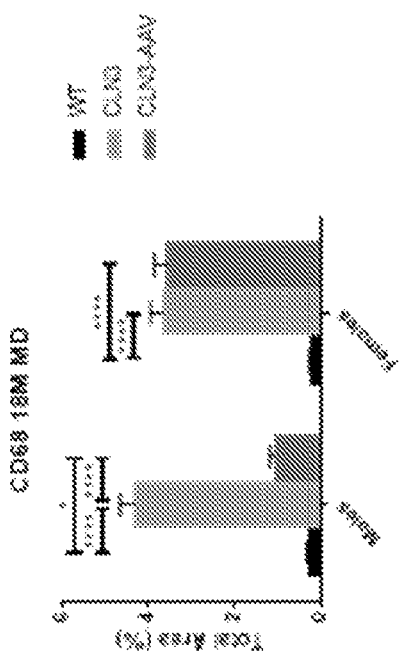
Figure 37

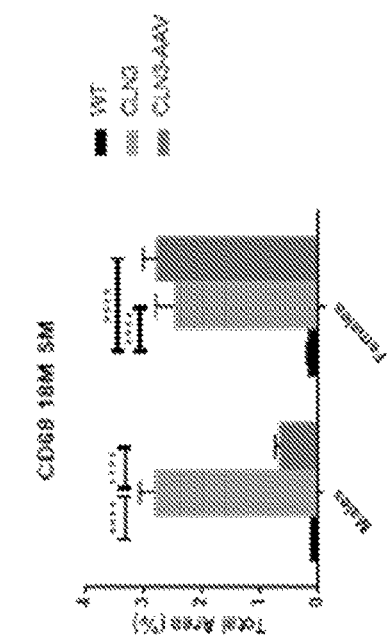
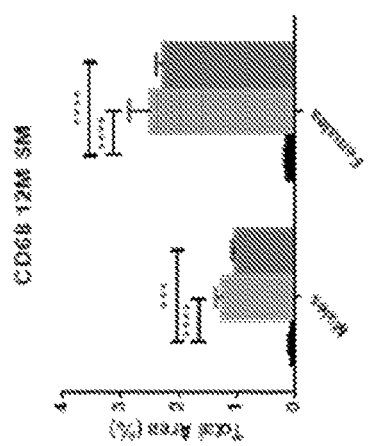
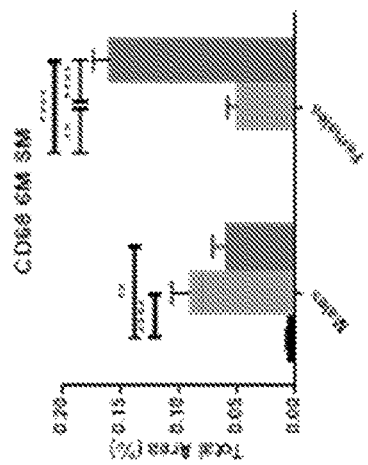
Figure 38

SEQUENCE LISTING

<160> NUMBER OF SEQ ID NOS: 12

<210> SEQ ID NO 1
<211> LENGTH: 438
<212> TYPE: PRT
<213> ORGANISM: Homo sapiens
<220> FEATURE:
<221> NAME/KEY: MISC_FEATURE
<223> OTHER INFORMATION: CLN3

<400> SEQUENCE: 1

Met Gly Gly Cys Ala Gly Ser Arg Arg Phe Ser Asp Ser Glu Gly
1               5                   10                  15

Glu Glu Thr Val Pro Glu Pro Arg Leu Pro Leu Leu Asp His Gln Gly
                20                  25                  30

Ala His Trp Lys Asn Ala Val Gly Phe Trp Leu Leu Gly Leu Cys Asn
            35                  40                  45

Asn Phe Ser Tyr Val Val Met Leu Ser Ala Ala His Asp Ile Leu Ser
    50                  55                  60

His Lys Arg Thr Ser Gly Asn Gln Ser His Val Asp Pro Gly Pro Thr
65                  70                  75                  80

Pro Ile Pro His Asn Ser Ser Arg Phe Asp Cys Asn Ser Val Ser
                85                  90                  95

Thr Ala Ala Val Leu Leu Ala Asp Ile Leu Pro Thr Leu Val Ile Lys
                100                 105                 110

Leu Leu Ala Pro Leu Gly Leu His Leu Leu Pro Tyr Ser Pro Arg Val
            115                 120                 125

Leu Val Ser Gly Ile Cys Ala Ala Gly Ser Phe Val Leu Val Ala Phe
    130                 135                 140

Ser His Ser Val Gly Thr Ser Leu Cys Gly Val Val Phe Ala Ser Ile
145                 150                 155                 160

Ser Ser Gly Leu Gly Glu Val Thr Phe Leu Ser Leu Thr Ala Phe Tyr
                165                 170                 175

Pro Arg Ala Val Ile Ser Trp Trp Ser Ser Gly Thr Gly Ala Gly
            180                 185                 190

Leu Leu Gly Ala Leu Ser Tyr Leu Gly Leu Thr Gln Ala Gly Leu Ser
    195                 200                 205

Pro Gln Gln Thr Leu Leu Ser Met Leu Gly Ile Pro Ala Leu Leu Leu
210                 215                 220

Ala Ser Tyr Phe Leu Leu Leu Thr Ser Pro Glu Ala Gln Asp Pro Gly
225                 230                 235                 240

Gly Glu Glu Glu Ala Glu Ser Ala Ala Arg Gln Pro Leu Ile Arg Thr
                245                 250                 255

Glu Ala Pro Glu Ser Lys Pro Gly Ser Ser Ser Ser Leu Ser Leu Arg
            260                 265                 270

Glu Arg Trp Thr Val Phe Lys Gly Leu Leu Trp Tyr Ile Val Pro Leu
    275                 280                 285

Val Val Val Tyr Phe Ala Glu Tyr Phe Ile Asn Gln Gly Leu Phe Glu
290                 295                 300

Leu Leu Phe Phe Trp Asn Thr Ser Leu Ser His Ala Gln Gln Tyr Arg
305                 310                 315                 320

Trp Tyr Gln Met Leu Tyr Gln Ala Gly Val Phe Ala Ser Arg Ser Ser
                325                 330                 335

Leu Arg Cys Cys Arg Ile Arg Phe Thr Trp Ala Leu Ala Leu Leu Gln
            340                 345                 350

```
                Cys Leu Asn Leu Val Phe Leu Leu Ala Asp Val Trp Phe Gly Phe Leu
                            355                 360                 365

Pro Ser Ile Tyr Leu Val Phe Leu Ile Ile Leu Tyr Glu Gly Leu Leu
                        370                 375                 380

Gly Gly Ala Ala Tyr Val Asn Thr Phe His Asn Ile Ala Leu Glu Thr
                385                 390                 395                 400

Ser Asp Glu His Arg Glu Phe Ala Met Ala Ala Thr Cys Ile Ser Asp
                            405                 410                 415

Thr Leu Gly Ile Ser Leu Ser Gly Leu Leu Ala Leu Pro Leu His Asp
                            420                 425                 430

Phe Leu Cys Gln Leu Ser
                            435

<210> SEQ ID NO 2
<211> LENGTH: 1317
<212> TYPE: DNA
<213> ORGANISM: Homo sapiens
<220> FEATURE:
<221> NAME/KEY: misc_feature
<223> OTHER INFORMATION: CNL3

<400> SEQUENCE: 2
atgggaggct gtgcaggctc gcggcggcgc ttttcggatt ccgaggggga ggagaccgtc        60
ccggagcccc ggctccctct gttggaccat cagggcgcgc attggaagaa cgcggtgggc       120
ttctggctgc tgggcctttg caacaacttc tcttatgtgg tgatgctgag tgccgcccac       180
gacatcctta gccacaagag gacatcggga aaccagagcc atgtggaccc aggcccaacg       240
ccgatccccc acaacagctc atcacgattt gactgcaact ctgtctctac ggctgctgtg       300
ctcctggcgg acatcctccc cacactcgtc atcaaattgt tggctcctct tggccttcac       360
ctgctgccct acagccccg ggttctcgtc agtgggattt gtgctgctgg aagcttcgtc        420
ctggttgcct tttctcattc tgtggggacc agcctgtgtg tgtggtcttc gctagcatc        480 tcatcaggcc ttggggaggt caccttcctc tccctcactg ccttctaccc cagggccgtg       540
atctcctggt ggtcctcagg gactggggga gctgggctgc tggggcccct gtcctacctg       600
ggcctcaccc aggccggcct ctcccctcag cagaccctgc tgtccatgct gggtatccct       660
gccctgctgc tggccagcta tttcttgttg ctcacatctc ctgaggccca ggaccctgga       720
ggggaagaag aagcagagag cgcagcccgg cagcccctca taagaaccga ggccccggag       780
tcgaagccag gctccagctc cagcctctcc cttcgggaaa ggtggacagt gttcaagggt       840
ctgctgtggt acattgttcc cttggtcgta gtttactttg ccgagtattt cattaaccag       900 ggacttttg aactcctctt tttctggaac acttccctga gtcacgctca gcaataccgc        960
tggtaccaga tgctgtacca ggctggcgtc tttgcctccc gctcttctct ccgctgctgt      1020
cgcatccgtt tcacctgggc cctggccctg ctgcagtgcc tcaacctggt gttcctgctg      1080
gcagacgtgt ggttcggctt tctgccaagc atctacctcg tcttcctgat cattctgtat      1140 gagggctcc tgggaggcgc agcctacgtg aacaccttcc acaacatcgc cctggagacc       1200
agtgatgagc accgggagtt tgcaatggcg gccacctgca tctctgacac actggggatc      1260
tccctgtcgg ggctcctggc tttgcctctg catgacttcc tctgccagct ctcctga        1317

<210> SEQ ID NO 3
<211> LENGTH: 546
<212> TYPE: DNA
<213> ORGANISM: Artificial Sequence
<220> FEATURE:
```

<223> OTHER INFORMATION: Synthetic Polynucleotide
<220> FEATURE:
<221> NAME/KEY: misc_feature
<223> OTHER INFORMATION: P546 promoter

<400> SEQUENCE: 3

```
gaacaacgcc aggctcctca acaggcaact tgctacttc tacagaaaat gataataaag      60
aaatgctggt gaagtcaaat gcttatcaca atggtgaact actcagcagg gaggctctaa    120
taggcgccaa gagcctagac ttccttaagc gccagagtcc acaagggccc agttaatcct    180
caacattcaa atgctgccca caaaaccagc ccctctgtgc cctagccgcc tctttttttcc   240
aagtgacagt agaactccac caatccgcag ctgaatgggg tccgcctctt ttccctgcct    300
aaacagacag gaactcctgc caattgaggg cgtcaccgct aaggctccgc cccagcctgg    360
gctccacaac caatgaaggg taatctcgac aaagagcaag gggtggggcg cgggcgcgca    420
ggtgcagcag cacacaggct ggtcgggagg gcggggcgcg acgtctgccg tgcggggtcc    480
cggcatcggt tgcgcgcgcg ctccctcctc tcggagagag ggctgtggta aaacccgtcc    540
ggaaaa                                                               546
```

<210> SEQ ID NO 4
<211> LENGTH: 2479
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: CLN3 gene cassette

<400> SEQUENCE: 4

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggaatt caattcacgc    120
gccggtaccg aattcacgcg tgaacaacgc caggctcctc aacaggcaac tttgctactt    180
ctacagaaaa tgataataaa gaaatgctgg tgaagtcaaa tgcttatcac aatggtgaac    240
tactcagcag ggaggctcta ataggcgcca agagcctaga cttccttaag cgccagagtc    300
cacaagggcc cagttaatcc tcaacattca aatgctgccc acaaaaccag ccctctgtg     360
ccctagccgc ctctttttc caagtgacag tagaactcca ccaatccgca gctgaatggg     420
gtccgcctct tttccctgcc taaacagaca ggaactcctg ccaattgagg gcgtcaccgc    480
taaggctccg cccagcctg gctccacaa ccaatgaagg gtaatctcga caaagagcaa      540
ggggtggggc gcgggcgcgc aggtgcagca gcacacaggc tggtcgggag ggcggggcgc    600
gacgtctgcc gtgcgggtc ccggcatcgg ttgcgcgcgc gctccctcct ctcggagaga     660
gggctgtggt aaacccgtc cggaaaacgc gtcgaagggc gaattctgca gataactggt     720
aagtttagtc ttttttgtct tttatttcag gtcccggatc cggtggtggt gcaaatcaaa    780
gaactgctcc tcagtcgatg ttgcctttac ttctaggcct gtacgaagt gttactaccg     840
gtatgggagg ctgtgcaggc tcgcggcggc gcttttcgga ttccgagggg gaggagaccg    900
tcccggagcc ccggctccct ctgttggacc atcagggcgc gcattggaag aacgcggtgg    960
gcttctggct gctgggcctt tgcaacaact ctcttatgt ggtgatgctg agtgccgccc    1020
acgacatcct tagccacaag aggacatcgg gaaaccagag ccatgtggac ccaggcccaa   1080
cgccgatccc ccacaacagc tcatcacgat ttgactgcaa ctctgtctct acggctgctg   1140
tgctcctggc ggacatcctc cccacactcg tcatcaaatt gttggctcct cttggccttc   1200
```

```
acctgctgcc ctacagcccc cgggttctcg tcagtgggat ttgtgctgct ggaagcttcg    1260
tcctggttgc cttttctcat tctgtgggga ccagcctgtg tggtgtggtc ttcgctagca    1320
tctcatcagg ccttggggag gtcaccttcc tctccctcac tgccttctac cccagggccg    1380
tgatctcctg gtggtcctca gggactgggg gagctgggct gctgggggcc ctgtcctacc    1440
tgggcctcac ccaggccggc ctctcccctc agcagaccct gctgtccatg ctgggtatcc    1500
ctgccctgct gctggccagc tatttcttgt tgctcacatc tcctgaggcc caggaccctg    1560
gaggggaaga agaagcagag agcgcagccc ggcagcccct cataagaacc gaggccccgg    1620
agtcgaagcc aggctccagc tccagcctct cccttcggga aggtggaca gtgttcaagg     1680 gtctgctgtg gtacattgtt cccttggtcg tagtttactt tgccgagtat tcattaacc     1740 agggacttt tgaactcctc ttttctgga cacttccct gagtcacgct cagcaatacc       1800
gctggtacca gatgctgtac caggctggcg tctttgcctc ccgctcttct ctccgctgct    1860
gtcgcatccg tttcacctgg gccctggccc tgctgcagtg cctcaacctg tgttcctgc     1920 tggcagacgt gtggttcggc tttctgccaa gcatctacct cgtcttcctg atcattctgt    1980 atgagggct cctgggaggc gcagcctacg tgaacacctt ccacaacatc gccctggaga    2040
ccagtgatga gcaccgggag tttgcaatgg cggccacctg catctctgac acactgggga    2100 tctcccctgtc ggggctcctg gctttgcctc tgcatgactt cctctgccag ctctcctgac   2160
ctgcaggcct cgactgtgcc ttctagttgc cagccatctg ttgtttgccc ctccccgtg     2220 ccttccttga ccctggaagg tgccactccc actgtccttt cctaataaaa tgaggaaatt    2280
gcatcgcatt gtctgagtag gtgtcattct attcgcatgc tggggagaga tcgatctgag    2340
gaacccctag tgatggagtt ggccactccc tctctgcgcg ctcgctcgct cactgaggcc    2400
gggcgaccaa aggtcgcccg acgcccgggc tttgcccggg cggcctcagt gagcgagcga    2460
gcgcgcagag agggagtgg                                                 2479
```

<210> SEQ ID NO 5
<211> LENGTH: 6008
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: pAAV.P546.CLN3.KAN plasmid

<400> SEQUENCE: 5

```
gcccaatacg caaaccgcct ctccccgcgc gttggccgat tcattaatgc agctggcgta      60
atagcgaaga ggcccgcacc gatcgccctt cccaacagtt gcgcagcctg aatggcgaat     120
ggcgattccg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg tggttacgc gcagcgtgac     480 cgctacactt gccagcgccc tagcgcccgc tcctttcgct ttcttccctt cctttctcgc    540
cacgttcgcc ggctttcccc gtcaagctct aaatcggggg ctcccttag ggttccgatt     600 tagtgcttta cggcaccctcg accccaaaaa acttgattag ggtgatggtt cacgtagtgg    660
```

| | |
|---|---|
| gccatcgccc tgatagacgg ttttcgccc tttgacgttg gagtccacgt tctttaatag | 720 |
| tggactcttg ttccaaactg aacaacact caacccatc tcggtctatt cttttgattt | 780 |
| ataagggatt ttgccgattt cggcctattg gttaaaaaat gagctgattt aacaaaaatt | 840 |
| taacgcgaat tttaacaaaa tattaacgct tacaatttaa atatttgctt atacaatctt | 900 |
| cctgttttg gggctttct gattatcaac cggggtacat atgattgaca tgctagtttt | 960 |
| acgattaccg ttcatcgccc tgcgcgctcg ctcgctcact gaggccgccc gggcaaagcc | 1020 |
| cgggcgtcgg gcgacctttg gtcgcccggc ctcagtgagc gagcgagcgc gcagagaggg | 1080 |
| agtggaattc aattcacgcg ccggtaccga attcacgcgt gaacaacgcc aggctcctca | 1140 |
| acaggcaact ttgctacttc tacagaaaat gataataaag aaatgctggt gaagtcaaat | 1200 |
| gcttatcaca atggtgaact actcagcagg gaggctctaa taggcgccaa gagcctagac | 1260 |
| ttccttaagc gccagagtcc acaagggccc agttaatcct caacattcaa atgctgccca | 1320 |
| caaaaccagc ccctctgtgc cctagccgcc tctttttcc aagtgacagt agaactccac | 1380 |
| caatccgcag ctgaatgggg tccgcctctt ttccctgcct aaacagacag gaactcctgc | 1440 |
| caattgaggg cgtcaccgct aaggctccgc cccagcctgg gctccacaac caatgaaggg | 1500 |
| taatctcgac aaagagcaag gggtgggcg cgggcgcgca ggtgcagcag cacacaggct | 1560 |
| ggtcgggagg gcggggcgcg acgtctgccg tgcgggtcc cggcatcggt tgcgcgcgcg | 1620 |
| ctccctcctc tcggagagag ggctgtggta aaaccgtcc ggaaaacgcg tcgaagggcg | 1680 |
| aattctgcag ataactggta agtttagtct ttttgtctt ttatttcagg tcccggatcc | 1740 |
| ggtggtggtg caaatcaaag aactgctcct cagtcgatgt tgcctttact tctaggcctg | 1800 |
| tacgaagtg ttactaccgg tatgggaggc tgtgcaggct cgcggcggcg cttttcggat | 1860 |
| tccgagggg aggagaccgt cccggagccc cggctccctc tgttggacca tcaggcgcg | 1920 |
| cattggaaga acgcggtggg cttctggctg ctgggccttt gcaacaactt ctcttatgtg | 1980 |
| gtgatgctga gtgccgccca cgacatcctt agccacaaga ggacatcggg aaaccagagc | 2040 |
| catgtggacc caggcccaac gccgatcccc cacaacagct catcacgatt tgactgcaac | 2100 |
| tctgtctcta cggctgctgt gctcctggcg gacatcctcc ccacactcgt catcaaattg | 2160 |
| ttggctcctc ttggccttca cctgctgccc tacagccccc gggttctcgt cagtgggatt | 2220 |
| tgtgctgctg gaagcttcgt cctggttgcc ttttctcatt ctgtggggac cagcctgtgt | 2280 |
| ggtgtggtct tcgctagcat tcatcaggc cttggggagg tcaccttcct ctccctcact | 2340 |
| gccttctacc caggggccgt gatctcctgg tggtcctcag ggactggggg agctgggctg | 2400 |
| ctgggggccc tgtcctacct gggcctcacc caggccggcc tctcccctca gcagaccctg | 2460 |
| ctgtccatgc tgggtatccc tgccctgctg ctggccagct atttcttgtt gctcacatct | 2520 |
| cctgaggccc aggaccctgg aggggaagaa gaagcagaga gcgcagcccg gcagcccctc | 2580 |
| ataagaaccg aggccccgga gtcgaagcca ggctccagct ccagcctctc ccttcgggaa | 2640 |
| aggtggacag tgttcaaggg tctgctgtgg tacattgttc ccttggtcgt agtttacttt | 2700 |
| gccgagtatt tcattaacca gggacttttt gaactcctct ttttctggaa cacttccctg | 2760 |
| agtcacgctc agcaataccg ctggtaccag atgctgtacc aggctggcgt cttgcctcc | 2820 |
| cgctcttctc tccgctgctg tcgcatccgt ttcacctggg ccctggccct gctgcagtgc | 2880 |
| ctcaacctgg tgttcctgct ggcagacgtg tggttcggct ttctgccaag catctacctc | 2940 |
| gtcttcctga tcattctgta tgaggggctc ctggaggcg cagcctacgt gaacaccttc | 3000 |

```
cacaacatcg ccctggagac cagtgatgag caccgggagt tgcaatggc ggccacctgc      3060 atctctgaca cactggggat ctccctgtcg gggctcctgg cttgcctct gcatgacttc       3120 ctctgccagc tctcctgacc tgcaggcctc gactgtgcct tctagttgcc agccatctgt     3180
tgtttgcccc tccccgtgc cttccttgac cctggaaggt gccactccca ctgtcctttc       3240
ctaataaaat gaggaaattg catcgcattg tctgagtagg tgtcattcta ttcgcatgct     3300
ggggagagat cgatctgagg aaccctagt gatggagttg ccactccct ctctgcgcgc         3360 tcgctcgctc actgaggccg ggcgaccaaa ggtcgcccga cgcccgggct tgcccgggc       3420 ggcctcagtg agcgagcgag cgcgcagaga gggagtggcc ccccccccc cccccccggc      3480 gattctcttg tttgctccag actctcaggc aatgacctga tagcctttgt agagacctct      3540
caaaaatagc taccctctcc ggcatgaatt tatcagctag aacggttgaa tatcatattg      3600
atggtgattt gactgtctcc ggcctttctc acccgtttga atctttacct acacattact      3660
caggcattgc atttaaaata tatgagggtt ctaaaaattt ttatccttgc gttgaaataa     3720
aggcttctcc cgcaaaagta ttacaggtc ataatgtttt tggtacaacc gatttagctt       3780
tatgctctga ggctttattg cttaattttg ctaattcttt gccttgcctg tatgatttat      3840
tggatgttgg aatcgcctga tgcggtattt tctccttacg catctgtgcg gtatttcaca      3900
ccgcatatgg tgcactctca gtacaatctg ctctgatgcc gcatagttaa gccagccccg      3960
acacccgcca acactatggt gcactctcag tacaatctgc tctgatgccg catagttaag     4020
ccagccccga caccgccaa cacccgctga cgcgccctga cgggcttgtc tgctcccggc      4080
atccgcttac agacaagctg tgaccgtctc cgggagctgc atgtgtcaga gttttcacc       4140 gtcatcaccg aaacgcgcga acgaaaggg cctcgtgata cgcctatttt tataggttaa      4200
tgtcatgaga caataaccct gataaatgct tcaataatat tgaaaaagga agagtatgag     4260
ccatattcaa cgggaaacgt cgaggccgcg attaaattcc aacatggatg ctgatttata    4320
tgggtataaa tgggctcgcg ataatgtcgg gcaatcaggt gcgacaatct atcgcttgta     4380
tgggaagccc gatgcgccag agttgtttct gaaacatggc aaaggtagcg ttgccaatga    4440
tgttacagat gagatggtca gactaaactg gctgacggaa tttatgccac ttccgaccat     4500
caagcatttt atccgtactc ctgatgatgc atggttactc accactgcga tccccggaaa    4560
aacagcgttc caggtattag aagaatatcc tgattcaggt gaaaatattg ttgatgcgct    4620
ggcagtgttc ctgcgccggt tgcactcgat tcctgtttgt aattgtcctt ttaacagcga    4680
tcgcgtattt cgcctcgctc aggcgcaatc acgaatgaat aacggtttgg ttgatgcgag    4740 tgatttgat gacgagcgta atggctggcc tgttgaacaa gtctggaaag aaatgcataa     4800
acttttgcca ttctcaccgg attcagtcgt cactcatggt gatttctcac ttgataacct     4860 tattttgac gaggggaaat taataggttg tattgatgtt ggacgagtcg gaatcgcaga      4920
ccgataccag gatcttgcca tcctatggaa ctgcctcggt gagttttctc cttcattaca    4980
gaaacggctt tttcaaaaat atggtattga taatcctgat atgaataaat tgcagtttca   5040
tttgatgctc gatgagtttt tctaactgtc agaccaagtt tactcatata cttagat       5100 tgatttaaaa cttcatttt aatttaaaag gatctaggtg aagatccttt tgataatct      5160 catgaccaaa atcccttaac gtgagttttc gttccactga gcgtcagacc ccgtagaaaa    5220
gatcaaagga tcttcttgag atcctttttt tctgcgcgta atctgctgct tgcaaacaaa   5280
aaaaccaccg ctaccagcgg tggtttgttt gccggatcaa gagctaccaa ctcttttttcc    5340 gaaggtaact ggcttcagca gagcgcagat accaaatact gttcttctag tgtagccgta    5400
```

```
gttaggccac cacttcaaga actctgtagc accgcctaca tacctcgctc tgctaatcct    5460
gttaccagtg gctgctgcca gtggcgataa gtcgtgtctt accgggttgg actcaagacg    5520
atagttaccg gataaggcgc agcggtcggg ctgaacgggg ggttcgtgca cacagcccag    5580
cttggagcga acgacctaca ccgaactgag atacctacag cgtgagctat gagaaagcgc    5640
cacgcttccc gaagggagaa aggcggacag gtatccggta agcggcaggg tcggaacagg    5700
agagcgcacg agggagcttc caggggggaaa cgcctggtat ctttatagtc ctgtcgggtt    5760
tcgccacctc tgacttgagc gtcgattttt gtgatgctcg tcaggggggc ggagcctatg    5820
gaaaaacgcc agcaacgcgg ccttttacg gttcctggcc ttttgctggc cttttgctca    5880
catgttcttt cctgcgttat cccctgattc tgtggataac cgtattaccg cctttgagtg    5940
agctgatacc gctcgccgca gccgaacgac cgagcgcagc gagtcagtga gcgaggaagc    6000
ggaagagc                                                             6008

<210> SEQ ID NO 6
<211> LENGTH: 106
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 5' ITR

<400> SEQUENCE: 6
ctgcgcgctc gctcgctcac tgaggccgcc cgggcaaagc ccgggcgtcg ggcgaccttt     60
ggtcgcccgg cctcagtgag cgagcgagcg cgcagagagg gagtgg                   106

<210> SEQ ID NO 7
<211> LENGTH: 100
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: SV40 Intron

<400> SEQUENCE: 7
ggtaagttta gtctttttg tcttttattt caggtcccgg atccggtggt ggtgcaaatc     60
aaagaactgc tcctcagtcg atgttgcctt tacttctagg                          100

<210> SEQ ID NO 8
<211> LENGTH: 147
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: BGH Poly A

<400> SEQUENCE: 8
cctcgactgt gccttctagt tgccagccat ctgttgtttg cccctccccc gtgccttcct     60
tgaccctgga aggtgccact cccactgtcc tttcctaata aaatgaggaa attgcatcgc    120
attgtctgag taggtgtcat tctattc                                        147

<210> SEQ ID NO 9
<211> LENGTH: 141
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 3' ITR

<400> SEQUENCE: 9
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag agagggagtg g                                               141

<210> SEQ ID NO 10
<211> LENGTH: 736
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: scAAV9 seuqence

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270
```

```
Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
        675                 680                 685
```

```
Lys Glu Asn Ser Lys Arg Trp Asn Pro Glu Ile Gln Tyr Thr Ser Asn
        690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 11
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 11
cgctagcatc tcatcaggcc ttg                                          23

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
agcatggaca gcagggtctg                                              20
```

ADENO-ASSOCIATED VIRUS DELIVERY OF CLN3 POLYNUCLEOTIDE

This application claims priority to U.S. Provisional Patent Application No. 62/800,911, filed Feb. 4, 2019, which is incorporated by reference herein in its entirety.

INCORPORATION BY REFERENCE OF THE SEQUENCE LISTING

This application contains, as a separate part of disclosure, a Sequence Listing in computer-readable form (filename: 53576_SeqListing.txt; 26,705 bytes—ASCII text file created Jan. 31, 2020) which is incorporated by reference herein in its entirety.

FIELD

The present disclosure relates to recombinant adeno-associated virus (rAAV) delivery of a ceroid lipofuscinosis neuronal 3 (CLN3) polynucleotide. The disclosure provides rAAV and methods of using the rAAV for CLN3 gene therapy of the neuronal ceroid lipofuscinosis (NCL) or CLN3-Batten Disease.

BACKGROUND

Neuronal ceroid lipofuscinoses (NCLs) are a group of severe neurodegenerative disorders.

Mutations in the CLN3 gene cause juvenile NCL or CLN3-Batten Disease (Kitzmu et al., Human Molecular Genetics 2008; 17(2):303-312; Munroe et al., Am J Hum Genet. 1997; 61:310-316), which has also been called Spielmeyer-Sjogren-Vogt disease. Mutations disturb the lysosomal storage clearance process. At this time, 67 disease causing-mutations have been described. However, 85% of patients are homozygous for the 1.02 kb deletion leading to the loss of exon 7 and exon 8. CLN3 mutations found in patients predominantly cause reduced abundance or functionality of the protein (battenin).

The typical age of onset in CLN3-Batten disease is between 4-7 years with insidious, but rapidly progressive vision loss. Children with juvenile NCL go from having normal vision to blindness in a matter of months, but can maintain light-dark perception for several years after. Cognitive and motor decline usually follows next (7-10 years of age) alongside with behavioral problems such as aggression (8-10 years of age), and then seizures (10-12 years of age). Parkinsonian features develop between 11-13 years of age. Cardiac conduction abnormalities have been reported in individuals at later stages of the disease. There is high phenotypic variability in individuals affected with CLN3-Batten disease, but all have low vision or progressive blindness in common. Moreover, the physical subscale of the Unified Batten Disease Rating Scale (UBDRS) that has been validated in 82 patients, shows a steady and measurable decline of 2.86 points per year (2.27-3.45, p<0.0001). The average survival is usually 15 years from symptom onset to end of life.

Therapeutic measures for CLN3-Batten disease have been wide-ranging in an effort to ameliorate disease. These include drug therapy such as EGIS-8332 and talampanel which target AMPA receptors, drugs that allow read-through of premature stop mutations, drugs to assist in break-down of accumulated storage material (cystagon/cysteamine), and even immune suppression therapy (mycophenolate, prednisolone). Enzyme replacement and stem cell therapies have also been evaluated. While many therapeutic approaches have been studied, few have been evaluated in a clinical setting. None are available that slow progression or cure the disease. Patients and families rely on treatments to ameliorate symptoms and palliative care.

The Cln3$^{\Delta ex7/8}$ mouse model was created in the early 2000s to mimic the most common disease-causing mutation in CLN3-Batten disease patients: an approximately 1 kb mutation that eliminates exons 7 and 8 from the CLN3 gene (Cotman et al., Hum Mol Genet. 2002; 11(22):2709-2721; Mole et al., Eur J Paediatr Neurol. 2001; 5:7-10). The mutation is found in a homozygous manner in 85% of the patients and as a heterozygous mutation in combination with point mutations on the other allele in an additional 15% of patients. The exon loss is predicted to produce a frameshift mutation, leading to a truncated protein product with lost or reduced activity (Lerner et al., Cell. 1995 Sep. 22; 82(6): 949-57; Kitzmuller et al., Hum Mol Genet. 2008 Jan. 15; 17(2):303-12). In their original study, Cotman et al. demonstrated the CLN3$^{\Delta ex7/8}$ mouse model successfully recapitulated several aspects of CLN3 disease. CLN3$^{\Delta ex7/8}$ animals accumulated autofluorescent storage material and ATP Synthase subunit C in the nervous system at various time points, and exhibited astrocyte reactivity in the brain starting at 10 months of age. Subsequent studies detailed altered glutamate receptor function in the cerebellum, corresponding with motor deficits on an accelerating rotarod assay (Cotman et al., Hum Mol Genet. 2002; 11(22):2709-2721). Behaviorally, Cln3$^{\Delta ex7/8}$ mice have been characterized at both young and mature time points, where neurodevelopmental motor delays were seen in neonatal and young adult mice, and deficits in gait and hind limb clasping were seen at 10-12 months of age (Cotman et al., Hum Mol Genet. 2002; 11(22):2709-2721; Osório et al., Genes Brain Behav. 2009 April; 8(3): 337-345). CLN3$^{\Delta ex7/8}$ mice do not appear to have functional visual impairments, but present with a slight survival deficit when compared to controls at 12 months of age (Cotman et al., Hum Mol Genet. 2002; 11(22):2709-2721; Seigel et al., Mol Cell Neurosci. 2002 April; 19(4):515-27). Taken together, the Cln3$^{\Delta ex7/8}$ mouse model carrying the most frequent human mutation, exhibits numerous cellular and behavioral changes consistent with CLN3-Batten disease, making it a suitable model for testing therapies.

There thus remains a need in the art for treatments for CLN3-Batten Disease.

SUMMARY

Provided herein are methods and products for CLN3 gene therapy using recombinant AAV.

Provided herein are recombinant adeno-associated virus 9 (rAAV9) encoding a CLN3 polypeptide, comprising an rAAV9 genome comprising in 5' to 3' order: a P546 promoter, and a polynucleotide encoding the CLN3 polypeptide. In some embodiments, the rAAV9 genome comprises a self-complementary genome. In some embodiments, the rAAV9 genome comprises a single-stranded genome.

Self-complementary recombinant adeno-associated virus 9 (scAAV9) are provided encoding the CLN3 polypeptide set out in SEQ ID NO: 1, in which the genome of the scAAV9 comprises in 5' to 3' order: a first AAV inverted terminal repeat, a P546 promoter comprising the sequence of SEQ ID NO: 3, a polynucleotide encoding the CLN3 polypeptide set out in SEQ ID NO: 1 and a second AAV inverted terminal repeat. The polynucleotide encoding the CLN3 polypeptide may be at least 90% identical to SEQ ID NO: 2.

Also provided are scAAV9 with a genome comprising in 5' to 3' order: a first AAV inverted terminal repeat, a P546 promoter comprising the sequence of SEQ ID NO: 3, an SV40 intron, a polynucleotide encoding the CLN3 polypeptide of SEQ ID NO: 1 and a second AAV inverted terminal repeat; scAAV9 with a genome comprising in 5' to 3' order: a first AAV inverted terminal repeat, a P546 promoter comprising the sequence of SEQ ID NO: 3, a polynucleotide encoding the CLN3 polypeptide of SEQ ID NO: 1, a bovine growth hormone polyadenylation poly A sequence and a second AAV inverted terminal repeat. In an exemplary embodiment, the scAAV9 has a genome comprising the gene cassette set out in SEQ ID NO: 4.

Single-stranded recombinant adeno-associated virus 9 (ssAAV9) are provided encoding the CLN3 polypeptide set out in SEQ ID NO: 1, in which the genome of the ssAAV9 comprises in 5' to 3' order: a first AAV inverted terminal repeat, a P546 promoter comprising the sequence of SEQ ID NO: 3, a polynucleotide encoding the CLN3 polypeptide set out in SEQ ID NO: 1 and a second AAV inverted terminal repeat. The polynucleotide encoding the CLN3 polypeptide may be at least 90% identical to SEQ ID NO: 2. Also provided are ssAAV9 with a genome comprising in 5' to 3' order: a first AAV inverted terminal repeat, a P546 promoter comprising the sequence of SEQ ID NO: 3, an SV40 intron, a polynucleotide encoding the CLN3 polypeptide of SEQ ID NO: 1 and a second AAV inverted terminal repeat; ssAAV9 with a genome comprising in 5' to 3' order: a first AAV inverted terminal repeat, a P546 promoter comprising the sequence of SEQ ID NO: 3, a polynucleotide encoding the CLN3 polypeptide of SEQ ID NO: 1, a bovine growth hormone polyadenylation poly A sequence and a second AAV inverted terminal repeat.

The nucleic acid sequence set out in SEQ ID NO: 4 is the gene cassette that is provided in FIG. 1A. Provided are rAAV9 with an scAAV9 genome or an ssAAV9 genome comprising a nucleic acid sequence that is at least 90% identical to the nucleic acid sequence of SEQ ID NO: 4, or at least 95% identical to the nucleic acid sequence of SEQ ID NO: 4, or at least 98% identical to the nucleic acid sequence of SEQ ID NO: 4.

Nucleic acid molecules comprising a first AAV inverted terminal repeat, a P546 promoter comprising the sequence of SEQ ID NO: 3, a nucleic acid sequence encoding the CLN3 polypeptide of SEQ ID NO: 1 and a second AAV inverted terminal repeat are also provided. In some embodiments, the polynucleotide encoding the CLN3 polypeptide is at least 90% identical to SEQ ID NO: 2.

Also provided are nucleic acid molecules comprising a first AAV inverted terminal repeat, a P546 promoter comprising the nucleotide sequence of SEQ ID NO: 3, an SV40 intron, a nucleic acid sequence encoding the CLN3 polypeptide of SEQ ID NO: 1 and a second AAV inverted terminal repeat. Additionally provided are polynucleotides comprising a first AAV inverted terminal repeat, a P546 promoter comprising the nucleotide sequence of SEQ ID NO: 3, a nucleic acid encoding the CLN3 polypeptide of SEQ ID NO: 1, a bovine growth hormone polyadenylation poly A sequence and a second AAV inverted terminal repeat. In any of the polynucleotides provided, the CLN3 polypeptide may be encoded by the nucleic acid sequence set out in SEQ ID NO: 2 or a sequence at least 90% identical to SEQ ID NO: 2.

rAAV9, scAAV9, or ssAAV9 comprising any of the polynucleotides are provided. rAAV with single-stranded genomes are also provided.

Further provided are rAAV9 viral particles encoding a CLN3 polypeptide, wherein the rAAV9 genome comprises in 5' to 3' order: a first AAV inverted terminal repeat, the P546 promoter comprising a nucleic acid sequence at least 90% identical to SEQ ID NO: 3, the polynucleotide encoding a CLN3 polypeptide at least 90% identical to the amino acid sequence of SEQ ID NO: 1, and a second AAV inverted terminal repeat. The rAAV9 particles provided may comprise a polynucleotide encoding the CLN3 polypeptide comprising an amino acid sequence at least 90% identical to SEQ ID NO: 1. In addition, the rAAV9 viral particles may comprise an AAV9 genome comprising a nucleic acid sequence at least 90% identical to the nucleic acid sequence of SEQ ID NO: 4, at least 95% identical to nucleic acid sequence of SEQ ID NO: 4 or at least 98% identical to the nucleic acid sequence of SEQ ID NO: 4. Any of the rAAV9 viral particles may further comprise an SV40 intron, and/or a BGH poly-A sequence.

In any of the rAAV, ssAAV, and the scAAV provided, the AAV inverted terminal repeats may be AAV2 inverted terminal repeats.

Also provided are nucleic acid molecules comprising an rAAV9 genome comprising in 5' to 3' order: a first AAV inverted terminal repeat, a P546 promoter comprising a nucleic acid sequence at least 90% identical to SEQ ID NO: 3, and a polynucleotide encoding a CLN3 polypeptide at least 90% identical to the amino acid sequence of SEQ ID NO: 1. The provided nucleic acid molecules may comprise a self-complementary genome or a single-stranded genome.

Further provided are nucleic acid molecules comprising a rAAV9 genome that comprises in 5' to 3' order: a first AAV inverted terminal repeat, the P546 promoter comprising a nucleic acid sequence at least 90% identical to SEQ ID NO: 3, the polynucleotide encoding a CLN3 polypeptide at least 90% identical to the amino acid sequence of SEQ ID NO: 1, and a second AAV inverted terminal repeat. The nucleic acid molecules provided may comprise a polynucleotide encoding the CLN3 polypeptide comprising an amino acid sequence at least 90% identical to amino acid sequence of SEQ ID NO: 1. In addition, the nucleic acid molecules may comprise an AAV9 genome comprising a nucleic acid sequence at least 90% identical to the nucleic acid sequence of SEQ ID NO: 4, at least 95% identical to nucleic acid sequence of SEQ ID NO: 4, at least 98% identical to the nucleic acid sequence of SEQ ID NO: 4. Any of the nucleic acid molecules provided may further comprise an SV40 intron, and/or a BGH poly-A sequence.

Further provided are compositions comprising the scAAV9 described herein, the ssAAV9 described herein, nucleic acid molecules described herein or the rAAV viral particles described herein and at least one pharmaceutically acceptable excipient. In some instances, the pharmaceutically acceptable excipient comprises a non-ionic low osmolar compound, a buffer, a polymer, a salt, or a combination thereof. In some embodiments, the polymer is a copolymer. In some embodiments, the copolymer is a poloxamer. For example, the composition may at least comprise a pharmaceutically acceptable excipient comprising a non-ionic, low-osmolar compound. For example, the pharmaceutically acceptable excipient comprises about 20 to 40% non-ionic, low-osmolar compound or about 25% to about 35% non-ionic, low-osmolar compound. An exemplary composition comprises scAAV formulated in 20 mM Tris (pH8.0), 1 mM $MgCl_2$, 200 mM NaCl, 0.001% poloxamer 188 and about 25% to about 35% non-ionic, low-osmolar compound. Another exemplary composition comprises scAAV formulated in 1×PBS and 0.001% Polyoxyethylene-Polyoxypropylene Block Copolymer (PLURIONIC® F-68).

Still further provided are methods of treating CLN3-Batten Disease in a subject comprising administering to the subject a composition comprising a therapeutically effective amount of any of the rAAV9 viral particles disclosed herein, any of the scAAV9 disclosed herein, any of the ssAAV9 disclosed herein, any of the nucleic acid molecules described herein or any of the compositions described herein.

In any of the methods provided, the compositions, rAAV9, ssAAV9, scAAV9 and/or nucleic acid molecules are administered via a route selected from the group consisting of intrathecal, intracerebroventricular, intraparenchymal, intravenous, and a combination thereof.

Use of a therapeutically effective amount of any of the rAAV9 viral particles disclosed herein, any of the scAAV9 disclosed herein, any of the ssAAV9 disclosed herein, any of the nucleic acid molecules described herein or any of the compositions described herein for preparation of medicament for treating CLN3-Batten Disease in a subject in need thereof.

Also provided are compositions comprising a therapeutically effective amount of any of the rAAV9 viral particles disclosed herein, any of the scAAV9 disclosed herein, any of the ssAAV9 disclosed herein, any of the nucleic acid molecules described herein or any of the compositions described for treating CLN3-Batten Disease in a subject in need thereof.

Exemplary doses of the scAAV9, ssAAV9, or rAAV9 administered by the intrathecal route are about $1\times10^{11}$ vg of the scAAV9, ssAAV9, or rAAV9 viral particles subject to about $2\times10^{15}$ vg per subject, or about $1\times10^{11}$ vg of the scAAV9, ssAAV9, or rAAV9 viral particles per subject to about $1\times10^{15}$ vg of the scAAV9, ssAAV9, or AAV9 viral particles per subject, or about $1\times10^{12}$ vg of the scAAV9, ssAAV9, or rAAV9 viral particles per subject to about $1\times10^{14}$ vg of the scAAV9, ssAAV9, or AAV9 viral particles per subject, or about $1\times10^{12}$ vg of the scAAV9, ssAAV9, or rAAV9 viral particles per subject to about $1\times10^{15}$ vg of the scAAV9, ssAAV9, or AAV9 viral particles per subject. For example, about $1\times10^{13}$ vg of the scAAV9, ssAAV9, or AAV9 viral particles is administered to a subject, or about $1.5\times10^{13}$ of the scAAV9, ssAAV9, or AAV9 viral particles is administered to a subject, or about $3.4\times10^{13}$ of the scAAV9, ssAAV9, or AAV9 viral particles is administered to a subject or about $6\times10^{13}$ vg of the scAAV9, ssAAV9, or AAV9 viral particles is administered to a subject or about $1.2\times10^{14}$ of the scAAV9, ssAAV9, or AAV9 viral particles is administered to a subject, or about $2\times10^{14}$ of the scAAV9, ssAAV9, or AAV9 viral particles is administered to a subject.

The methods, medicaments or compositions for treatment result in a subject, in comparison to the subject before treatment or an untreated CLN3-Batten Disease patient, in one or more of: (a) reduced or slowed lysosomal accumulation of autofluorescent storage material, (b) reduced or slowed lysosomal accumulation of ATP Synthase Subunit C, (c) reduced or slowed glial activation (astrocytes and/or microglia) activation, (d) reduced or slowed astrocytosis, (e) reduced or slowed brain volume loss measured by MRI, (f) reduced or slowed onset of seizures, and (g) stabilization, reduced or slowed progression, or improvement in one or more of the scales that are used to evaluate progression and/or improvement in CLN3 Batten-disease, e.g. the Unified Batten Disease Rating System (UBDRS) assessment scales or the Hamburg Motor and Language Scale. The subject can be held in the Trendelenburg position after administering the rAAV9, ssAAV9, or the scAAV or the nucleic acid molecules disclosed herein.

Still further provided are methods of treating CLN3 disease in a patient in need comprising delivering a composition comprising any one of the rAAV viral disclosed provided herein, any of the scAAV9 disclosed herein, any of the ssAAV9 disclosed herein, any of the nucleic acid molecules described herein, any of the composition described herein or any of the medicaments described herein to a brain or spinal cord of a patient in need thereof.

In any of the methods or uses provided, the composition or medicament may be delivered by intrathecal, intracerebroventricular, intraparenchymal, or intravenous injection of a combination thereof. Any of the methods provided may further comprise placing the patient in the Trendelenburg position after intrathecal injection of the composition, rAAV9 viral particles or the scAAV or the nucleic acid molecules disclosed herein.

In any of the methods or uses provided the compositions or medicaments may comprise a non-ionic, low-osmolar contrast agent. For example, the compositions comprise a non-ionic, low-osmolar contrast agent is selected from the group consisting of iobitridol, iohexol, iomeprol, iopamidol, iopentol, iopromide, ioversol, ioxilan, and combinations thereof.

The compositions or medicaments administered may comprise a pharmaceutically acceptable excipient. For example, the pharmaceutically acceptable excipient comprises about 20 to 40% non-ionic, low-osmolar compound or about 25% to about 35% non-ionic, low-osmolar compound. An exemplary composition comprises scAAV formulated in 20 mM Tris (pH8.0), 1 mM MgCl2, 200 mM NaCl, 0.001% poloxamer 188 and about 25% to about 35% non-ionic, low-osmolar compound. Another exemplary composition comprises scAAV formulated in 1×PBS and 0.001% Polyoxyethylene-polyoxypropylene block copolymer (PLURIONIC® F-68)

In any of the methods or used provided, when the composition or medicament is delivered to the brain or spinal cord, the composition may be delivered to a brain stem, or may be delivered to the cerebellum, or may be delivered to a visual cortex, or may be delivered to a motor cortex. Further, in any of the methods or uses provided, when the composition or medicament is delivered to the brain or spinal cord, the composition may be delivered to a nerve cell, a glial cell, or both. For example, wherein the delivering to the brain or spinal cord comprises delivery to a cell of the nervous system such as a neuron, a lower motor neuron, a microglial cell, an oligodendrocyte, an astrocyte, a Schwann cell, or a combination thereof.

The methods, uses or administration of the composition or medicament result in a subject, in comparison to the subject before treatment or to an untreated subject, in one or more of: (a) reduced or slowed lysosomal accumulation of autofluorescent storage material, (b) reduced or slowed lysosomal accumulation of ATP Synthase Subunit C, (c) reduced or slowed glial activation (astrocytes and/or microglia) activation, (d) reduced or slowed astrocytosis, (e) reduced or slowed brain volume loss measured by MRI, (f) reduced or slowed onset of seizures, and (g) stabilization, reduced or slowed progression, or improvement in one or more of the scales that are used to evaluate progression and/or improvement in CLN3 Batten-disease, e.g. the Unified Batten Disease Rating System (UBDRS) assessment scales or the Hamburg Motor and Language Scale.

The headings herein are for the convenience of the reader and not intended to be limiting.

The use of 'may' and 'can' herein is to describe the various embodiments that are included within the claims, and not to indicate uncertainty about the scope of the claims.

BRIEF DESCRIPTION OF THE DRAWINGS

FIG. 6A: Representative images (6 month time point) of fixed tissue sections stained for GFAP as a marker for activated astrocytes and visualized with DAB staining. FIG. 6B: Quantification of GFAP-positive area in PBS-injected WT ("WT"), PBS-injected CLN3$^{\Delta ex7/8}$ ("CLN3"), and scAAV9.P546.CLN3-injected CLN3$^{\Delta ex7/8}$ ("CLN3-AAV") mice at 4 months and 6 months post-injection. N=5 for each group and time point. S1BF=barrel cortex. VPM/VPL=ventral posteromedial/ventral posterolateral nucleus.

FIG. 7A: Representative images (6 month time point) of fixed tissue sections stained for CD68 as a marker for activated microglia and visualized with DAB staining. FIG. 7B: Quantification of CD68-positive area in PBS injected WT ("WT"), PBS-injected CLN3$^{\Delta ex7/8}$ ("CLN3"), and scAAV9.P546.CLN3-injected CLN3$^{\Delta ex7/8}$ ("CLN3-AAV") mice at 4 months and 6 months post-injection. N=5 for each group and time point. S1BF=barrel cortex. VPM/VPL=ventral posteromedial/ventral posterolateral nucleus.

FIG. 14 provides the nucleic acid sequence of scAAV9.P546.CLN3 gene cassette (SEQ ID NO: 4). The AAV2 ITR nucleic acid sequence is in italics (5'ITR is set out as SEQ ID NO: 6 and the 3' ITR is set out as SEQ ID NO: 9), the P546 promoter nucleic acid sequence (SEQ ID NO: 3) is underlined with a single line, the SV40 intron nucleic acid sequence (SEQ ID NO: 7) is underlined with a double line, the nucleic acid sequence of the human CLN3 cDNA sequence (SEQ ID NO: 2) is in bold, the nucleic acid sequence of the BGH polyA terminator (SEQ ID NO: 8) is underlined with a dotted line.

FIG. 15A-B provides the nucleic acid sequence of full length AAV.P546.CLN3 (SEQ ID NO: 5).

FIG. 36 demonstrates that scAAV9.p546.CLN3 mice show differing levels of microglia (CD68+) activation in the VPM-VPL, thalamus based on sex. Mean±SEM, Ordinary Two-way ANOVA with Tukey's post-hoc test, $*p<0.05$, $p<0.01$, $*p<0.001$, $****p<0.0001$.

FIG. 37 demonstrates that scAAV9.p546.CLN3 mice show differing levels of activated microglia (CD68+) in the Mediodorsal Nucleus (MD) based on sex. Mean±SEM, Ordinary Two-way ANOVA with Tukey's post-hoc test, $*p<0.05$, $p<0.01$, $*p<0.001$, $****p<0.0001$.

FIG. 38 demonstrates that scAAV9.p546.CLN3 mice show differing levels of activated microglia (CD68+) in the Submedial Nucleus (SM) based on sex. Mean±SEM, Ordinary Two-way ANOVA with Tukey's post-hoc test, $*p<0.05$, $p<0.01$, $*p<0.001$, $****p<0.0001$.

DETAILED DESCRIPTION

Figure 1:
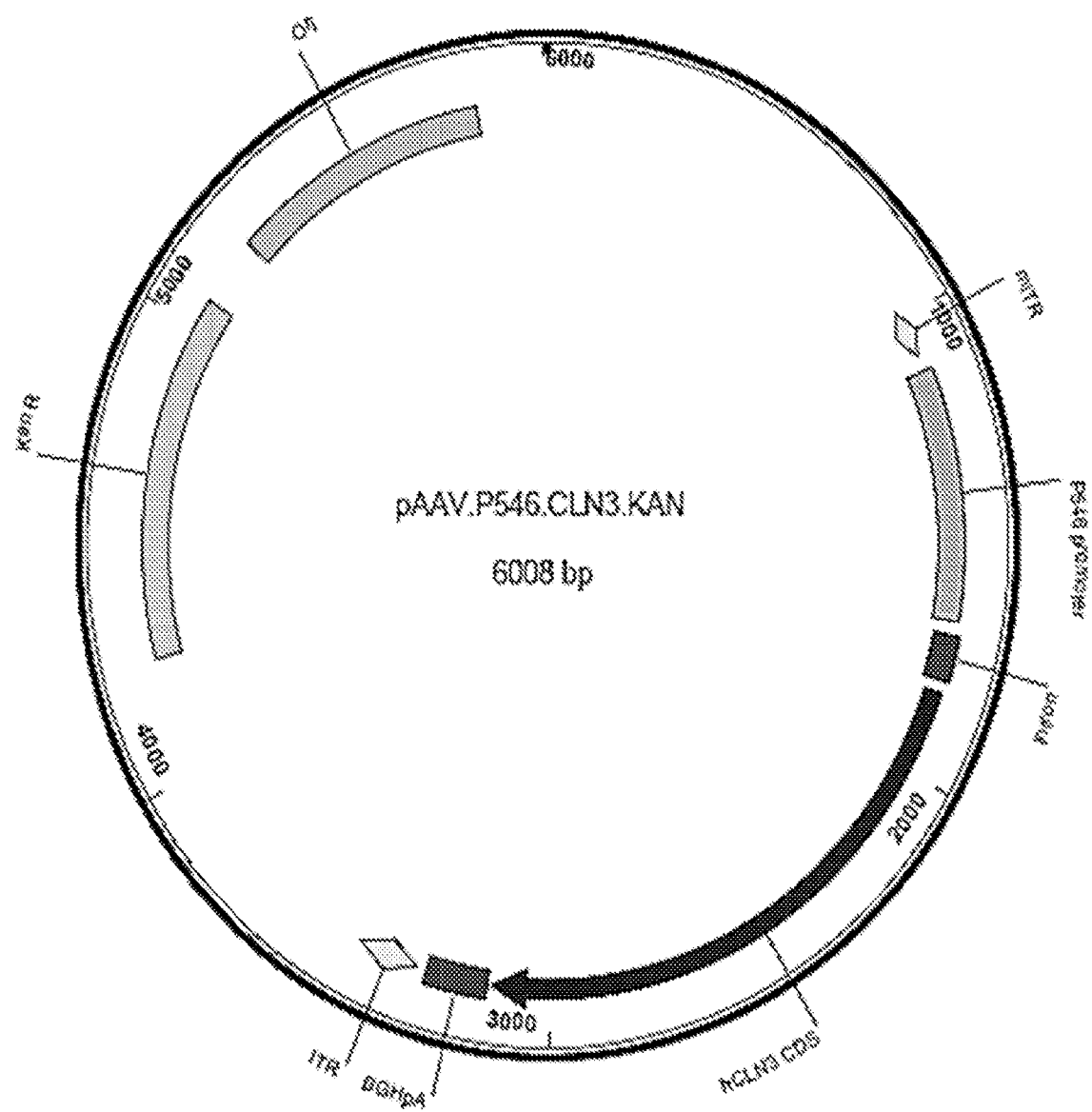
FIG. 1 provides schematics of the (FIG. 1A) the scAAV9.P546.CLN3 gene cassette and (FIG. 1B) plasmid construct pAAV.P546.CLN3.KAN used for production of scAAV9.P546.CLN3. A human CLN3 cDNA was inserted under the control of the P546 promoter between Inverted Terminal Repeat (ITR) structures derived from AAV2. SV40 Intron (upstream of human CLN3 cDNA) and Bovine Growth Hormone polyadenylation (BGH Poly A) terminator sequence (downstream of human CLN3 cDNA) help in mRNA processing and enhance the transgene expression. The sequence of the plasmid construct pAAV.P546.CLN3.KAN is set out in SEQ ID NO: 5. The genome is packaged in AAV9 capsid protein.

The present disclosure provides methods and products for treating CLN3-Batten Disease. The methods involve delivery of a CLN3 polynucleotide to a subject using rAAV as a gene delivery vector.

Adeno-associated virus (AAV) is a replication-deficient parvovirus, the single-stranded DNA genome of which is about 4.7 kb in length including 145 nucleotide inverted terminal repeat (ITRs) and may be used to refer to the virus itself or derivatives thereof. The term covers all subtypes and both naturally occurring and recombinant forms, except where specified otherwise. There are multiple serotypes of AAV. The serotypes of AAV are each associated with a specific clade, the members of which share serologic and functional similarities. Thus, AAVs may also be referred to by the clade. For example, AAV9 sequences are referred to as "clade F" sequences (Gao et al., J. Virol., 78: 6381-6388 (2004). The present disclosure contemplates the use of any sequence within a specific clade, e.g., clade F. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in *Mol. Ther.*, 13(1): 67-76 (2006); the AAV-11 genome is provided in *Virology*, 330(2): 375-383 (2004); portions of the AAV-12 genome are provided in Genbank Accession No. DQ813647; portions of the AAV-13 genome are provided in Genbank Accession No. EU285562. The sequence of the AAV rh.74 genome is provided in see U.S. Pat. No. 9,434,928, incorporated herein by reference. The sequence of the AAV-B1 genome is provided in Choudhury et al., *Mol. Ther.*, 24(7): 1247-1257 (2016). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The native AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. In some instances, the rep and cap proteins are provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

The term "AAV" as used herein refers to the wild type AAV virus or viral particles. The terms "AAV," "AAV virus," and "AAV viral particle" are used interchangeably herein. The term "rAAV" refers to a recombinant AAV virus or recombinant infectious, encapsulated viral particles. The terms "rAAV," "rAAV virus," and "rAAV viral particle" are used interchangeably herein.

The term "rAAV genome" refers to a polynucleotide sequence that is derived from a native AAV genome that has been modified. In some embodiments, the rAAV genome has been modified to remove the native cap and rep genes. In some embodiments, the rAAV genome comprises the endogenous 5' and 3' inverted terminal repeats (ITRs). In some embodiments, the rAAV genome comprises ITRs from an AAV serotype that is different from the AAV serotype from which the AAV genome was derived. In some embodiments, the rAAV genome comprises a transgene of interest (e.g., a CLN3-encoding polynucleotide) flanked on the 5' and 3' ends by inverted terminal repeat (ITR). In some embodiments, the rAAV genome comprises a "gene cassette." An exemplary gene cassette is set out in FIG. 1A and the nucleic acid sequence of SEQ ID NO: 4. The rAAV genome can be a self-complementary (sc) genome, which is referred to herein as "scAAV genome." Alternatively, the rAAV genome can be a single-stranded (ss) genome, which is referred to herein as "ssAAV genome."

The term "scAAV" refers to a rAAV virus or rAAV viral particle comprising a self-complementary genome. The term "ssAAV" refers to a rAAV virus or rAAV viral particle comprising a single-stranded genome.

rAAV genomes provided herein may comprise a polynucleotide encoding a CLN3 polypeptide. CLN3 polypeptides comprise the amino acid sequence set out in SEQ ID NO: 1, or a polypeptide with an amino acid sequence that is at least: 90%, 91%, 92%, 93%, 94%, 95%, 96%, 97%, 98%, or 99% identical to the amino acid sequence set forth in SEQ ID NO: 1, and which encodes a polypeptide with CLN3 activity (e.g., at least one of increasing clearance of lysosomal auto-fluorescent storage material, reducing lysosomal accumulation of ATP synthase subunit C, and reducing activation of astrocytes and microglia in a patient when treated as compared to, e.g. the patient prior to treatment).

rAAV genomes provided herein, in some cases, comprise a polynucleotide encoding a CLN3 polypeptide wherein the polynucleotide has the nucleotide sequence set out in SEQ ID NO: 2, or a polynucleotide at least: 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence set forth in SEQ ID NO: 2 and encodes a polypeptide with CLN3 activity (e.g., at least one of increasing clearance of lysosomal auto-fluorescent storage material, reducing lysosomal accumulation of ATP synthase subunit C, and reducing activation of astrocytes and microglia in a patient when treated as compared to, e.g. the patient prior to treatment).

rAAV genomes provided herein, in some embodiments, comprise a polynucleotide sequence that encodes a polypeptide with CLN3 activity and that hybridizes under stringent conditions to the nucleic acid sequence of SEQ ID NO: 2, or the complement thereof. The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing include but are not limited to 0.015 M sodium chloride, 0.0015 M sodium citrate at 65-68° C. or 0.015 M sodium chloride, 0.0015M sodium citrate, and 50% formamide at 42° C. See, for example, Sambrook et al., Molecular Cloning: A Laboratory Manual, 2nd Ed., Cold Spring Harbor Laboratory, (Cold Spring Harbor, N.Y. 1989).

The rAAV genomes provided herein, in some embodiments, comprise one or more AAV ITRs flanking the polynucleotide encoding a CLN3 polypeptide. The CLN3 polynucleotide is operatively linked to transcriptional control elements (including, but not limited to, promoters, enhancers and/or polyadenylation signal sequences) that are functional in target cells to form a gene cassette. Examples of promoters are the chicken B actin promoter and the P546 promoter. Additional promoters are contemplated herein including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Additionally provided herein are a P546 promoter sequence set out in SEQ ID NO: 3, and promoter sequences at least: 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence set forth in SEQ ID NO: 3 that are promoters with P546 transcription promoting activity. Other examples of transcription control elements are tissue specific control elements, for example, promoters that allow expression specifically within neurons or specifically within astrocytes. Examples include neuron specific enolase and glial fibrillary acidic protein promoters. Inducible promoters are also contemplated. Non-limiting examples of inducible promoters include, but are not limited to a metallothionine promoter, a glucocorticoid promoter, a progesterone promoter, and a tetracycline-regulated promoter. The gene cassette may also include intron sequences to facilitate processing of a CLN3 RNA transcript when expressed in mammalian cells. One example of such an intron is the SV40 intron. "Packaging" refers to a series of intracellular events that result in the assembly and encapsidation of an AAV particle. The term "production" refers to the process of producing the rAAV (the infectious, encapsulated rAAV particles) by the packing cells.

AAV "rep" and "cap" genes refer to polynucleotide sequences encoding replication and encapsidation proteins, respectively, of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses may encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allows AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

The rAAV genomes provided herein lack AAV rep and cap DNA. AAV DNA in the rAAV genomes (e.g., ITRs) contemplated herein may be from any AAV serotype suitable for deriving a recombinant virus including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV rh.74 and AAV-B1. As noted above, the nucleotide sequences of the genomes of various AAV serotypes are known in the art. rAAV with capsid mutations are also contemplated. See, for example, Marsic et al., *Molecular Therapy*, 22(11): 1900-1909 (2014). Modified capsids herein are also contemplated and include capsids having various post-translational modifications such as glycosylation and deamidation. Deamidation of asparagine or glutamine side chains resulting in conversion of asparagine residues to aspartic acid or isoaspartic acid residues, and conversion of glutamine to glutamic acid or isoglutamic acid is contemplated in rAAV capsids provided herein. See, for example, Giles et al., Molecular Therapy, 26(12): 2848-2862 (2018). Modified capsids herein are also contemplated to comprise targeting sequences directing the rAAV to the affected tissues and organs requiring treatment.

DNA plasmids provided herein comprise rAAV genomes described herein. The DNA plasmids may be transferred to cells permissible for infection with a helper virus of AAV (e.g., adenovirus, E1-deleted adenovirus or herpesvirus) for assembly of the rAAV genome into infectious viral particles with AAV9 capsid proteins. Techniques to produce rAAV, in which an rAAV genome to be packaged, rep and cap genes, and helper virus functions are provided to a cell are standard in the art. Production of rAAV particles requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs. Production of pseudotyped rAAV is disclosed in, for example, WO 01/83692 which is incorporated by reference herein in its entirety. In various embodiments, AAV capsid proteins may be modified to enhance delivery of the recombinant rAAV. Modifications to capsid proteins are generally known in the art. See, for example, US 2005/0053922 and US 2009/0202490, the disclosures of which are incorporated by reference herein in their entirety.

A method of generating a packaging cell is to create a cell line that stably expresses all the necessary components for rAAV production. For example, a plasmid (or multiple plasmids) comprising a rAAV genome lacking AAV rep and cap genes, AAV rep and cap genes separate from the rAAV genome, and a selectable marker, such as a neomycin resistance gene, may be integrated into the genome of a cell. rAAV genomes may be introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line may then be infected with a helper virus such as adenovirus. The advantages of this method are that the cells are selectable and are suitable for large-scale production of rAAV. Other non-limiting examples of suitable methods employ adenovirus or baculovirus rather than plasmids to introduce rAAV genomes and/or rep and cap genes into packaging cells.

General principles of rAAV particle production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV particle production.

Further provided herein are packaging cells that produce infectious rAAV particles. In one embodiment packaging cells may be stably transformed cancer cells such as HeLa cells, 293 cells and PerC.6 cells (a cognate 293 line). In another embodiment, packaging cells may be cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Also provided herein are rAAV (e.g., infectious encapsidated rAAV particles) comprising a rAAV genome of the disclosure. The genomes of the rAAV lack AAV rep and cap DNA, that is, there is no AAV rep or cap DNA between the ITRs of the genomes of the rAAV. The rAAV genome can be a self-complementary (sc) genome. A rAAV with a sc genome is referred to herein as a scAAV. The rAAV genome can be a single-stranded (ss) genome. A rAAV with a single-stranded genome is referred to herein as an ssAAV.

An exemplary rAAV provided herein is the scAAV named "scAAV9.P546.CLN3." The scAAV9.P546.CLN3 scAAV contains a scAAV genome comprising a human CLN3 cDNA under the control of a P546 promoter (SEQ ID NO: 3). The scAAV genome also comprises a SV40 Intron (upstream of human CLN3 cDNA) and Bovine Growth Hormone polyadenylation (BGH Poly A) terminator sequence (downstream of human CLN3 cDNA). The sequence of this scAAV9.P546.CLN3 gene cassette is set out in SEQ ID NO: 4. The scAAV genome is packaged in an AAV9 capsid and includes AAV2 ITRs (one ITR upstream of the P546 promoter and the other ITR downstream of the BGH Poly A terminator sequence).

The rAAV may be purified by methods standard in the art such as by column chromatography or cesium chloride gradients. Methods for purifying rAAV from helper virus are known in the art and may include methods disclosed in, for example, Clark et al., Hum. Gene Ther., 10(6): 1031-1039 (1999); Schenpp and Clark, Methods Mol. Med., 69: 427-443 (2002); U.S. Pat. No. 6,566,118 and WO 98/09657.

Compositions comprising rAAV are also provided. Compositions comprise an rAAV encoding a CLN3 polypeptide. Compositions may include two or more rAAV encoding different polypeptides of interest. In some embodiments, the rAAV is scAAV or ssAAV.

Compositions provided herein comprise rAAV and a pharmaceutically acceptable excipient or excipients. Acceptable excipients are nontoxic to recipients and are preferably inert at the dosages and concentrations employed, and include, but are not limited to, buffers such as phosphate [e.g., phosphate-buffered saline (PBS)], citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, copolymers such as poloxamer 188, pluronics (e.g., Polyoxyethylene-polyoxypropylene block copolymer (PLURIONIC® F-68)) or polyethylene glycol (PEG). Compositions provided herein can comprise a pharmaceutically acceptable aqueous excipient containing a non-ionic, low-osmolar compound such as iobitridol, iohexol, iomeprol, iopamidol, iopentol, iopromide, ioversol, or ioxilan, where the aqueous excipient containing the non-ionic, low-osmolar compound can have one or more of the following characteristics: about 180 mgI/mL, an osmolality by vapor-pressure osmometry of about 322 mOsm/kg water, an osmolarity of about 273 mOsm/L, an absolute viscosity of about 2.3 cp at 20° C. and about 1.5 cp at 37° C., and a specific gravity of about 1.164 at 37° C. Exemplary compositions comprise about 20 to 40% non-ionic, low-osmolar compound or about 25% to about 35% non-ionic, low-osmolar compound. An exemplary composition comprises scAAV or rAAV viral particles formulated in 20 mM Tris (pH8.0), 1 mM $MgC_2$, 200 mM NaCl, 0.001% poloxamer 188 and about 25% to about 35% non-ionic, low-osmolar compound. Another exemplary composition comprises scAAV formulated in and 1×PBS and 0.001% Polyoxyethylene-polyoxypropylene block copolymer (PLURIONIC® F-68).

Dosages of rAAV to be administered in methods of the disclosure will vary depending, for example, on the particular rAAV, the mode of administration, the time of administration, the treatment goal, the individual, and the cell type(s) being targeted, and may be determined by methods standard in the art. Dosages may be expressed in units of viral genomes (vg). Dosages contemplated herein include about $1\times10^{11}$, about $1\times10^{12}$, about $1\times10^{13}$, about $1.1\times10^{13}$, about $1.2\times10^{13}$, about $1.3\times10^{13}$, about $1.5\times10^{13}$, about $2\times10^{13}$, about $2.5\times10^{13}$, about $3\times10^{13}$, about $3.4\times10^{13}$, about $3.5\times10^{13}$, about $4\times10^{13}$, about $4.5\times10^{13}$, about $5\times10^{13}$, about $6\times10^{13}$, about $1\times10^{14}$, about $1.2\times10^{14}$, about $2\times10^{14}$, about $3\times10^{14}$, about $4\times10^{14}$ about $5\times10^{14}$, about $1\times10^{15}$, to about $1\times10^{16}$, or more total viral genomes. Dosages of about $1\times10^{11}$ to about $1\times10^{15}$ vg, about $1\times10^{12}$ to about $1\times10^{15}$ vg, about $1\times10^{12}$ to about $1\times10^{14}$ vg, about $1\times10^{13}$ to about $6\times10^{14}$ vg, and about $6\times10^{13}$ to about $1.2\times10^{14}$ vg are also contemplated. One dose exemplified herein is $6\times10^{13}$ vg. Another dose exemplified herein is $1.2\times10^{14}$.

Methods of transducing target cells (including, but not limited to, cells of the nervous system, nerve or glial cells) with rAAV are provided. The cells of the nervous system include neurons, lower motor neurons, microglial cells, oligodendrocytes, astrocytes, Schwann cells or combinations thereof.

The term "transduction" is used to refer to the administration/delivery of the CLN3 polynucleotide to a target cell either in vivo or in vitro, via a replication-deficient rAAV of the disclosure resulting in expression of a functional polypeptide by the recipient cell. Transduction of cells with rAAV of the disclosure results in sustained expression of polypeptide or RNA encoded by the rAAV. The present disclosure thus provides methods of administering/delivering to a subject rAAV encoding a CLN3 polypeptide by an intrathecal, intracerebroventricular, intraparennchymal, or intravenous route, or any combination thereof. Intrathecal delivery refers to delivery into the space under the arachnoid membrane of the brain or spinal cord. In some embodiments, intrathecal administration is via intracisternal administration.

Intrathecal administration is exemplified herein. These methods include transducing target cells (including, but not limited to, nerve and/or glial cells) with one or more rAAV described herein. In some embodiments, the rAAV viral particle comprising a polynucleotide encoding a CLN3 polypeptide is administered or delivered the brain and/or spinal cord of a patient. In some embodiments, the polynucleotide is delivered to brain. Areas of the brain contemplated for delivery include, but are not limited to, the motor cortex, visual cortex, cerebellum and the brain stem. In some embodiments, the polynucleotide is delivered to the spinal cord. In some embodiments, the polynucleotide is delivered to a neuron or lower motor neuron. The polynucleotide may be delivered to nerve and glial cells. The glial cell is a microglial cell, an oligodendrocyte or an astrocyte. In some embodiments, the polynucleotide is delivered to a Schwann cell.

In some embodiments of methods provided herein, the patient is held in the Trendelenburg position (head down position) after administration of the rAAV (e.g., for about 5, about 10, about 15 or about 20 minutes). For example, the patient may be tilted in the head down position at about 1 degree to about 30 degrees, about 15 to about 30 degrees, about 30 to about 60 degrees, about 60 to about 90 degrees, or about 90 to about 180 degrees).

The methods provided herein comprise the step of administering an effective dose, or effective multiple doses, of a composition comprising a rAAV provided herein to a subject (e.g., an animal including, but not limited to, a human patient) in need thereof. If the dose is administered prior to development of CLN3-Batten Disease, the administration is prophylactic. If the dose is administered after the development of CLN3-Batten Disease, the administration is therapeutic. An effective dose is a dose that alleviates (eliminates or reduces) at least one symptom associated with the disease, that slows or prevents progression of the disease, that diminishes the extent of disease, that results in remission (partial or total) of disease, and/or that prolongs survival. In comparison to the subject before treatment or in comparison to an untreated subject, methods provided herein result in stabilization, reduced progression, or improvement in one or more of the scales that are used to evaluate progression and/or improvement in CLN3 Batten-disease, e.g. the Unified Batten Disease Rating System (UBDRS) or the Hamburg Motor and Language Scale. The UBDRS assessment scales (as described in Marshall et al., Neurology. 2005 65(2):275-279) [including the UBDRS physical assessment scale, the UBDRS seizure assessment scale, the UBDRS behavioral assessment scale, the UBDRS capability assessment scale, the UBDRS sequence of symptom onset, and the UBDRS Clinical Global Impressions (CGI)]; the Pediatric Quality of Life Scale (PEDSQOL) scale, motor function, language function, cognitive function, and survival. In comparison to the subject before treatment or in comparison to an untreated subject, methods provided herein may result in one or more of the following: reduced or slowed lysosomal accumulation of autofluorescent storage material, reduced or slowed lysosomal accumulation of ATP Synthase Subunit C, reduced or slowed glial activation (astrocytes and/or microglia) activation; reduced or slowed astrocytosis, and showed a reduction or delay in brain volume loss measured by MRI.

Combination therapies are also provided. Combination, as used herein, includes either simultaneous treatment or sequential treatment. Combinations of methods described herein with standard medical treatments are specifically contemplated. Further, combinations of compositions (e.g., a combination of scAAV9.P546.CLN3 and a contrast agent disclosed herein) for use according to the invention—either simultaneous treatment or sequential treatment—are specifically contemplated.

While delivery to a subject in need thereof after birth is contemplated, intrauterine delivery to a fetus is also contemplated.

EXAMPLES

While the following examples describe specific embodiments, it is understood that variations and modifications will occur to those skilled in the art. Accordingly, only such limitations as appear in the claims should be placed on the invention.

In the examples, a self-complementary AAV (named scAAV9.P546.CLN3) carrying a CLN3 cDNA under the control of a P546 promoter was produced. The P546 promoter is a truncated version of the MeCP2 promoter, allowing expression of the transgene in both neurons and astrocytes at moderate levels. The efficacy of this gene therapy vector was tested in the CLN3$^{\Delta ex7/8}$ knock-in mouse model, which carries the most frequent mutation found in human patients. The safety and efficacy of scAAV9.P546.CLN3 were evaluated in vivo in the CLN3$^{\Delta ex7/8}$ knock-in mouse model, wild type mice and non-human primates. Data from mice and non-human primates clearly demonstrate efficient transduction of astrocytes and neurons throughout the brain and spinal cord including deep brain structures, such as thalamus, hippocampus, striatum, amygdala, medulla and cerebellum.

Example 1

Production of scAAV9.P546.CLN3

A DNA including the open reading frame of human CLN3 (SEQ ID NO: 2) between two Not1 restriction sites was synthesized by Eurofin Genomics, USA, and then inserted in a double-stranded AAV2-ITR-based production plasmid. A schematic of the plasmid construct showing the CLN3 DNA inserted between AAV2 ITRs [the 5' ITR was modified as previously described in McCarty et al., Gene Therapy 8:1248-1254 (2001) to generate scAAV] is shown in FIG. 1. The plasmid construct also includes the P546 promoter, an SV40 chimeric intron and a Bovine Growth Hormone (BGH) polyadenylation signal.

scAAV9.P546.CLN3 was produced under cGMP conditions by transient triple-plasmid transfection procedures using the double-stranded AAV2-ITR-based production plasmid, with a plasmid encoding Rep2Cap9 sequence as previously described [Gao et al., *J. Virol.*, 78: 6381-6388 (2004)], along with an adenoviral helper plasmid pHelper (Stratagene, Santa Clara, CA) in HEK293 cells. Virus was purified by two cesium chloride density gradient purification steps, dialyzed against PBS and formulated with 0.001% Polyoxyethylene-polyoxypropylene block copolymer (PLURONIC® F-68) to prevent virus aggregation and stored at 4° C. All scAAV preparations were titered by quantitative PCR using hydrolysis probes (TAQMAN® technology). Purity of scAAV was assessed by 4-12% sodium dodecyl sulfate-acrylamide gel electrophoresis and silver staining (Invitrogen, Carlsbad, CA).

Example 2

Long-Term Efficacy Study of CSF-Delivered scAAV9.P546.CLN3 in CLN3$^{\Delta ex7/8}$ Mice Cell Targeting and Expression To confirm the expression and biodistribution of virally-introduced human CLN3 in mice, scAAV9.P546.CLN3 was formulated in 1×PBS and 0.001% Polyoxyethylene-polyoxypropylene block copolymer (PLURONIC® F-68) or formulated in 20 mM Tris (pH8.0), 1 mM MgCl2, 200 mM NaCl, 0.001%.poloxamer 188, and administered into CLN3$^{\Delta ex7/8}$ mice via intracerebroventricular (ICV) injection within 36 hours of birth and expression was monitored at various time points. Wild type and CLN3$^{\Delta ex7/8}$ mice injected with an equal volume of PBS served as controls. The effective administered dose was 2.2×10$^{10}$ vg/mouse using the NCH viral vector core titer.

Figure 2:
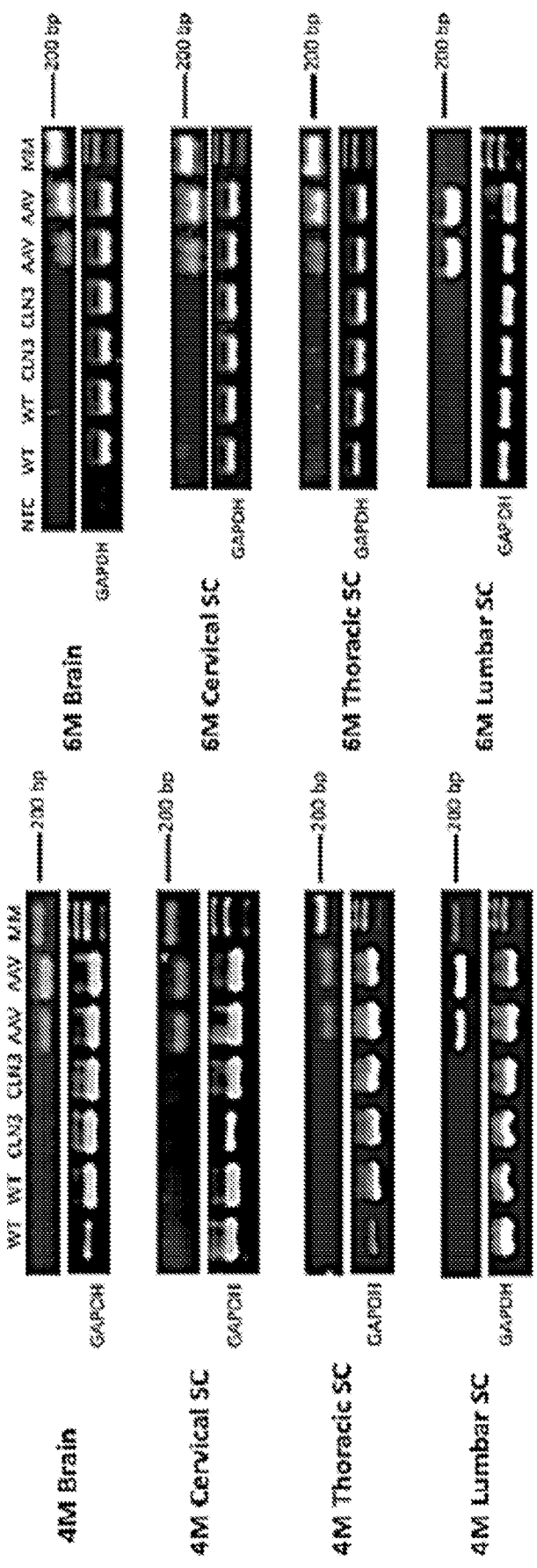
FIG. 2 provides images showing the presence of human CLN3 transcript in CLN3$^{\Delta ex7/8}$ mice injected with scAAV9.P546.CLN3.

To obtain a detailed brain biodistribution profile, in situ hybridization techniques (RNASCOPE®) were used to specifically identify human CLN3 mRNA in the brain, cervical spinal cord, thoracic spinal cord and the lumbar spinal cord. This technique involved using RNA in situ hybridization with specific probes to detect only the human transgene encoded by the scAAV9. A strong signal was observed at 4 months and 6 months post-injection, particularly in the cortex (regions A-C) of CLN3$^{\Delta ex7/8}$ mice injected with scAAV9.P546.CLN3 compared to no signal in PBS injected controls. The analysis demonstrated that the AAV9 delivered CLN3 transgene was expressed at adequate levels in various regions of the brain including cortex, thalamus, hindbrain, cerebellum and spinal cord. In the cerebellum, the signal was particularly strong in Purkinje neurons. Transgene expression was also detected in brain and all regions of the spinal cord via reverse transcription PCR at 4 and 6 months (FIG. 2).

Taken together, the reverse transcription PCR data and in situ hybridization (RNASCOPE®) analysis performed on tissue from CLN3$^{\Delta ex7/8}$ mice, confirmed that a single ICV injection of scAAV9.P546.CLN3 led to successful targeting and expression of human CLN3 throughout the brain and spinal cord up to 6 months post injection. This confirms the validity of ICV-mediated delivery of the scAAV9 to specifically target cells that are disproportionately involved in the pathogenesis of CLN3-Batten disease. The expression data in the CLN3$^{\Delta ex7/8}$ mouse model were further confirmed in studies in wild type mice using the same primers for detection of the human transgene via quantitative RT-PCR.
Pathology Improvements Following Delivery of scAAV9.P546.CLN3
Accumulation of Autofluorescent Storage Material (ASM)

Figure 3:
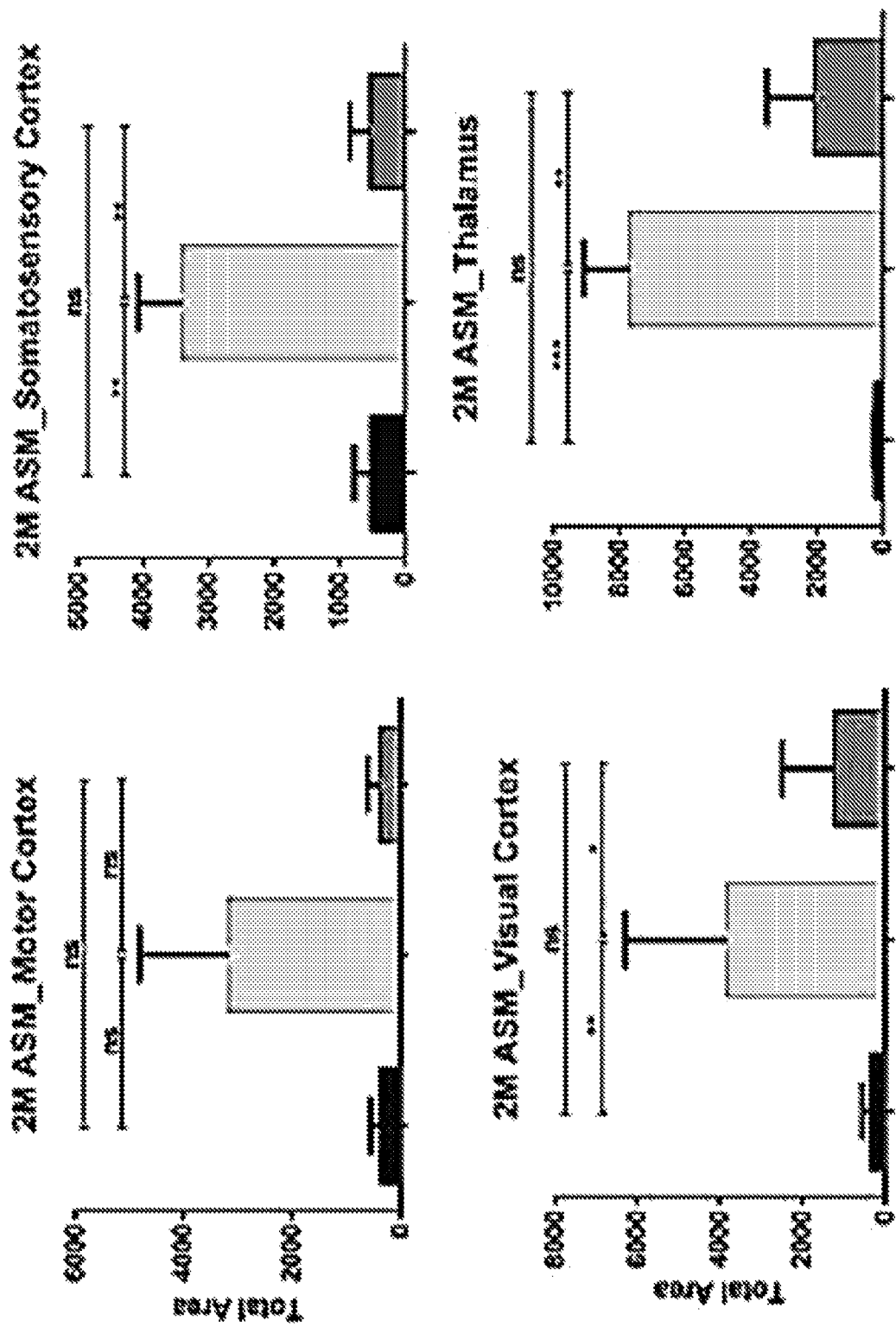
FIG. 3 provides graphs showing early reduction in ASM accumulation at 2 months post injection in CLN3$^{\Delta ex7/8}$ mice injected with scAAV9.P546.CLN3. The y-axis on all graphs shown represent total area of ASM accumulation. The black bars represent wild type mice (WT-PBS), the light gray bars represent PBS-injected CLN3$^{\Delta ex7/8}$ mice and the dark gray mice represent scAAV9.P546.CLN3-injected CLN3$^{\Delta ex7/8}$ mice.

Accumulation of autofluorescent storage material (ASM) is the hallmark histological marker for Batten disease progression (Mole et al., Biochim Biophys Acta—Mol Basis Dis. 2015; 1852(10):2237-2241; Cotman et al., Clin Lipidol. 2012 February; 7(1):79-91; Seehafer et al., Neurobiol Aging. 2006; 27:576-588). Accumulation of ASM is a strong indicator for disease progression for many forms of Batten disease (Bosch et al., J Neurosci. 2016; 36(37):9669-9682; Morgan et al., PLoS One. 2013; 8(11):e78694). It is contemplated herein that reduction of ASM is used as indicator of successful treatment. Being one of the earliest detectable disease manifestations of CLN3-Batten disease, ASM was already visible in numerous brain regions of CLN3$^{\Delta ex7/8}$ mice by 2 months of age (FIG. 3).

Figure 4:
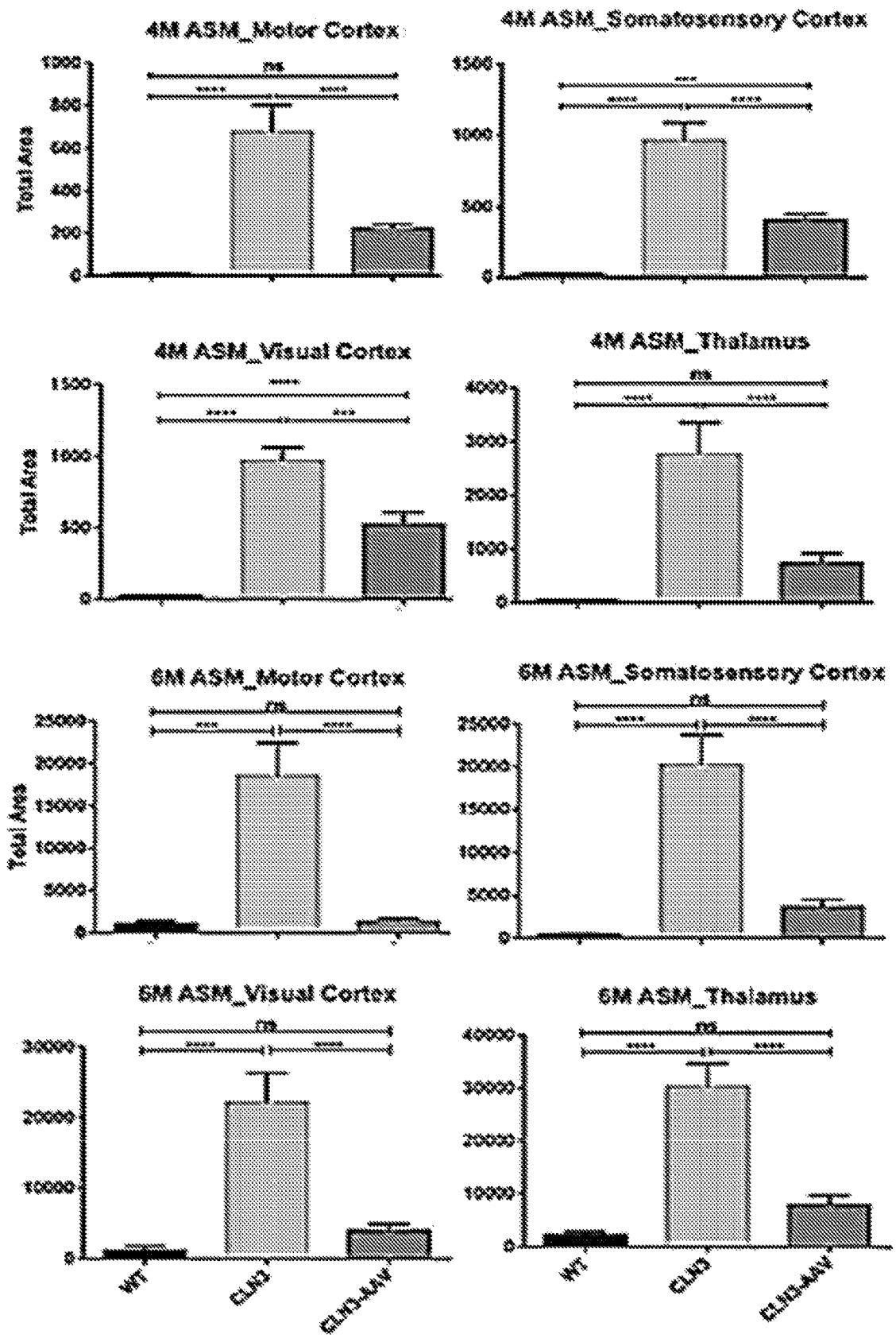
FIG. 4 provides graphs for CLN3$^{\Delta ex7/8}$ mice injected with scAAV9.P546.CLN3 show strongly reduced accumulation of ASM at 4 months and 6 months post-injection in various brain regions in PBS-injected wild type mice ("WT"), PBS-injected CLN3$^{\Delta ex7/8}$ ("CLN3"), and scAAV9.P546.CLN3-injected CLN3$^{\Delta ex7/8}$ ("CLN3-AAV").
Figure 5:
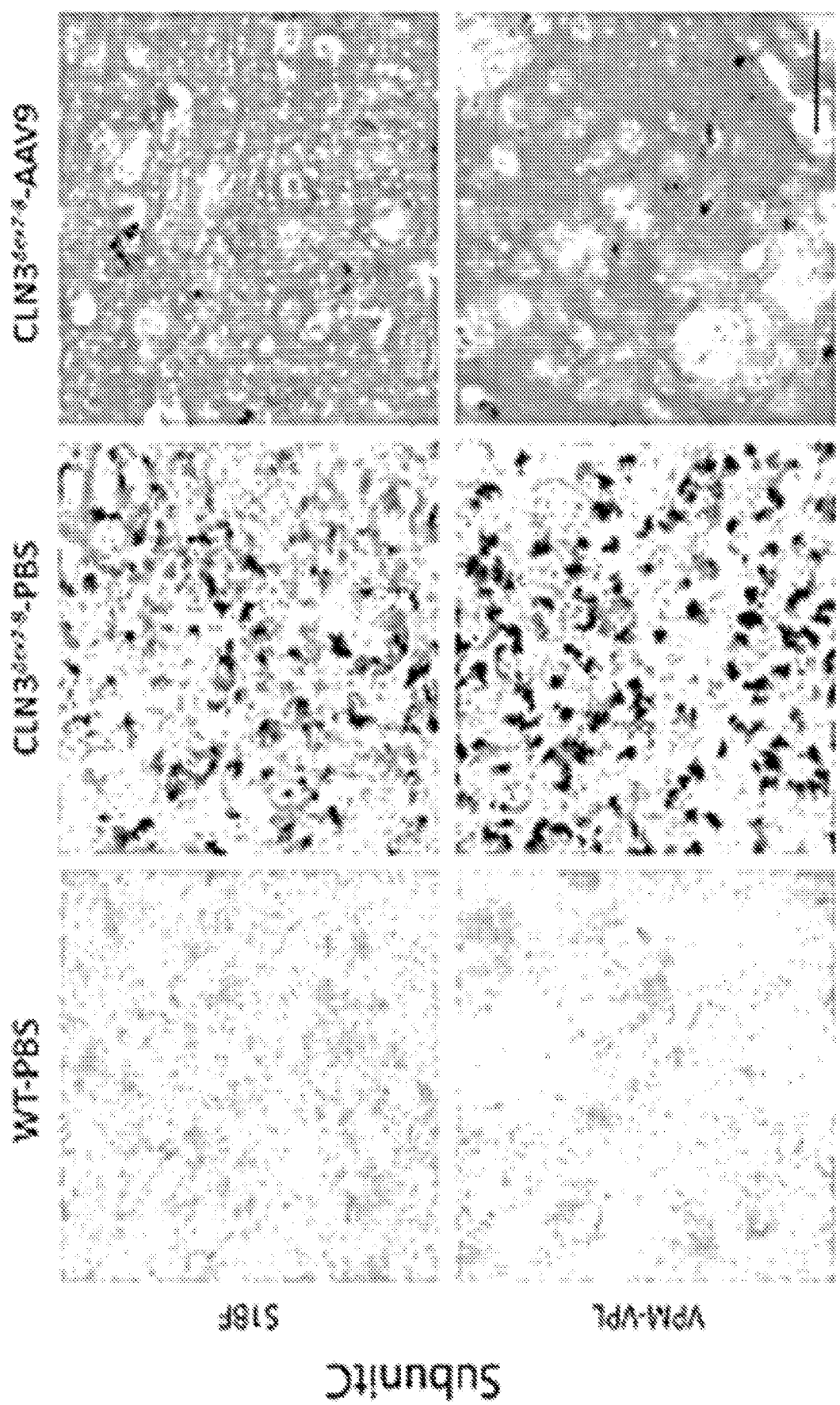
FIG. 5A-B provides images and graphs demonstrating that ICV administration of scAAV9.P546.CLN3 reduced the aberrant lysosomal accumulation of the mitochondrial protein ATP Synthase subunit C in the brains of 4 and 6 month old CLN3$^{\Delta ex7/8}$ mice. Representative images of frozen tissue sections stained for ATP synthase subunit C and visualized with DAB staining at the 6 month time point are provided in FIG. 5A. The graphs in FIG. 5B provide the quantification of subunit C accumulation in PBS-injected WT ("WT"), PBS-injected CLN3$^{\Delta ex7/8}$ ("CLN3"), and scAAV9.P546.CLN3-injected CLN3$^{\Delta ex7/8}$ ("CLN3-AAV") mice at 4 months (4M) and 6 months (6M) post-injection in the somatosensory 1 barrel field of the cortex (S1BF) at 4 and 6 months post-injection and the ventral posteromedial/ventral posterolateral nucleus (VPM/VPL). N=5, p<0.0001 between untreated CLN3$^{\Delta ex7/8}$ and scAAV9.P546.CLN3 treated animals, as well as wild type animals. p<0.5 between wild type and treated CLN3$^{\Delta ex7/8}$ mice in the SIBF at 4 and 6 months post-injection.
Figure 5:
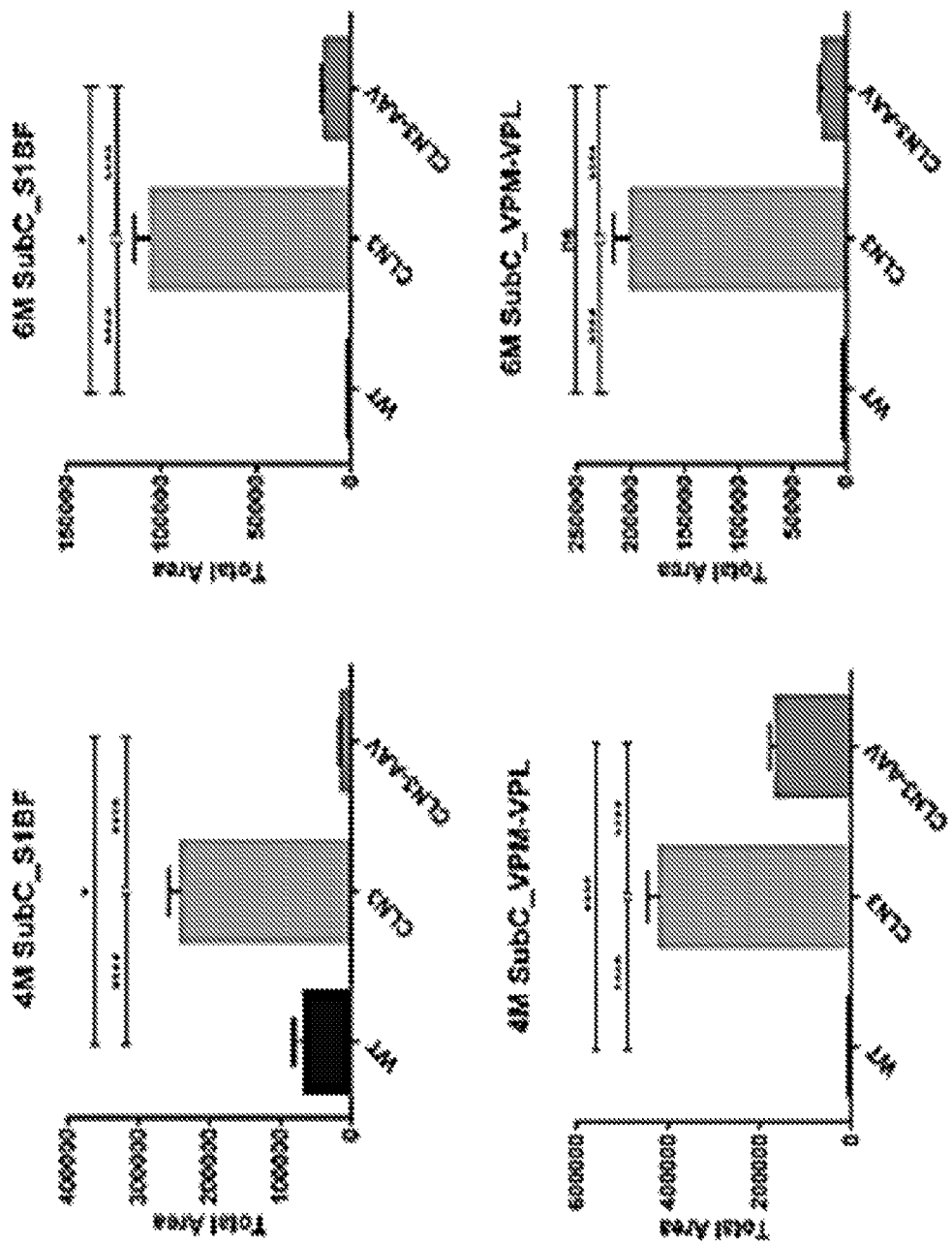

Automated quantification of fluorescent pixel area confirmed a significant reduction in accumulated ASM in the somatosensory cortex and thalamus in scAAV9.P546.CLN3-injected CLN3$^{\Delta ex7/8}$ mice at 2 months of age. Since at this early time point, higher variability of ASM accumulation in motor cortex and visual cortex were seen in PBS treated CLN3$^{\Delta ex7/8}$ mice, the statistical power of the analysis was lower for these two areas. At 4 and 6 months post injection, all four brain areas showed highly significant reduction in ASM accumulation compared to PBS treated CLN3$^{\Delta ex7/8}$ mice (FIG. 4). When comparing scAAV9.P546.CLN3-injected CLN3$^{\Delta ex7/8}$ mice to wild type animals, slightly higher ASM levels were found in the somatosensory and visual cortex of scAAV9.P546.CLN3-injected CLN3$^{\Delta ex7/8}$ mice at 4 months post injection, while no significant difference was found between wild type and scAAV9.P546.CLN3 treated CLN3$^{\Delta ex7/8}$ mice in motor cortex and thalamus. At 6 months post injection, all areas showed comparable low levels of ASM in wild type and scAAV9.P546.CLN3 treated CLN3$^{\Delta ex7/8}$ mice that were much lower compared to PBS treated CLN3$^{\Delta ex7/8}$ mice, confirming the long lasting and highly efficient reduction in ASM accumulation (p<0.0001). (N=10 per group), p<0.0001 for all but visual cortex at 4 months (p<0.001) and motor cortex (p<0.001) at 6 months post injection between PBS and scAAV9.P546.CLN3 treated animals.
Accumulation of Mitochondrial Protein ATP Synthase Subunit C Brain tissue of wild type and CLN3$^{\Delta ex7/8}$ PBS-injected or scAAV9.P546.CLN3-injected mice was analyzed for accumulation of ATP synthase subunit C. In healthy individuals, this protein is part of the respiratory chain in the mitochondrial membrane, but in patients suffering from Batten disease, the protein aberrantly accumulates in lysosomes (Palmer et al., Am J Med Genet. 1992; 42(4):561-567). In the CLN3$^{\Delta ex7/8}$ mouse, compared to wild type animals, subunit C accumulation is apparent by 4 months of age in the ventral posteromedial nucleus and ventral posterolateral nucleus of the thalamus (VPM/VPL region), a brain region often affected early on in NCL mouse models (Morgan et al., PLoS One. 2013; 8(11):e78694; Pontikis et al., Neurobiol Dis. 2005; 20(3):823-836). While untreated animals showed a strong signal for accumulated ATP synthase sub C in the somatosensory cortex and the VPM/VPL area of the thalamus, scAAV9.P546.CLN3 treated animals displayed minimal signal that was comparable to wild type animals at both, 4 and 6 months post injection (FIG. 5A-B) (p≤0.0001 between PBS and scAAV9.P546.CLN3 treated animals).
Glial and Astrocyte Activation Besides aberrant accumulation of storage material and accumulation of ATP Synthase sub C, other histological markers of disease progression in both human patients and animal models include activation of astrocytes and microglia (Cotman et al., Hum Mol Genet. 2002; 11(22):2709-2721; Morgan et al., PLoS One. 2013; 8(11):e78694; Pontikis et al., Neurobiol Dis. 2005; 20(3):823-836; Palmer et al., Am J Med Genet. 1992; 42(4):561-567). In particular, reactive microglia are primed to release pro-inflammatory mediators such as IL1-$\beta$26, which may be a key contributing cause of neuronal cell death at the later stages of CLN3-Batten disease. Activated astrocytes were identified in VPM/VPL thalamus and somatosensory cortex sections by staining for glial fibrillary acidic protein (GFAP) at 4 and 6 month timepoints. For the somatosensory cortex, quantification was performed in the barrel cortex within cortical layer IV of the somatosensory cortex. Representative images at 6 months post-injection are shown in FIG. 6A.

Figure 6:
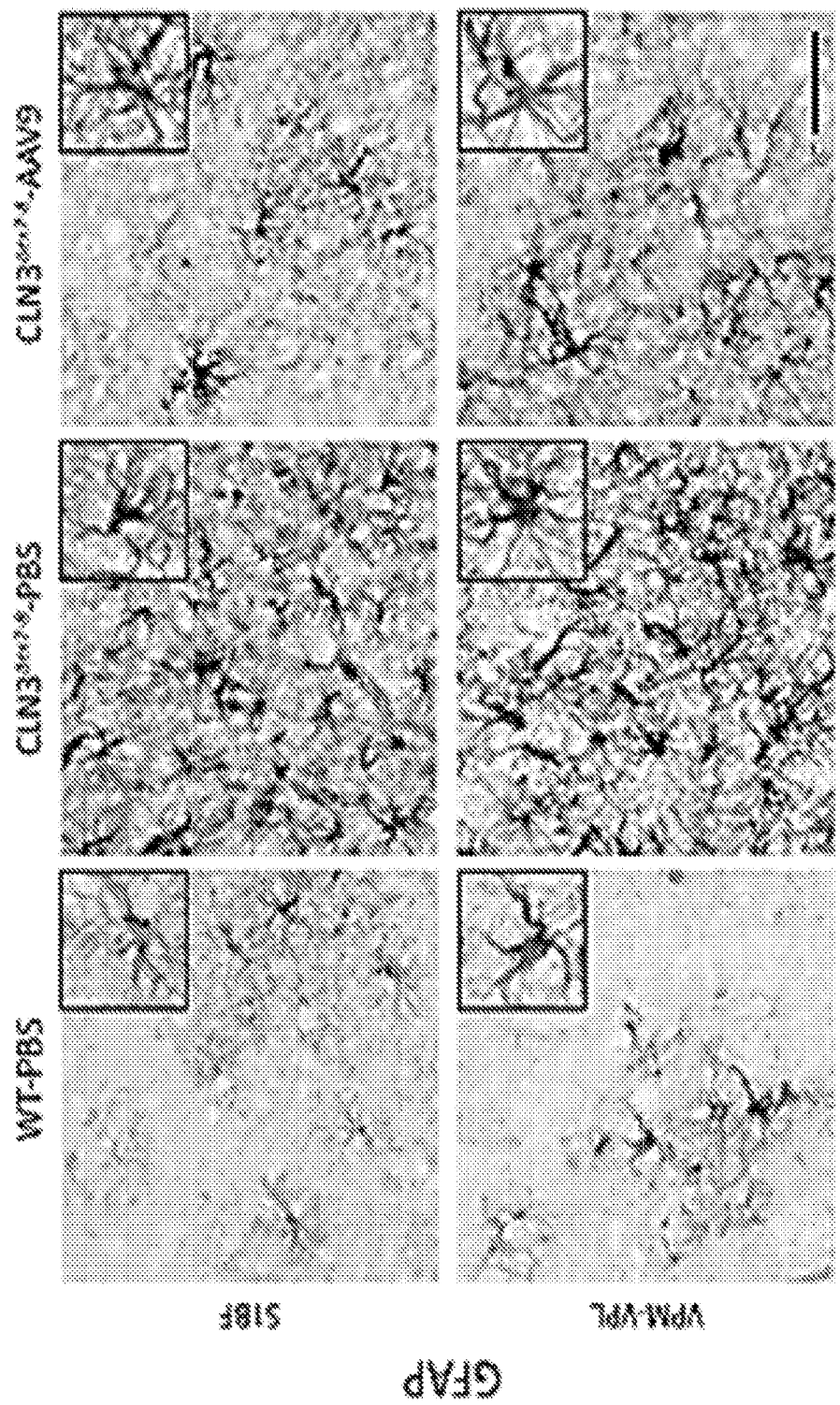
FIG. 6A-B provides images and graphs for ICV administration of scAAV9.P546.CLN3 reduced astrocytosis in the brains of 4 and 6 month old CLN3$^{\Delta ex7/8}$ mice.
Figure 6:
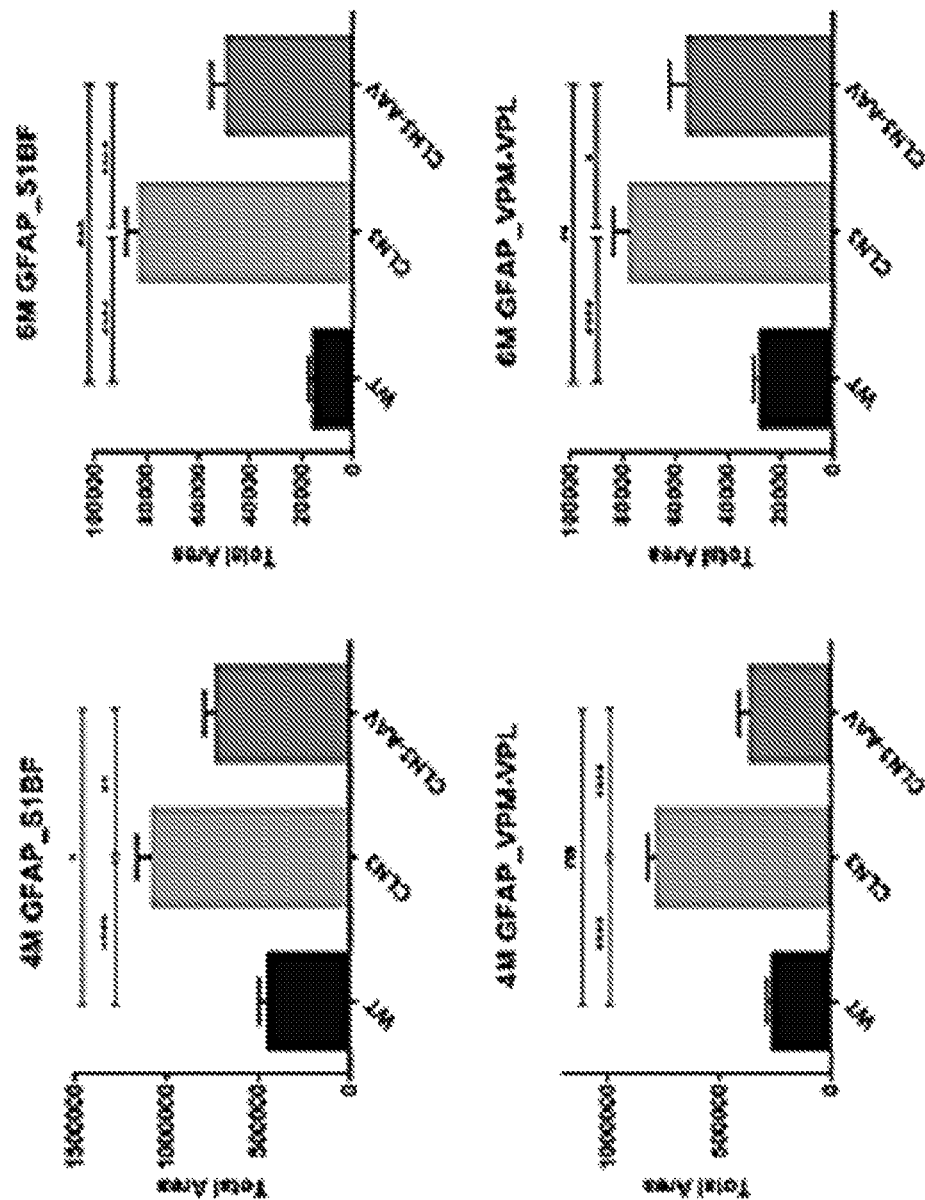

Quantification of the GFAP-positive area 4 and 6 months after treatment shows that astrocyte activation was significantly reduced in both brain regions in the scAAV9.P546.CLN3-injected CLN3$^{\Delta ex7/8}$ mice compared to PBS-injected CLN3$^{\Delta ex7/8}$ mice (FIG. 6B). Although, the level of GFAP staining in scAAV9.P546.CLN3-injected CLN3$^{\Delta ex7/8}$ mice in these brain areas was much lower compared to PBS treated CLN3$^{\Delta ex7/8}$ mice, they remained above wild type levels at both 4 and 6 months post injection for most areas analyzed.

Figure 7:
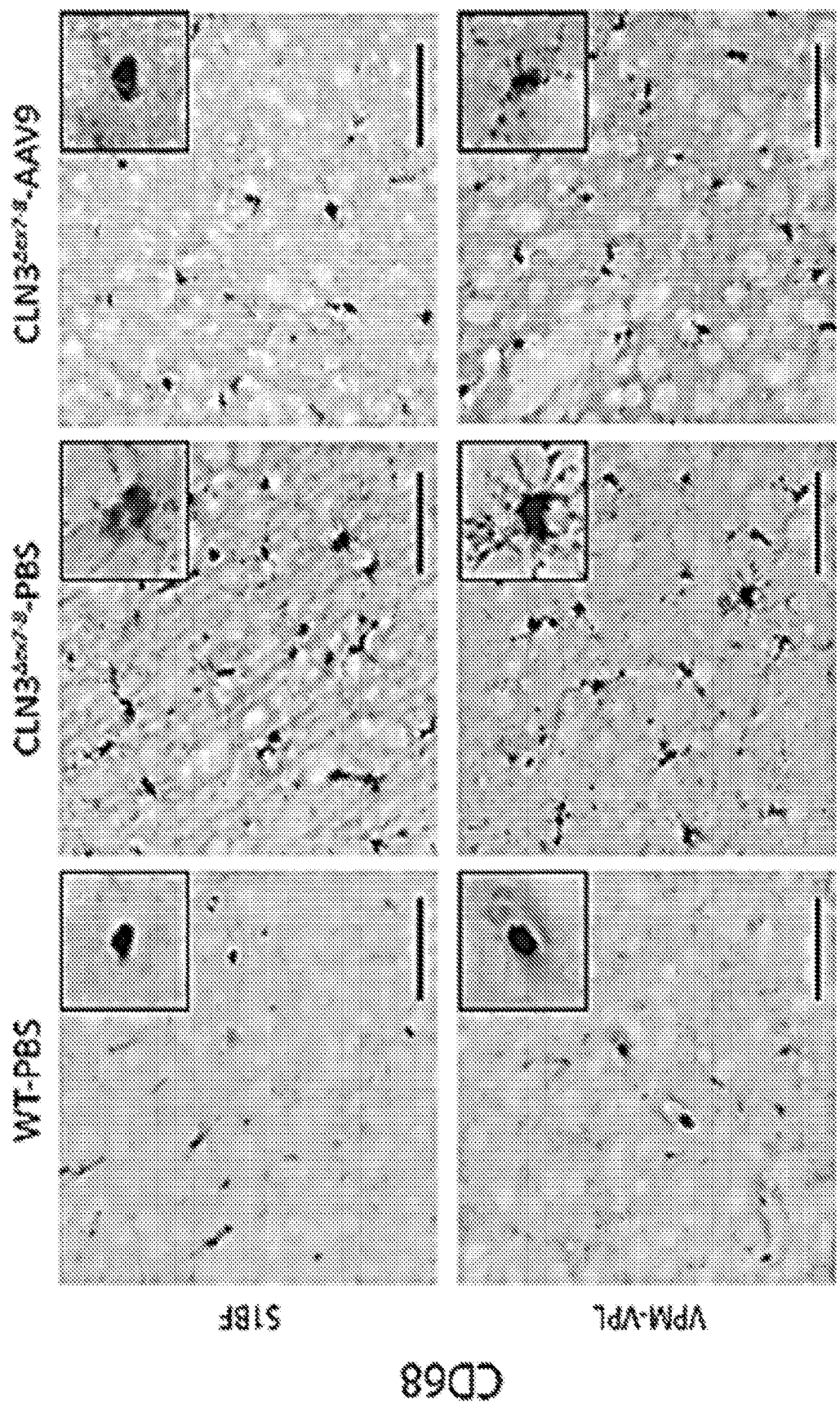
FIG. 7A-B provides images and graphs for ICV administration of scAAV9.P546.hCLN3 reduced microglia activation in the brains of 4 and 6 month old CLN3$^{\Delta ex7/8}$ mice.
Figure 7:
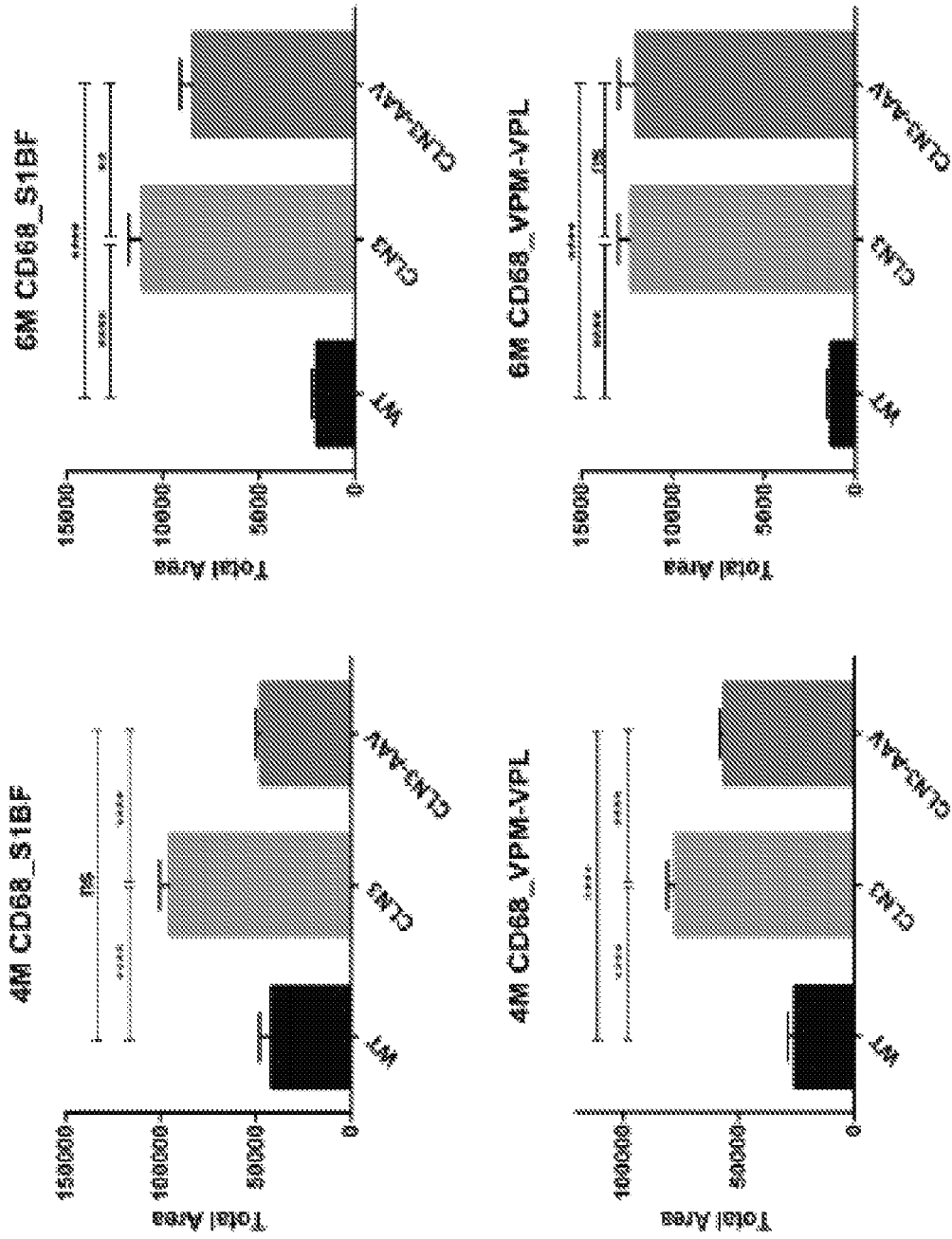

Glial activation was also determined in VPM/VPL and somatosensory cortex sections using anti-CD68 staining as a marker for activated microglia. CD68 is a lysosomal protein that is upregulated in cells primed for pro-inflammatory functions such as phagocytosis (Seehafer et al., J Neuroimmunol. 2011; 230:169-172). Similar to what was observed with astrocytes, glial activation was significantly reduced in the VPM/VPL and somatosensory cortex regions in the AAV9 injected CLN3$^{\Delta ex7/8}$ mice compared to PBS-injected CLN3$^{\Delta ex7/8}$ mice after 4 months (FIG. 7A-B). In the somatosensory cortex, treatment with scAAV9.P546.CLN3 reduced CD68 staining to a level that was comparable to wild type mice. At the 6 month time point, there was no significant improvement in the level of CD68 staining in scAAV9.P546.CLN3-treated compared to PBS-treated CLN3$^{\Delta ex7/8}$ mice in the VPM/VPL region, however, there was still a significant reduction in reactive glia in the somatosensory cortex of the scAAV9.P546.CLN3-treated mice (FIG. 7A-B).

Behavioral Improvements Following Delivery of scAAV9.P546.CLN3

In human CLN3-Batten disease patients, neurological deficits such as motor and cognitive dysfunction become apparent much later compared to earlier-onset disease variants such as CLN3-Batten disease (late-infantile Batten disease), which might be due to residual function of the truncated CLN3 protein (Kitzmuller et al., Hum Mol Genet. 2008 Jan. 15; 17(2):303-12). This delay in phenotype is also present in the CLN3$^{\Delta ex7/8}$ mouse model. In the efficacy study for scAAV9.P546.CLN3, starting at 2 months of age, and continuing at 2-month intervals, mice were subjected to a battery of behavioral testing paradigms including: accelerating rotarod assays and pole climbing to test motor function and coordination, as well as Morris water maze to assess learning and memory. Currently, animals have been followed for 10 months post-injection and studies are ongoing. Previous publications characterizing this mouse model indicate initial delay in neurodevelopmental behavior, followed by normalization and later decline starting at around 10-12 months of age (Osório et al., Genes Brain Behav. 2009 April; 8(3): 337-345).

Rotarod analysis showed no statistically significant differences between wild type and PBS or treated CLN3$^{\Delta ex7/8}$ mice up to 18 months post injection.

Figure 8:
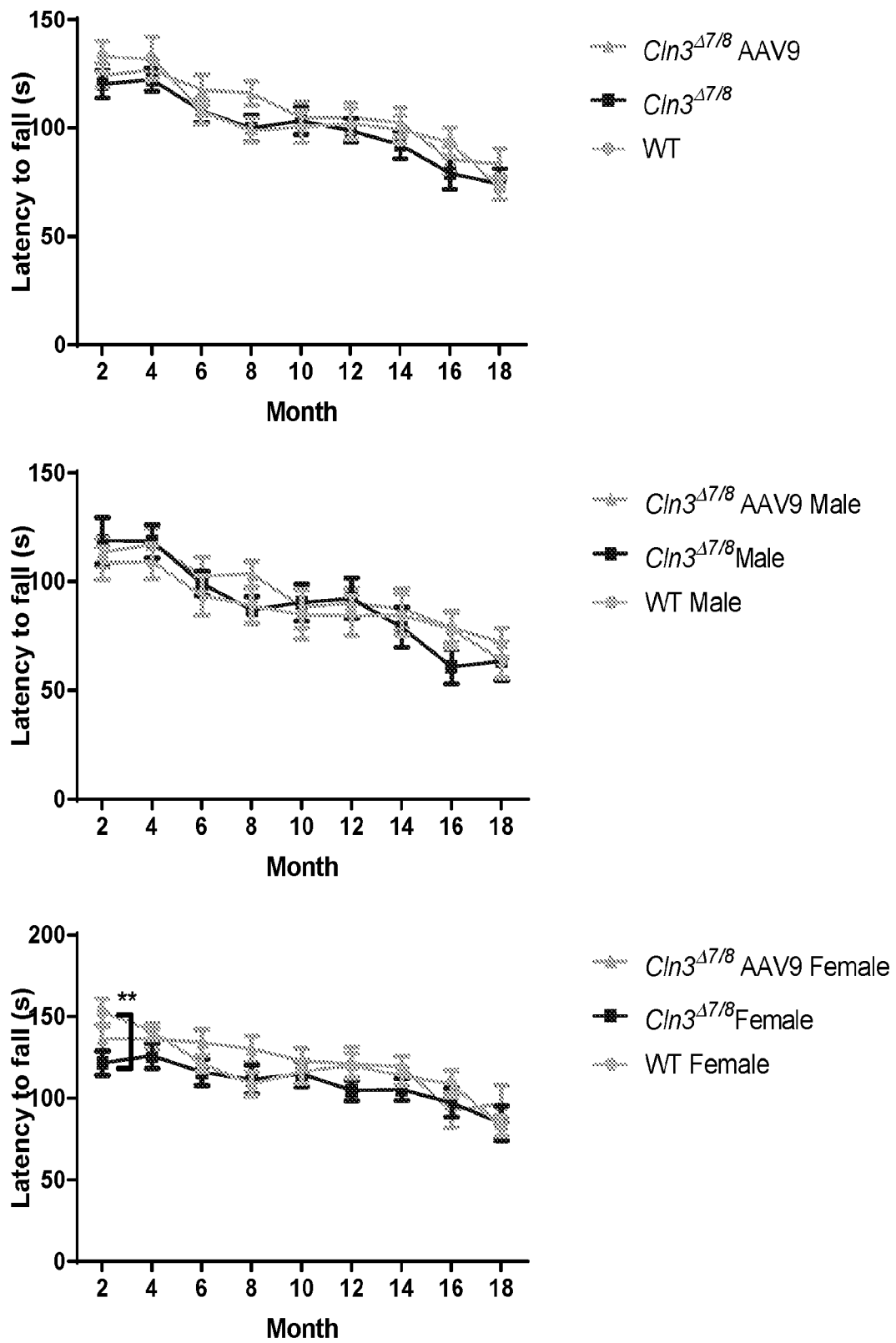
FIG. 8 provides graphs showing Rotarod analysis of wild type and PBS or treated CLN3$^{\Delta ex7/8}$ mice up to 18 months post injection. All mice both genders (top panel), male only (middle panel), female only (bottom panel).

The rotarod assay was performed every 2 months. Mice were placed on an accelerating wheel and time until they fell was measured. At each time point, mice were trained in the morning and testing was performed 4 hours later in the afternoon. Unlike previously published data, no significant difference in performance of wild type mice and PBS CLN3$^{\Delta ex7/8}$ mice up to 18 months post injection was observed (Bosch et al., J Neurosci. 2016; 36(37): 9669-9682). However, a significant difference in latency to fall was observed at 2 months post injection in female WT mice versus PBS treated CLN3$^{\Delta ex7/8}$ mice. This discrepancy compared to previous data most likely lies in the design of the testing protocol and/or environmental factors in housing. The current protocol used in this study is testing the animals only at one day at each time point, whereas previously published data repeated testing over a time span of 4 days. Moreover, the protocol used in this study was performed at a slightly lower starting speed (36 rpm vs. 40 rpm) and with a longer time interval between morning training and afternoon testing period compared to previously published data (4 hours break vs. 2 hours break). Moreover, the am training set-up was also different: while in the previous study, the mice were trained on a wheel spinning at a constant 5 rpm only in the morning for 5 min, the animals in the current study were trained using the very same settings that were then applied in the afternoon testing, which leads to acceleration of the wheel by 0.3 rpm every 2 seconds. In summary, at up to 18 months post injection, no deficits in the ability to hold on to an accelerating rotarod wheel was observed in untreated or scAAV9.P546.CLN3 treated CLN3$^{\Delta ex7/8}$ mice compared to wild type animals (FIG. 8, top panel) with the described settings.

Morris water maze analysis showed statistically significant differences between wild type and CLN3$^{\Delta ex7/8}$ mice at 2, 4, 16 and 18 months post injection.

Figure 9:
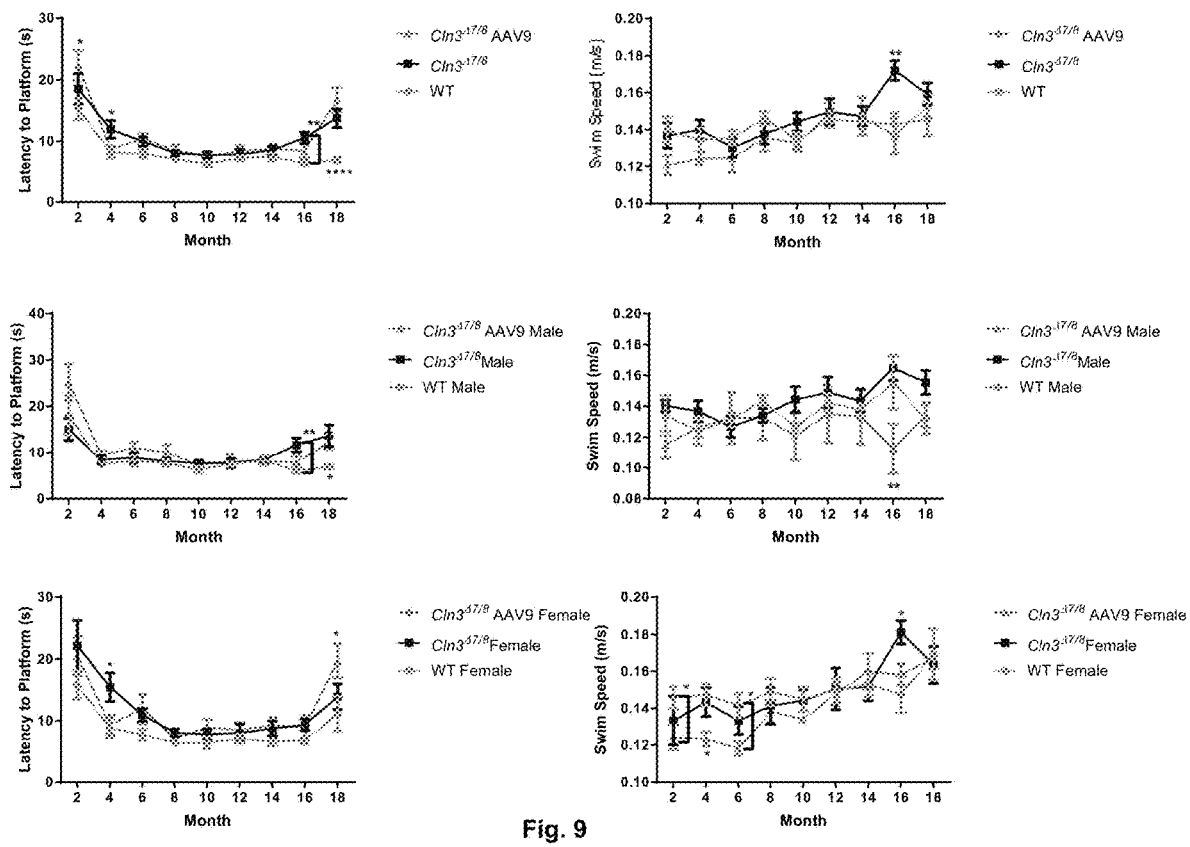
FIG. 9 provides graphs showing Morris Water Maze performance of wild type and PBS or scAAV9.P546.CLN3 treated CLN3$^{\Delta ex7/8}$ mice at up to 18 months of age. All mice (top panels), male only (middle panels), female only (bottom panels).

In the Morris Water Maze test, animals were placed in a water-filled pool containing a hidden platform. After training, the time it took the animals to find the hidden platform using environmental cues for orientation was measured as a sign of learning and memory capabilities. At 2 and 4 months post injection, statistical differences were observed between wild type animals and PBS or scAAV9.P546.CLN3 treated CLN3$^{\Delta ex7/8}$ mice, indicating that at this time point of the disease, the learning and memory was impaired to be measurable by this test resulting in a latency for the animals to find the hidden platform. Furthermore, more significant statistical differences in latency were observed between wild type and PBS or scAAV9.P546.CLN3 treated CLN3$^{\Delta ex7/8}$ mice at 16 and 18 months (FIG. 9, top left panel). The increased latency at 16 months also correlated with increased swim speed for the PBS treated CLN3$^{\Delta ex7/8}$ mice (FIG. 9, top right panel). In addition, when separated by gender, statistical differences in latency were observed between male wild type animals and scAAV9.P546.CLN3 treated CLN3$^{\Delta ex7/8}$ mice at 16 and 18 months (FIG. 9, middle left panel), while the scAAV9.P546.CLN3 treated CLN3$^{\Delta ex7/8}$ male mice swim speed significantly decreased at 16 months (FIG. 9, middle right panel). The scAAV9.P546.CLN3 treated female CLN3$^{\Delta ex7/8}$ mice showed significant increased latency compared to wildtype or PBS treated CLN3$^{\Delta ex7/8}$ animals at 18 months (FIG. 9, bottom left panel), while the PBS treated CLN3$^{\Delta ex7/8}$ male mice swim speed was significantly increased at 16 months (FIG. 9, bottom right panel).

Pole climbing assay showed improved performance of scAAV9.P546.CLN3 treated CLN3$^{\Delta ex7/8}$ compared to PBS injected animals.

The pole climbing test measures the time the mice take to turn around on a vertical pole when placed on it facing upwards, as well as the time to descend the pole when placed on it facing downwards. Moreover, the number of falls from the pole while attempting to turn or descend is also sometimes measured. This test evaluates coordination and balancing capabilities.

Figure 10:
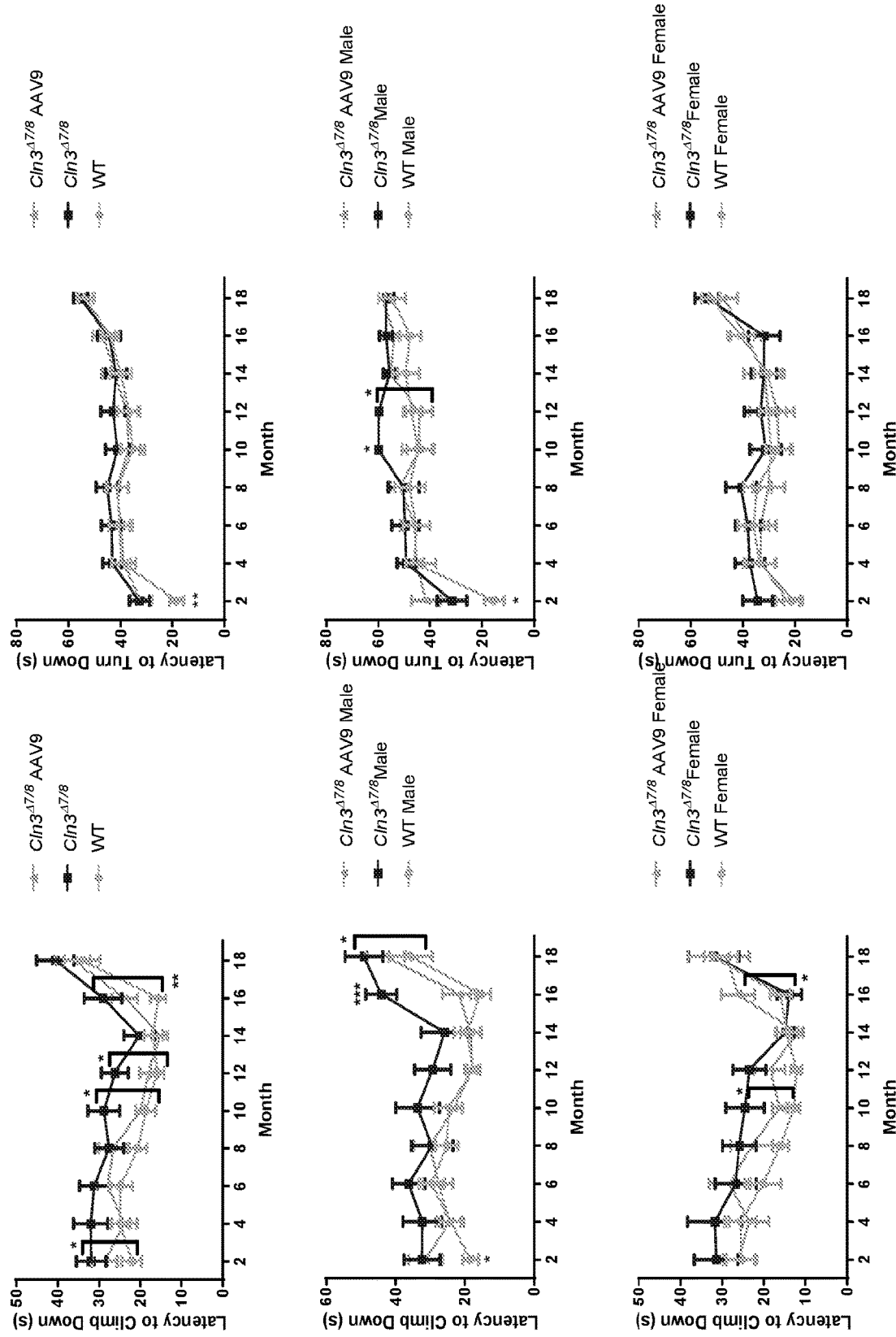
FIG. 10 provides graphs showing performance of scAAV9.P546.CLN3-treated CLN3$^{\Delta ex7/8}$ mice and PBS-treated mice in the pole climbing assay. The pole climbing assay in which mice are place face up on a vertical pole and time for them to turn and descend along with number of falls measures balance and agility. All mice (top panels), male only (middle panels), female only (bottom panels).

At 10 and 12 months post injection, scAAV9.P546.CLN3 animals were significantly faster in descending the pole compared to PBS treated animals (FIG. 10, top left panel). Statistically significant differences were seen in the time it took PBS treated CLN3$^{\Delta ex7/8}$ animals to descend a pole at 10 and 12 months post injection, while wild type and scAAV9.P546.CLN3 treated CLN3$^{\Delta ex7/8}$ were indistinguishable (FIG. 10, top left panel). Regarding the time it took the animals to turn from a facing upwards position to facing downwards, two statistically significant differences were found. At 2 and 16 months of age, wild type animals turned significantly faster compared to both scAAV9.P546.CLN3 and PBS treated CLN3$^{\Delta ex7/8}$ mice. This difference was more pronounced in male mice (FIG. 10, middle left panel) compared to females (FIG. 10, bottom left panel) where no difference compared to wild type was seen. The 2 and 16 month time points were the only time points in which differences in this parameter were observed between study groups (FIG. 10, top left panel).

Figure 11:
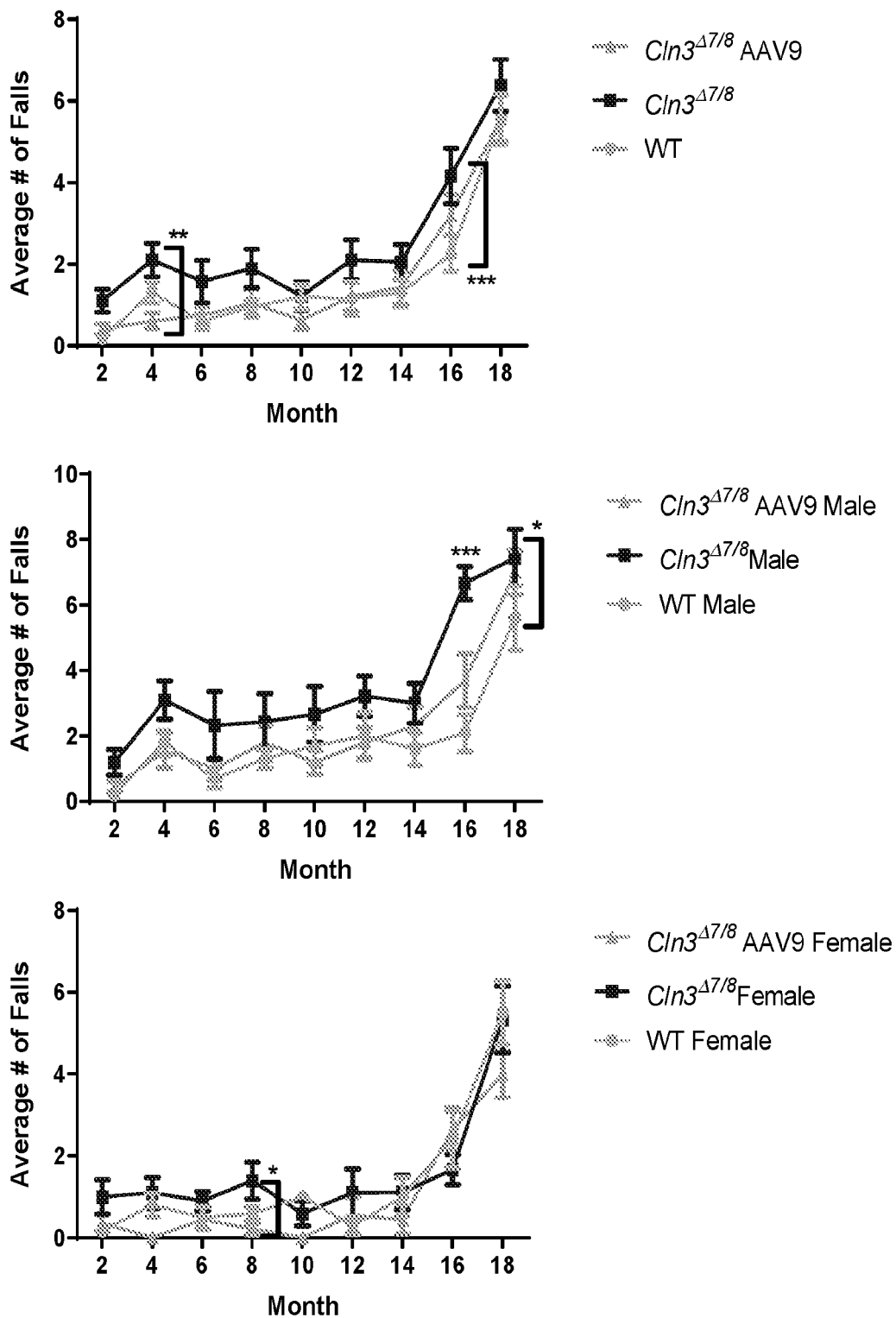
FIG. 11 provides graphs showing scAAV9.P546.CLN3-treated CLN3$^{\Delta ex7/8}$ mice fall less often from vertical poles compared to PBS-treated CLN3$^{\Delta ex7/8}$ mice. Mice are place face up on a vertical pole and number of falls measures while attempting to turn around are measured for balance and agility. All mice (top panel), male only (middle panel), female only (bottom panel).

Additional statistically significant differences were seen in the average number of falls from the pole, where PBS treated CLN3$^{\Delta ex7/8}$ males and females fell off more frequently compared to wild type and scAAV9.P546.CLN3 treated animals (FIG. 11). Top graph: Significant differences were found in month 2 in the number of falls between scAAV9.P546.CLN3 treated animals and PBS treated animals. A statistically significant difference was also observed between the wildtype and PBS treated CLN3$^{\Delta ex7/8}$ mice at 16 months post injection. Middle graph: males only. PBS treated CLN3$^{\Delta ex7/8}$ mice fell more often from the pole than other treatment groups, with the greatest statistical significance at 16 months post injection. Bottom graph: Differences in falls were significant at 8 months post injection for females, but the trend was visible during the whole study. N=5 for each treatment group (5M/5F). Interestingly, differences in falls from the pole were seen during the whole 18 months and were statistically significant at an early time point (4 months) as well as at 8 months and 16 months. At 8 months, the difference was statistically significant only in females, but a clear trend existed also in males and was statistically significant in the males at 16 months post injection. In general, PBS treated CLN3$^{\Delta ex7/8}$ males were falling off the pole more frequently than other treatment groups.

In summary, there is strong evidence that treatment of CLN3$^{\Delta ex7/8}$ mice with scAAV9.P546.CLN3 prevents the accumulation of ASM material, as well as ATP synthase subunit C, both major hallmarks of CLN3-Batten disease progression. These data correlate with a strong reduction in glial activation (astrocytes and microglia). Although early in the disease course, first trends towards improvement of behavioral phenotypes are becoming evident: scAAV9.P546.CLN3 treated CLN3$^{\Delta ex7/8}$ mice were more capable of descending a vertical pole compared to PBS treated animals as they moved faster and fell off less often. Altogether, these data support scAAV9.P546.CLN3 gene therapy as a therapeutic strategy for this disease.

Example 3

Expression Studies with scAAV9.P546.GFP in Mice

The P546 promoter allows expression of transgenes throughout the CNS in a similar manner as the chicken-beta-actin (CBA) promoter. To do a side-by-side comparison between the two promoters, at post-natal day 1, mice were injected with either scAAV9.CB.GFP or scAAV9.P546.GFP formulated in 1×PBS and 0.001% Polyoxyethylene-polyoxypropylene block copolymer (PLURIONIC® F-68) or 20 mM Tris (pH8.0), 1 mM MgCl2, 200 mM NaCl, 0.001%.poloxamer 188 at 5×10$^{10}$ viral genomes per animal. After 3 weeks, the animals were sacrificed and the brains were put directly under a fluorescent dissection microscope. From the fluorescent images, it was evident that the GFP distribution was similar, but the level of fluorescence was lower in the animal that received the scAAV9.P546.GFP compared to the one that received scAAV9.CB.GFP, confirming that the P546 promoter led to a more moderate expression level of the transgene compared to the CBA promoter.

Another mouse was injected with scAAV9.P546.GFP and kept alive for 200 days. After 200 days, the animal was sacrificed and whole-brain saggital sections were stained for GFP expression. Even 200 days post injection, widespread expression of the GFP transgene was observed throughout the entire brain including Cortex, Hippocampus, Midbrain, Medulla, Amygdala and Cerebellum, further indicating that the P546 promoter is a good candidate for CNS gene therapy.

The data from GFP fluorescence and GFP immunofluorescence staining was further supported by western blot data from various tissues and brain areas. GFP expression was readily detectable three weeks post injection with fluorescent western blot technique using an imaging system (such as the LI-COR® System) in mice that were treated with scAAV9.P546.GFP (n=3) while no band was detected in a PBS injected animal that was used as control (n=1). Transgene expression was evident in whole brain lysates, as well as region specific lysates including cortex, medulla, midbrain, hippocampus, cerebellum and spinal cord.

Figure 12:
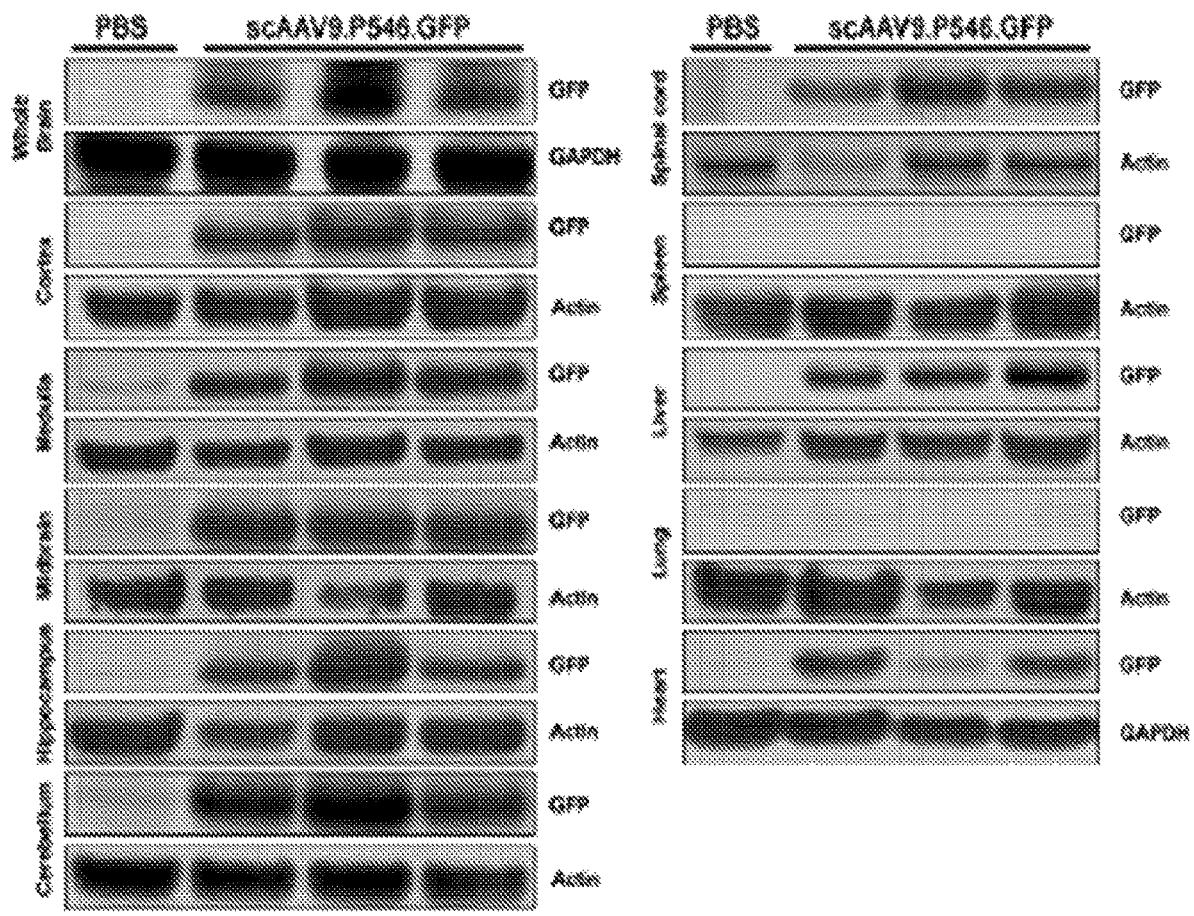
FIG. 12 provides images showing immunofluorescent western blot detection of GFP protein in various brain regions as well as peripheral mouse tissues three weeks post injection with scAAV9.P546.GFP.

Moreover, GFP expression was also confirmed in heart and liver, while lung and spleen showed little to no transcript expression (FIG. 12). The western blot data with scAAV9.P546.GFP is consistent with the expression data from the mouse and nonhuman primate safety studies, where a very similar expression profile was found. Moreover, this expression pattern in brain and peripheral organs is comparable to the pattern found with scAAV9.CB.GFP.

In summary, extensive expression analysis in mice using immunostaining and western blot techniques indicates that the P546 promoter leads to a very similar and long-lasting expression profile throughout the nervous system while allowing a more moderate expression level compared to the strong CBA promoter.

Example 4

Expression Studies with scAAV9.P546.CLN3 in Non-Human Primates

A single dose of 3.4×10$^{13}$ vg scAAV9.P546.CLN3 was in 1×PBS and 0.001% Polyoxyethylene-polyoxypropylene block copolymer (PLURIONIC® F-68) and administered into three 3-4 year old cynomolgus macaques.

Figure 13:
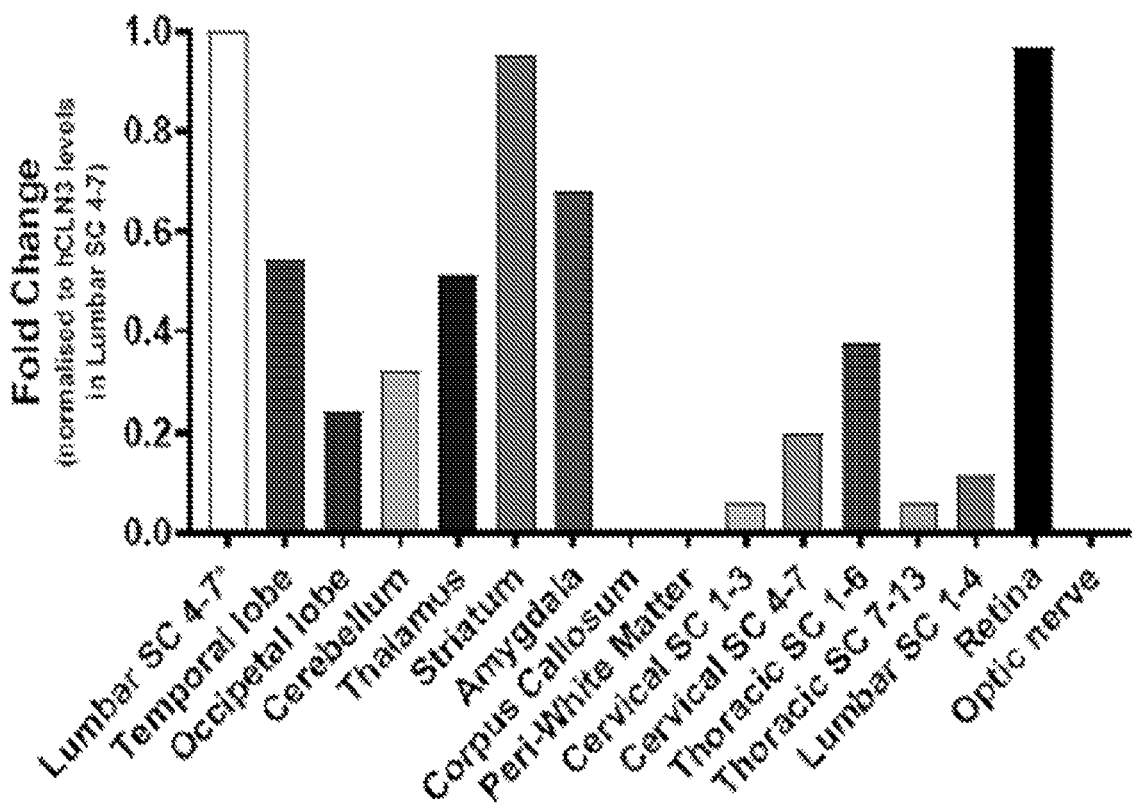
FIG. 13 provides a graph showing reverse transcription quantitative PCR of expression of human CLN3 in various brain regions of a four-year old cynomolgus macaques 12 weeks post intrathecal lumbar injection of 3×10$^{13}$ vg scAAV9.P546.CLN3. The values were normalized to the level of CLN3 protein in the lumbar spinal cord 4-7.

For the targeting analysis in brain tissue of the cynomolgus macaques that were injected with scAAV9.P546.CLN3, the targeting was analyzed on the RNA level using primers that are specific for the human CLN3 transgene and do not cross-react with the endogenous non-human primate CLN3 RNA. Reverse transcription quantitative PCR in tissue from various brain regions of one of the cynomolgus macaques that was sacrificed 12 weeks post injection revealed expression of human CLN3 in all levels of the spinal cord, cortex, thalamus, striatum, cerebellum and retina, further underlining the widespread reach of scAAV9 and the expression of the transcript throughout the brain and spinal cord with the P546 promoter (FIG. 13). Of note, the primers used for the detection of vector-derived human CLN3 do not cross-react with the endogenous NHP CLN3 transcript. Thus, the normalization was performed against the vector-derived CLN3 RNA levels found in the lumbar spinal cord which was set to 1 rather than to saline-injected or uninjected animals as a normalization to zero was not possible. Actin was used as a normalizing gene.

In summary, the data from non-human primates prove the high potential of scAAV9 to travel through the nervous system and reach large regions of the CNS after a single intrathecal lumbar injection. Of note, all non-human primates treated via intrathecal injection of scAAV9.P546.CLN3 tolerated the treatment well and no adverse effects were observed in any of the animals at any time point up to 6 months post injection.

Example 5

Clinical Trial of scAAV9.P546.CLN3 Gene Therapy

The scAAV9.P546.CLN3 will be delivered intrathecally to human patients with CLN3-Batten Disease.

The scAAV for the clinical trial is produced by the Nationwide Children's Hospital Clinical Manufacturing Facility utilizing a triple-transfection method of HEK293 cells, under cGMP conditions as described in Example 1.

Patients selected for participation will be 3-10 years of age with a diagnosis of CLN3 disease as determined by genotype. The first cohort (n=3) will receive a one-time gene transfer dose of $6 \times 10^{13}$ vg total scAAV per patient. The scAAV9.P546.CLN3 is formulated in 20 mM 1 mM $MgCl_2$, 200 mM NaCl, 0.001%. poloxamer 188 Tris (pH8.0), and will be delivered one-time through an intrathecal catheter inserted by a lumbar puncture into the interspinous into the subarachnoid space of the lumbar thecal sac. Safety will be assessed on clinical grounds, and by examination of safety labels. There will be a minimum of four weeks between enrollments of each subject to allow for review of Day 30 post-gene transfer safety data. If there are no safety concerns, after the third subject is evaluated at one month post-injection, a second cohort of four additional subjects will be enrolled. Each subject in cohort 2 (n=4) will receive an escalated dose of $1.2 \times 10^{14}$ vg total scAAV. There will be at least a six week window between the completion of Cohort 1 and the start of Cohort 2, to allow review of the safety analysis from five time points (days 1, 2, 7, 14, and 21) as well as DSMB review prior to dosing of the next subject.

Disease progression will be measured with the UBDRS scales (referenced in the Detailed Description above) and the impact of treatment on quality of life using the Pediatric Quality of Life (PEDSQOL) scale, and potential for prolonged survival.

The primary analysis for efficacy will be assessed when all patients have completed the three-year study. Basis of determining efficacy will be by stabilization or reduced progression of the disease based on the well-established Unified Batten Disease Rating Scale (UBDRS) that was developed specifically for CLN3-Batten Disease. Upon completion of the three-year study period patients will be monitored annually for 5 years as per FDA guidance.

Example 6

Additional Studies in $Cln3^{\Delta 7/8}$ Mice Model

As described in Example, 2 Wild type (WT) and $Cln3\Delta7/8$ mice were dosed with either PBS, scAAV9.p546.CLN3, or scAAV9.CB.CLN3 gene therapy via intracerebroventricular (ICV) injection at postnatal day 1. In this study, the mice were administered $5 \times 1010$ vg/animal (4 µL volume).

The injection method and timing was selected to target specific neuronal populations that are relevant in CLN3-Batten disease patients. Animals were sedated via hypothermia during the procedure, monitored until fully recovered, and genotyped as previously described (see Morgan et al. *PLoS One* 8; and Laboratory, TJ Protocol 18257: Standard PCR Assay).

Statistical analyses were performed using scientific graphing and statistics software GraphPad Prism) and details are noted in the figure legends. In general, two-way ANOVA was employed with appropriate post-hoc test, and outliers were removed with the ROUT method, Q=0.1-1%. If appropriate, an unpaired t-test was used.

Expression and Distribution of hCLN3 Transcript in the Brain

Quantitative PCR was carried out to measure hCLN3 transcript in the brains of the treated mice. Total RNA and cDNA was generated as described previously (see Cain et al. *Mol Ther.*, 2019). The 2^-Delta-Delta Ct method was used to calculate relative gene expression of the human CLN3 transcript normalized to Gapdh as the housekeeping control.

```
hCLN3 Forward primer sequence:
                                 (SEQ ID NO: 11)
CGCTAGCATCTCATCAGGCCTTG;

hCLN3 Reverse primer sequence:
                                 (SEQ ID NO: 12)
AGCATGGACAGCAGGGTCTG.
```

Figure 16:
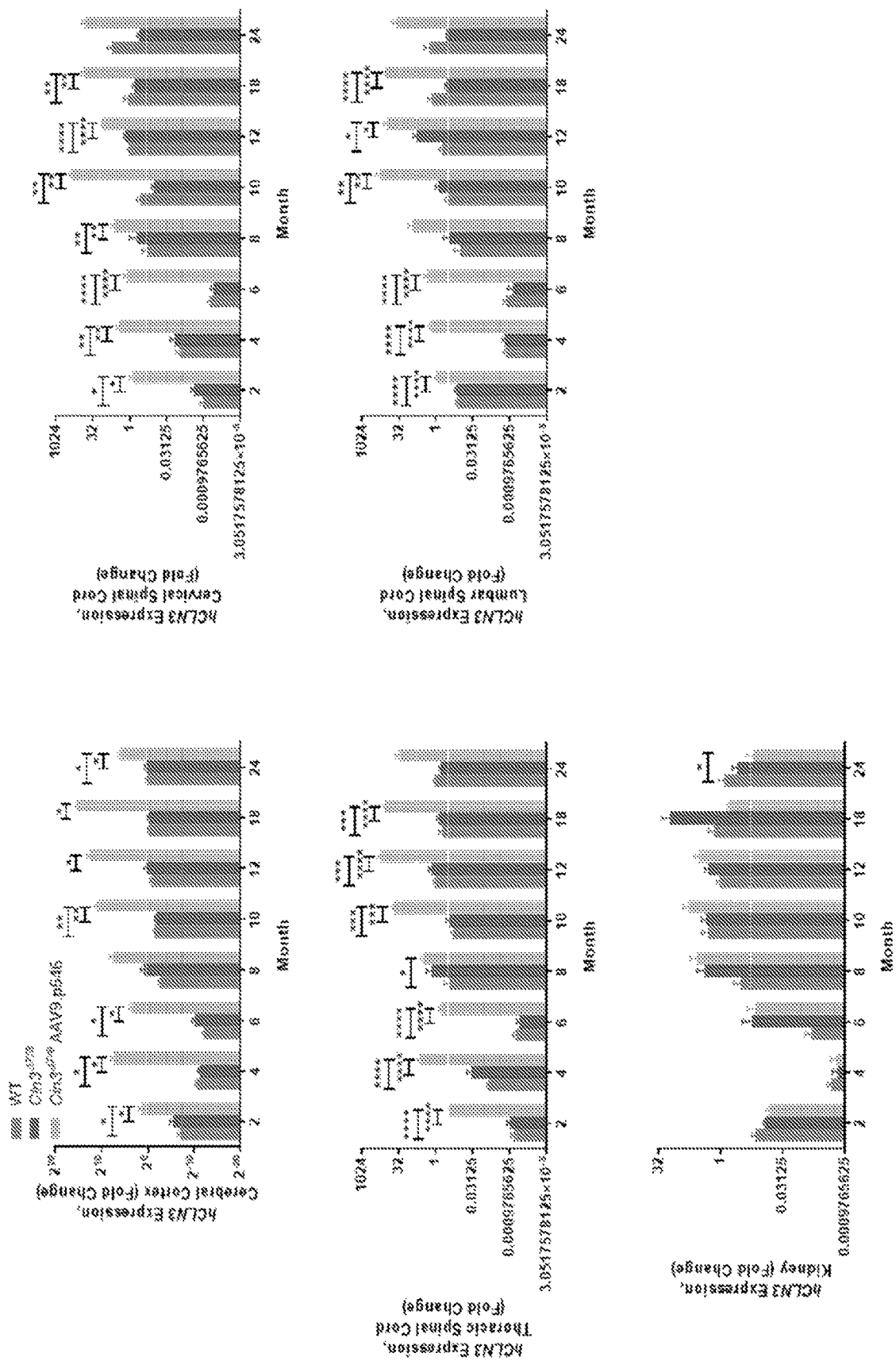
FIG. 16 provides data demonstrating that scAAV9.p546.CLN3 treatment results in increased levels of hCLN3 transcript expression in the cerebral cortex and spinal cord of Cln3$^{\Delta 7/8}$ mice as measured by qPCR up to 24 months of age. Mean±SEM, ordinary one-way ANOVA at each month, *p<0.05, p<0.01, *p<0.001, ****p<0.0001

As shown in FIG. 16, scAAV9.p546.CLN3 treatment resulted in increased levels of hCLN3 transcript expression in the cerebral cortex and spinal cord of $Cln3^{\Delta 7/8}$ mice as measured by qPCR up to 24 months of age. Thus, a single, neonatal, ICV administration of scAAV9.p546.CLN3 results in sustained and well-targeted expression of hCLN3.

In addition, in situ hybridization (RNASCOPE®) was carried out to detect CLN3 transcript in the brain of the treated mice. Mice were $CO_2$ euthanized and cardiac perfused with PBS. Brains were collected and placed on a 1 mm sagittal brain block. Brains were sliced at the midline and 3 mm right of the midline. The 3 mm sagittal piece was flash frozen with −50° C. isopentane and then sectioned on a cryostat at 16 µm and placed on slides. Slides were then processed according to the manufacturer suggested protocols (ACDBio manuals 320293 and 320513). Sections were labeled with a human specific CLN3 probe (ACDBio Cat No 470241), which consisted of 20 double Z pairs in regions of the CLN3 gene with little homology between mouse and human CLN3 (region 631-1711). Slides were fluorescently labeled with an in situ hybridization kit (RNASCOPE® Fluorescent Multiplex Kit, ACDBio Catalog no 320850) using their Amp 4-FL-AltC which tagged the hCLN3 probe with a 550 nm fluorophore, slides were counterstained with DAPI to label nuclei. Tissue sections were mounted on slides under coverslips using antifade mounting media (Dako faramount, Agilent). Slides were stored in the dark before imaging. Sections were imaged and analyzed using a microscope (Nikon NiE microscope with NIS-Elements Advanced Research software (v 4.20)).

Figure 17:
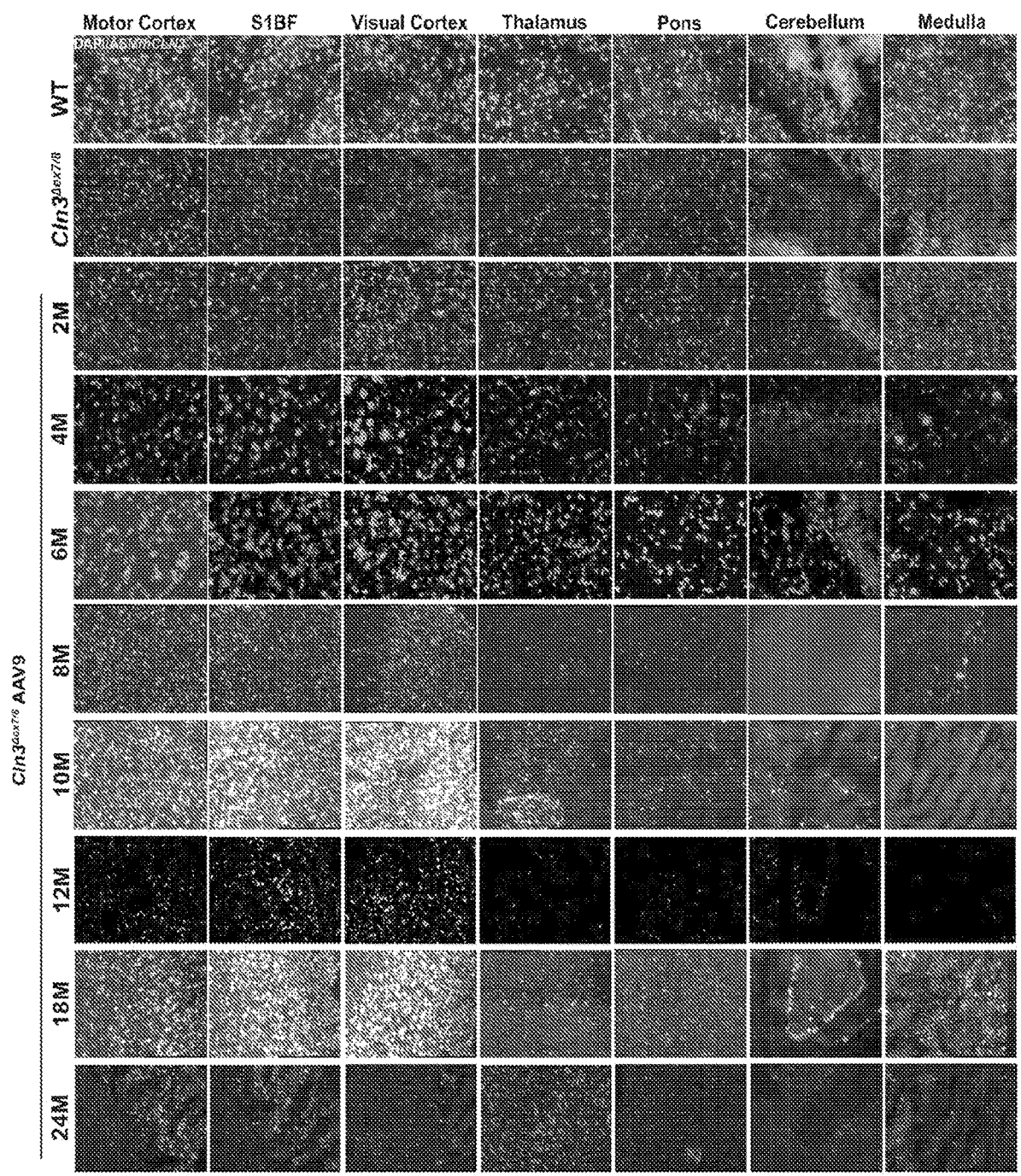
FIG. 17 provides images showing that scAAV9.p546.CLN3 treatment produces stable hCLN3 transcript throughout the brain of Cln3$^{Δ7/8}$ mice as measured by in situ hybridization (RNASCOPE®) (red fluorescence), up to 24 months of age. Images taken at 20×.

As shown in FIG. 17, scAAV9.p546.CLN3 treatment produces stable hCLN3 transcript throughout the brain of Cln3$^{\Delta 7/8}$ mice as measured by in situ hybridization (RNA-SCOPE®) (red fluorescence), up to 24 months of age. The quantitative PCT and the in situ hybridization (RNAS-COPE®) assays confirm a single, neonatal, ICV administration of scAAV9.p546. results in sustained and well-targeted expression of hCLN3. scAAV9.p546.CLN3 gene therapy increases hCLN3 gene expression throughout the brain and spinal cord up to 24 months of age.

Classic Batten Disease Pathologies

To determine if administration of scAAV9.p546.CLN3 prevented classic Batten disease pathologies in the brains of Cln3$^{\Delta 7/8}$ mice, storage material accumulation (ASM) and glial reactivity were examined after ICV administration. Wild type and Cln3$^{\Delta 7/8}$ mice were $CO_2$ euthanized, perfused with PBS, and tissue was fixed with 4% PFA. Fixed brains were sectioned on a vibratome at 50 µm (Leica VT10008). Sections were processed with standard immunofluorescence and DAB staining protocols. Primary antibodies included anti-CD68 (AbD Serotec, MCA1957; 1:2000), anti-GFAP (Dako, Z0334; 1:8000), and anti-ATP synthase subunit C (Abcam, ab181243, 1:1000). Secondary antibodies included anti-rat and anti-rabbit biotinylated (Vector Labs, BA-9400; 1:2000). Sections were imaged and analyzed using a Slide Scanning Microscope at 20× (APERIO®). Images were extracted from the VPM/VPL of the thalamus and layers 2/3 of the somatosensory cortex, with multiple images taken of multiple tissues from each animal. Total area of immunoreactivity was quantified using a threshold analysis in ImageJ.

Figure 18:
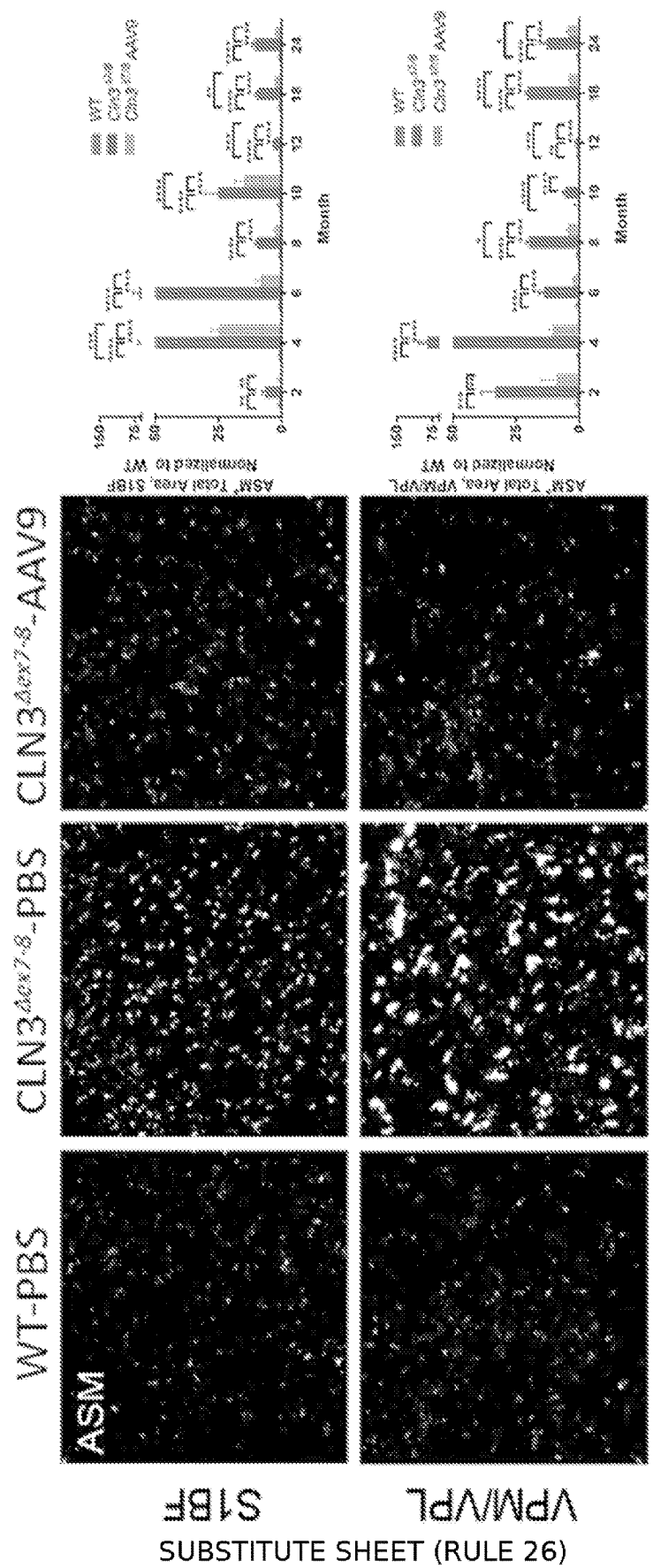
FIG. 18 provides data demonstrating that scAAV9.p546.CLN3 treatment prevented and reduced ASM accumulation in two areas of the brain in Cln3$^{Δ7/8}$ mice up to 24 months of age. Mean±SEM, ordinary one-way ANOVA at each month, $*p<0.05$, $p<0.01$, $*p<0.001$, $****p<0.0001$. Images taken at 20×.
Figure 19:
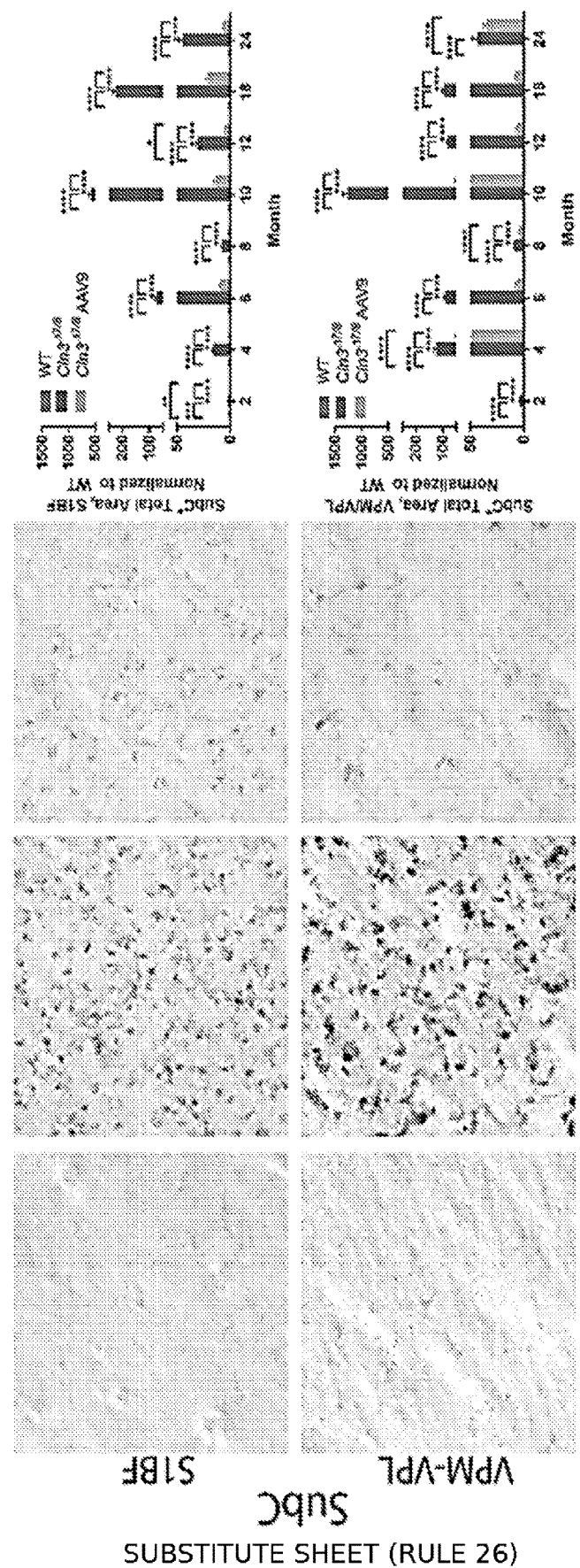
FIG. 19 provides data demonstrating that scAAV9.p546.CLN3 treatment prevented large amounts of SubUnitC accumulation, (a constituent of the ASM) in two areas of the brain of Cln3$^{Δ7/8}$ mice up to 24 months of age. Mean±SEM, ordinary one-way ANOVA at each month, $*p<0.05$, $p<0.01$, $*p<0.001$, $****p<0.0001$. Images taken at 20×.
Figure 20:
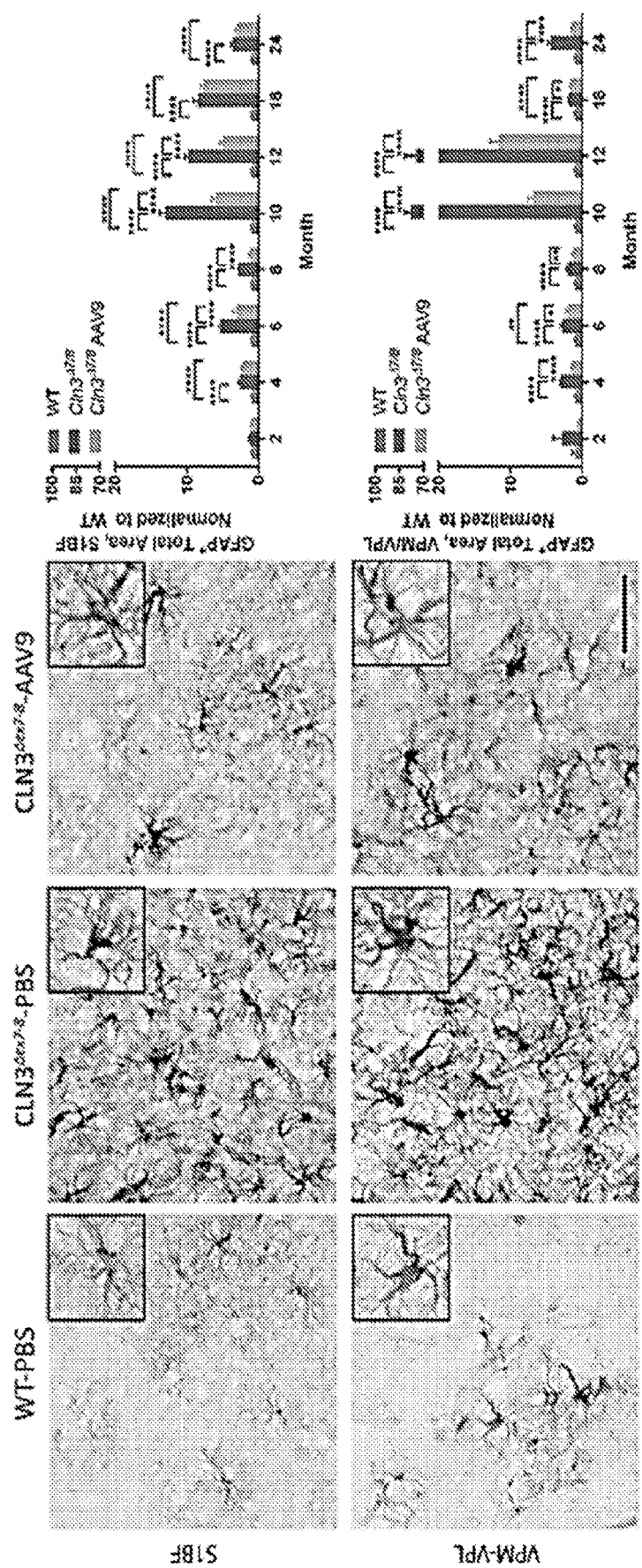
FIG. 20 provides data demonstrating that scAAV9.p546.CLN3 treatment prevented astrocyte activation (GFAP$^+$) in two areas of the Cln3$^{Δ7/8}$ brain up to 24 months of age. Mean±SEM, ordinary one-way ANOVA at each month, $*p<0.05$, $p<0.01$, $*p<0.001$, $****p<0.0001$. Images taken at 20×.
Figure 21:
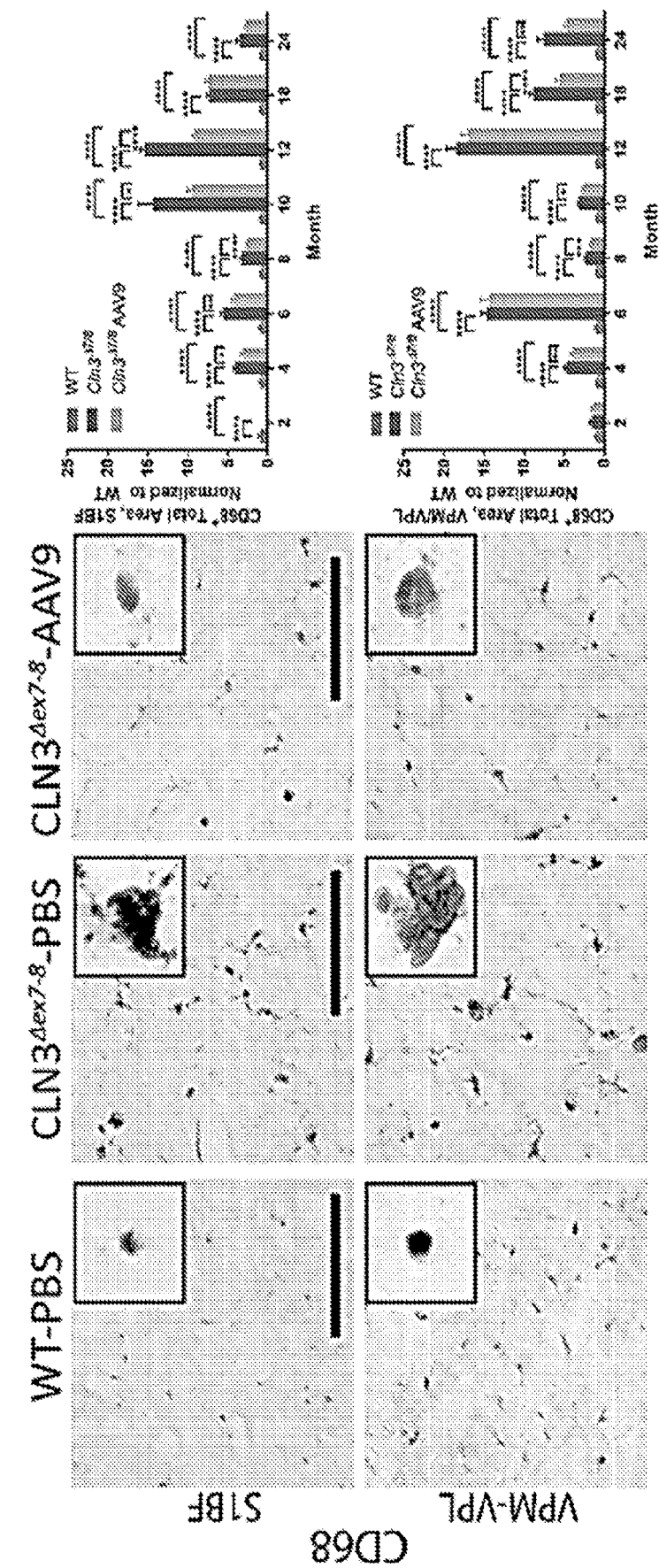
FIG. 21 provides data demonstrating scAAV9.p546.CLN3 treatment prevented some microglial activation (CD68+) in the two areas of the Cln3$^{Δ7/8}$ brain up to 24 months of age, dependent on time point. Mean±SEM, ordinary one-way ANOVA at each month, $*p<0.05$, $p<0.01$, $*p<0.001$, $****p<0.0001$. Images taken at 20×.
Figure 22:
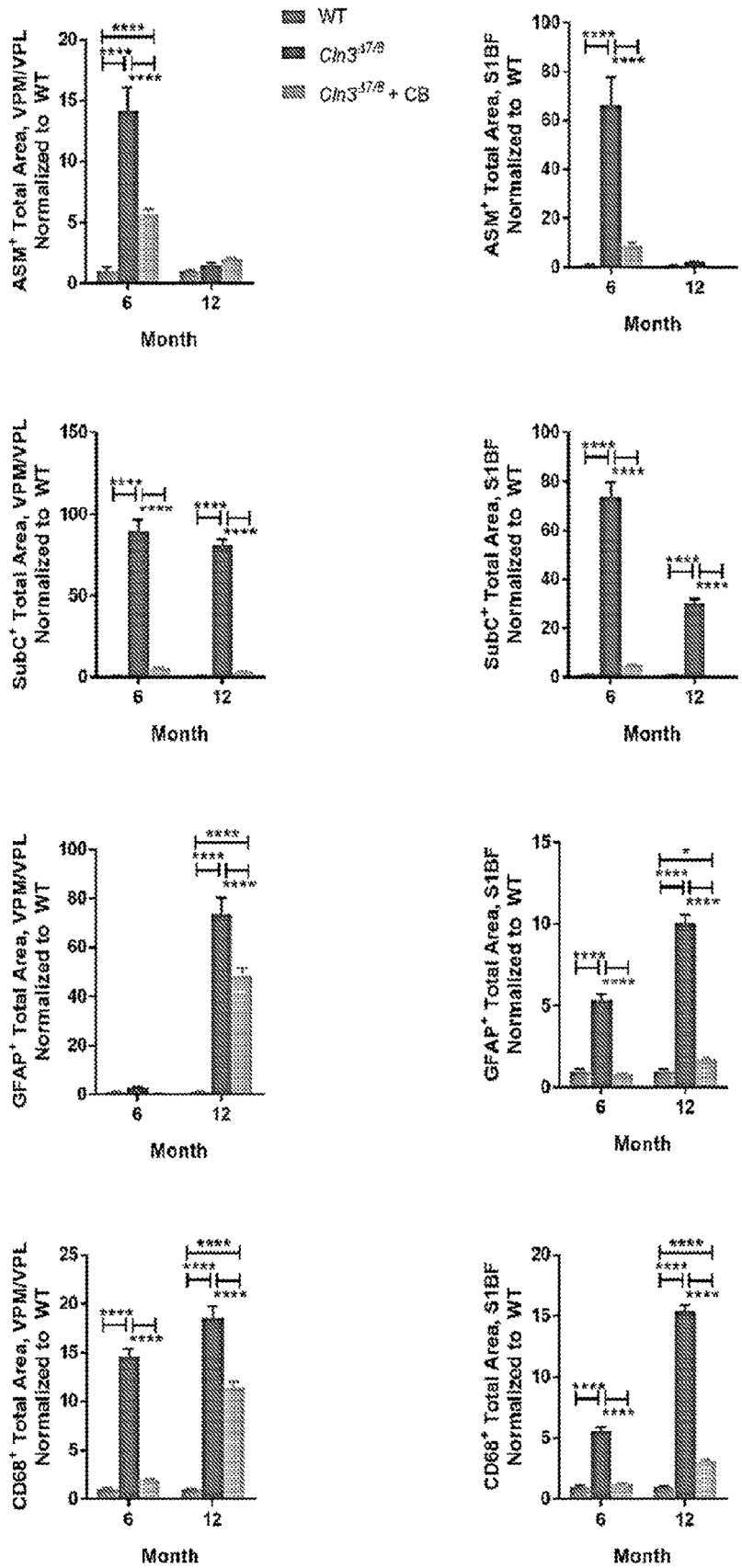
FIG. 22 provides data demonstrating scAAV9.CB.CLN3 treatment is similarly effective in preventing various Batten disease pathologies in 6 and 12 month old Cln3$^{Δ7/8}$ mice. Mean±SEM, ordinary two-way ANOVA, $*p<0.05$, $p<0.01$, $*p<0.001$, $****p<0.0001$.

FIG. 18 demonstrates that scAAV9.p546.CLN3 treatment prevents and reduces ASM accumulation in two areas of the brain in Cln3$^{\Delta 7/8}$ mice up to 24 months of age. FIG. 19 demonstrates that scAAV9.p546.CLN3 treatment generally prevented large amounts of SubUnitC accumulation, (a constituent of the ASM) in two areas of the brain of Cln3$^{\Delta 7/8}$ mice up to 24 months of age. FIG. 20 demonstrates that scAAV9.p546.CLN3 treatment generally prevents astrocyte activation (GFAP+) in two areas of the Cln3Δ7/8 brain up to 24 months of age. FIG. 21 demonstrates that scAAV9.p546.CLN3 treatment prevents some microglial activation (CD68+) in the two areas of the Cln3Δ7/8 brain up to 24 months of age, dependent on time point. Thus, scAAV9.p546.CLN3 prevented classic Batten disease pathologies in the brain of Cln3$^{\Delta 7/8}$ mice, including storage material accumulation and glial reactivity. FIG. 22 demonstrates that scAAV9.CB.CLN3 treatment is similarly effective in preventing various Batten disease pathologies in 6 and 12 month old Cln3$^{\Delta 7/8}$ mice.

Figure 23:
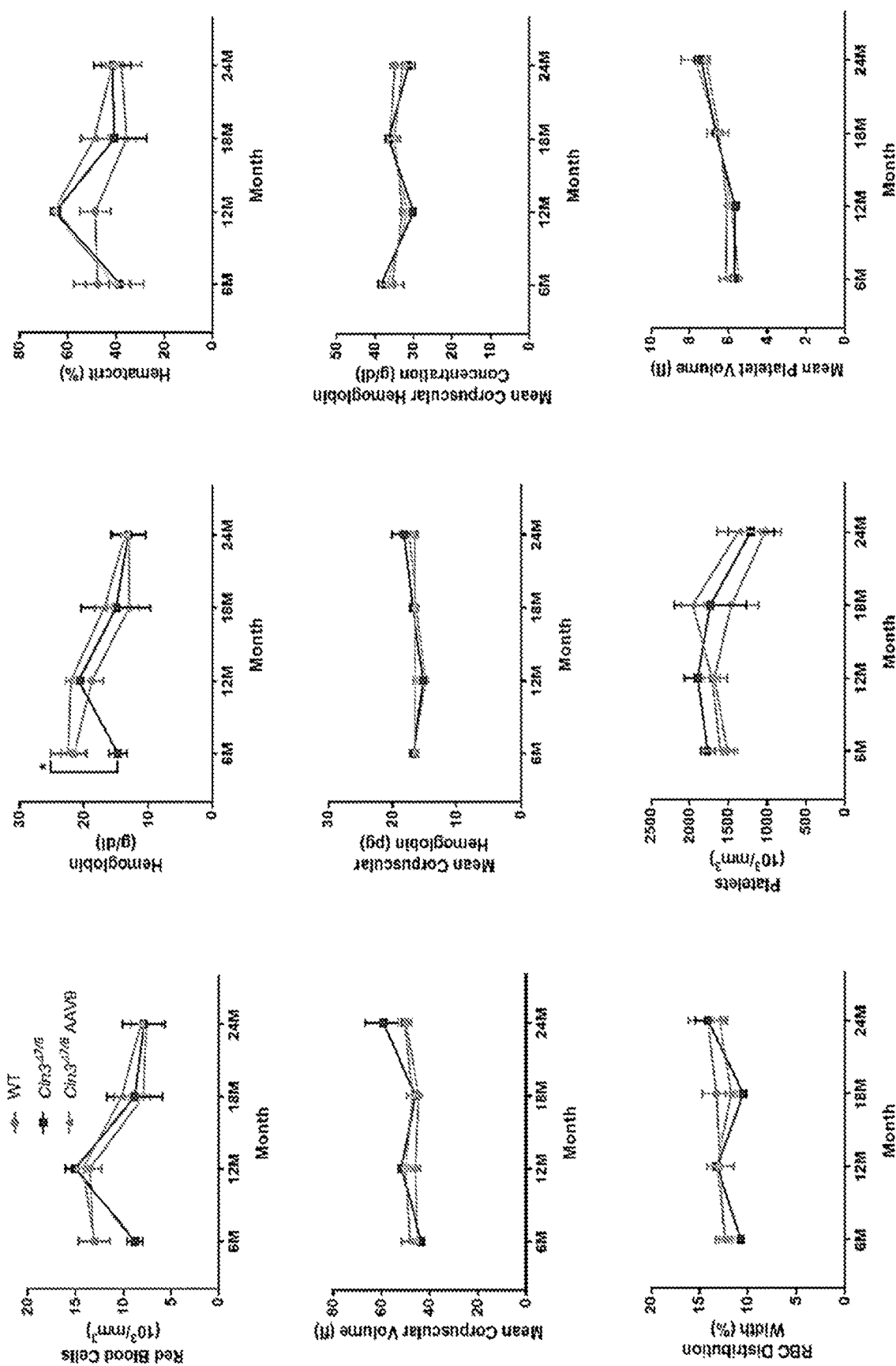
FIG. 23 provides data demonstrating Cln3$^{Δ7/8}$ have no red blood cell abnormalities, as measured up to 24 months of age. Mean±SEM, ordinary two-way ANOVA FIG. 24 provides data Cln3$^{Δ7/8}$ mice have no white blood cell abnormalities, as measured up to 24 months of age. Mean±SEM, ordinary two-way ANOVA FIG. 25 demonstrates scAAV9.p546.CLN3 treated mice show differing levels of SubC accumulation in the CA3 region of the hippocampus based on sex at 12 months of age. Mean±SEM, Ordinary Two-way ANOVA with Tukey's post-hoc test, $*p<0.05$, $p<0.01$, $*p<0.001$, $****p<0.0001$.
Figure 24:
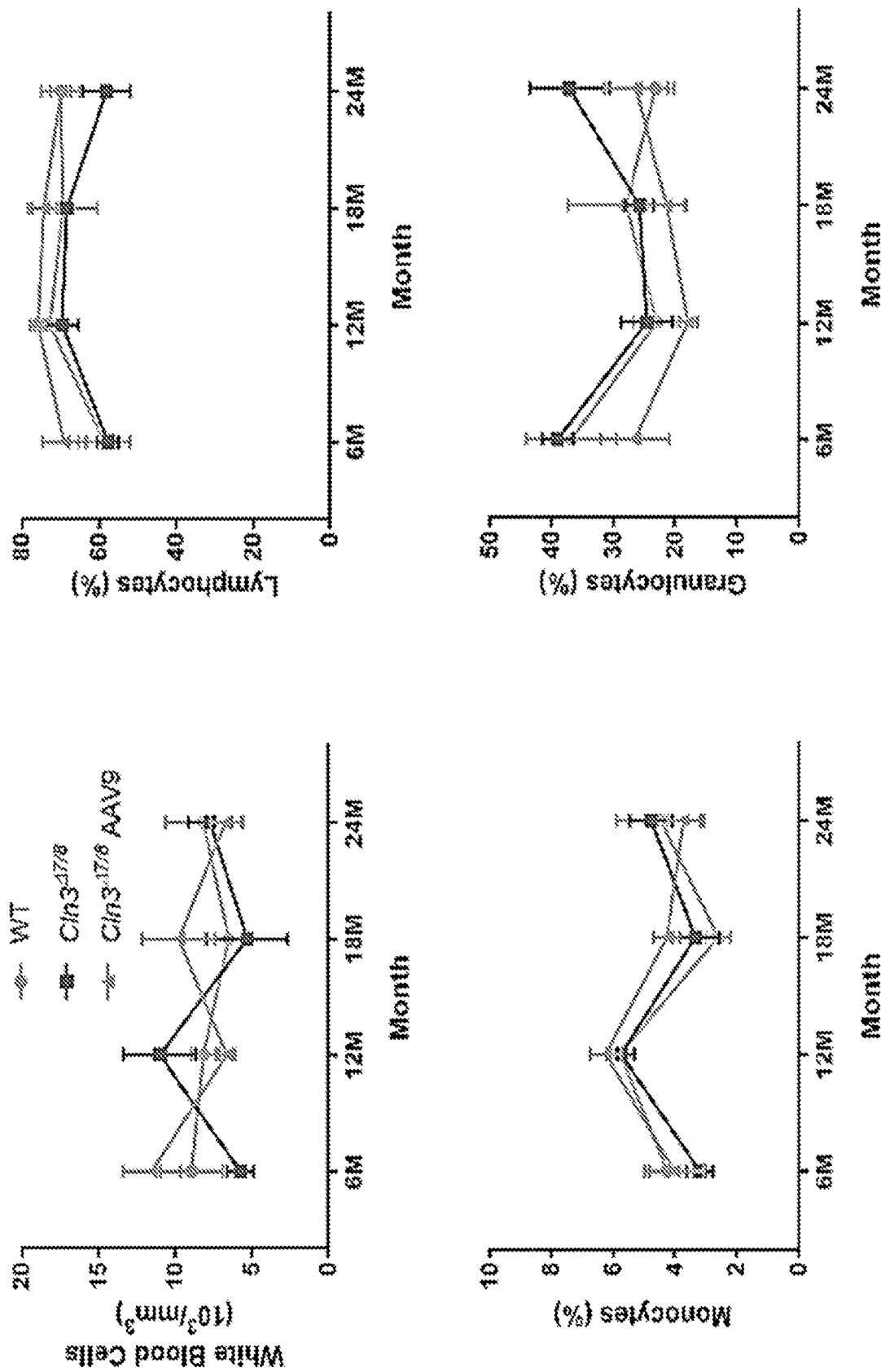

In addition, treatment with scAAV9.p546.CLN3 did not cause any red blood cells (CBC) abnormalities or while blood cell (WBC) abnormalities, as measured up to 24 months post-ICV administration. FIG. 23 provides data for the following CBCs parameters: RBC count, hemoglobin, hematocrit, mean corpuscular volume, mean corpuscular hemoglobin, mean corpuscular hemoglobin concentration, RBC distribution, platelet count and mean platelet volume. FIG. 24 provides data for the following WBCs parameters: WBC count, percent lymphocyte count, percent monocytes, percent granulocytes.

scAAV9.p546.CLN3 gene therapy prevents many of the cellular hallmarks of CLN3-Batten disease up to 24 months of age in Cln3Δ7/8 mice, including ASM, SubUnit C, GFAP and CD68 expression. In addition, scAAV9.CB.CLN3 gene therapy prevents many of the cellular hallmarks of CLN3-Batten disease up to 24 months of age in Cln3$^{\Delta 7/8}$ mice, including ASM, SubUnit C, GFAP and CD68 expression.

Example 7

Sex-Based Histopathology Analysis in Cln3$^{\Delta 7/8}$ Mice Model

As described in Example 2, Wild type (WT) and Cln3Δ7/8 mice were dosed with either PBS, scAAV9.p546.CLN3, or scAAV9.CB.CLN3 gene therapy via intracerebroventricular (ICV) injection at postnatal day 1. In this study, the mice were administered $5\times10^{10}$ vg/animal (4 µL volume).

Wild type and Cln3$^{\Delta 7/8}$ mice were $CO_2$ euthanized, perfused with PBS, and tissue was fixed with 4% PFA. Fixed brains were sectioned on a vibratome at 50 µm (Leica VT10008). Sections were processed with standard immunofluorescence and DAB staining protocols. Primary antibodies included anti-CD68 (AbD Serotec, MCA1957; 1:2000) and anti-ATP synthase subunit C (Abcam, ab181243, 1:1000). Secondary antibodies included anti-rat and anti-rabbit biotinylated (Vector Labs, BA-9400; 1:2000). Sections were imaged and analyzed using an Slide Scanning Microscope at 20× (APERIO®). Images were extracted from the following regions: CA2/CA3 region of the hippocampus, polymorphic layer of the hippocampal dentate gyrus, basolateral amygdala, habenula, reticular nucleus of the thalamus, ventral posterolateral/ventral posteromedial nucleus of the thalamus, mediodorsal and submedial regions of the thalamus, piriform cortex, retrosplenial cortex, and layers 2/3 of the somatosensory cortex, with multiple images taken of multiple tissues from each animal. Total area of immunoreactivity was quantified using a threshold analysis in ImageJ.

Figure 25:
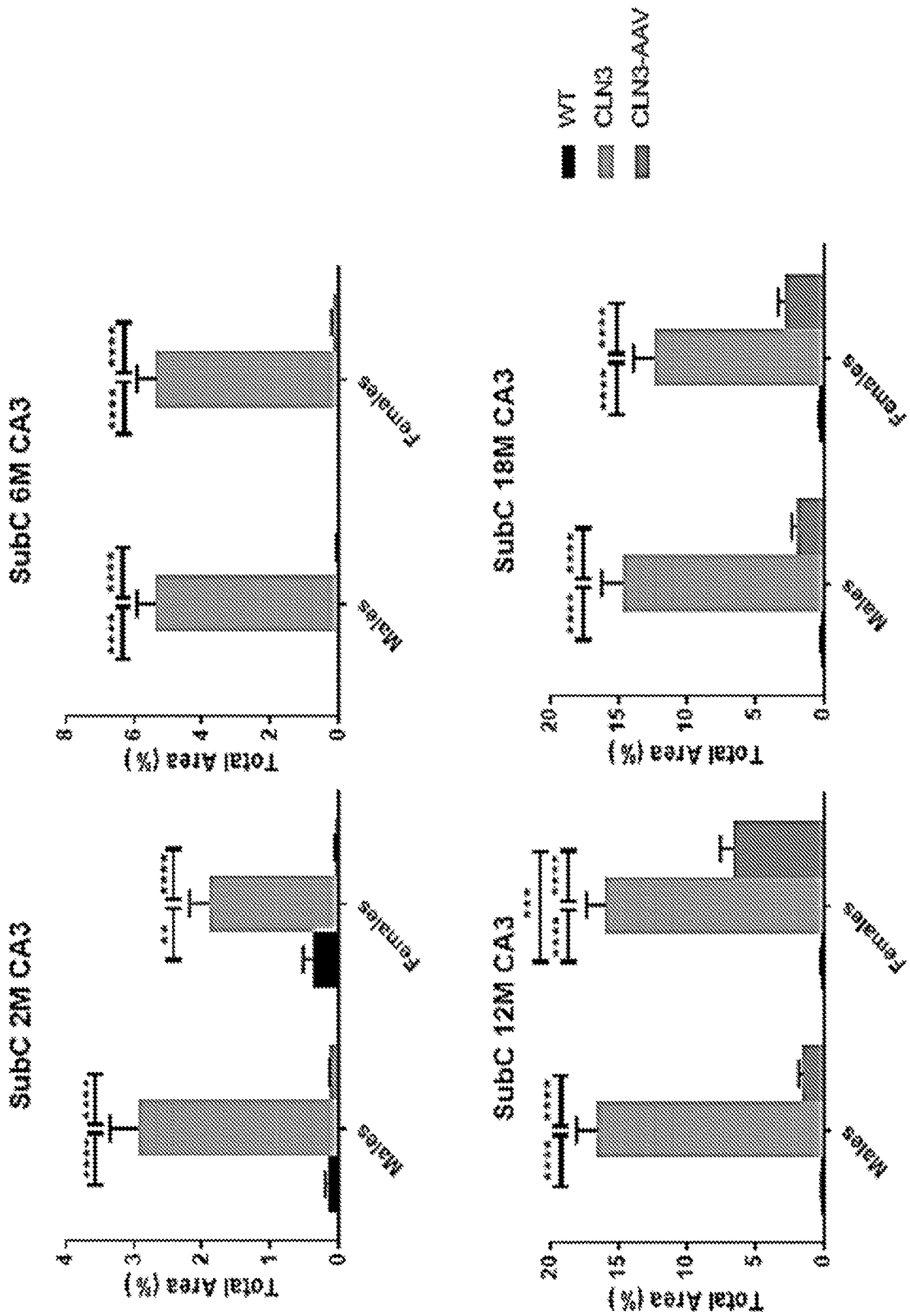

FIG. 25 demonstrates that mice treated with scAAV9.p546.CLN3 show differing levels of SubC accumulation in the CA3 region of the hippocampus based on sex at 12 months of age. At 12 months of age, treated female Cln3° 7/8 mice accumulated significantly more SubC than wild type, while the accumulation of SubC in treated males did not differ from wild type. However, this difference was not seen at any other time point analyzed.

Figure 26:
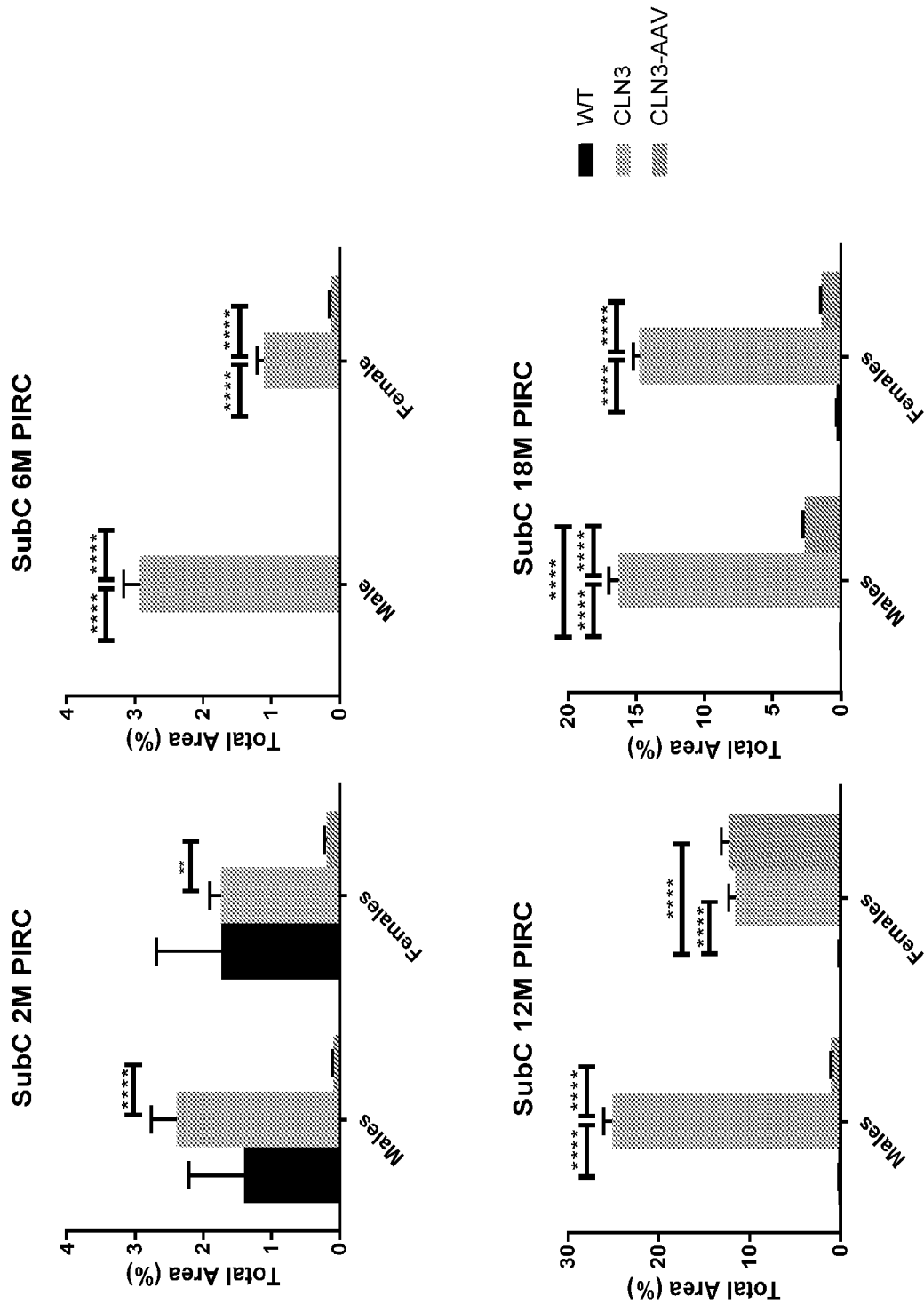
FIG. 26 demonstrates scAAV9.p546.CLN3 mice show subtle, differing levels of SubC accumulation in the Piriform Cortex (PIRC) based on sex at multiple time points. Mean±SEM, Ordinary Two-way ANOVA with Tukey's post-hoc test, $*p<0.05$, $p<0.01$, $*p<0.001$, $****p<0.0001$.

FIG. 26 demonstrates mice treated with scAAV9.p546.CLN3 showed subtle, differing levels of SubC accumulation in the Piriform Cortex (PIRC) based on sex at multiple time points. At 12 months of age, treated female mutant CLN3 mice accumulated significantly more SubC than wild type with AAV treatment not preventing accumulation below PBS mutant levels, while the accumulation of SubC in treated males did not differ from wild type. However, this correlation was not seen at any other time point analyzed and was inconsistent with findings at 18 months of age where SubC accumulation in treated females was not significantly different than wild type and was significantly lower than untreated mutant mice. At 18 months of age, accumulation of SubC in treated males becomes significantly higher than WT levels.

Figure 27:
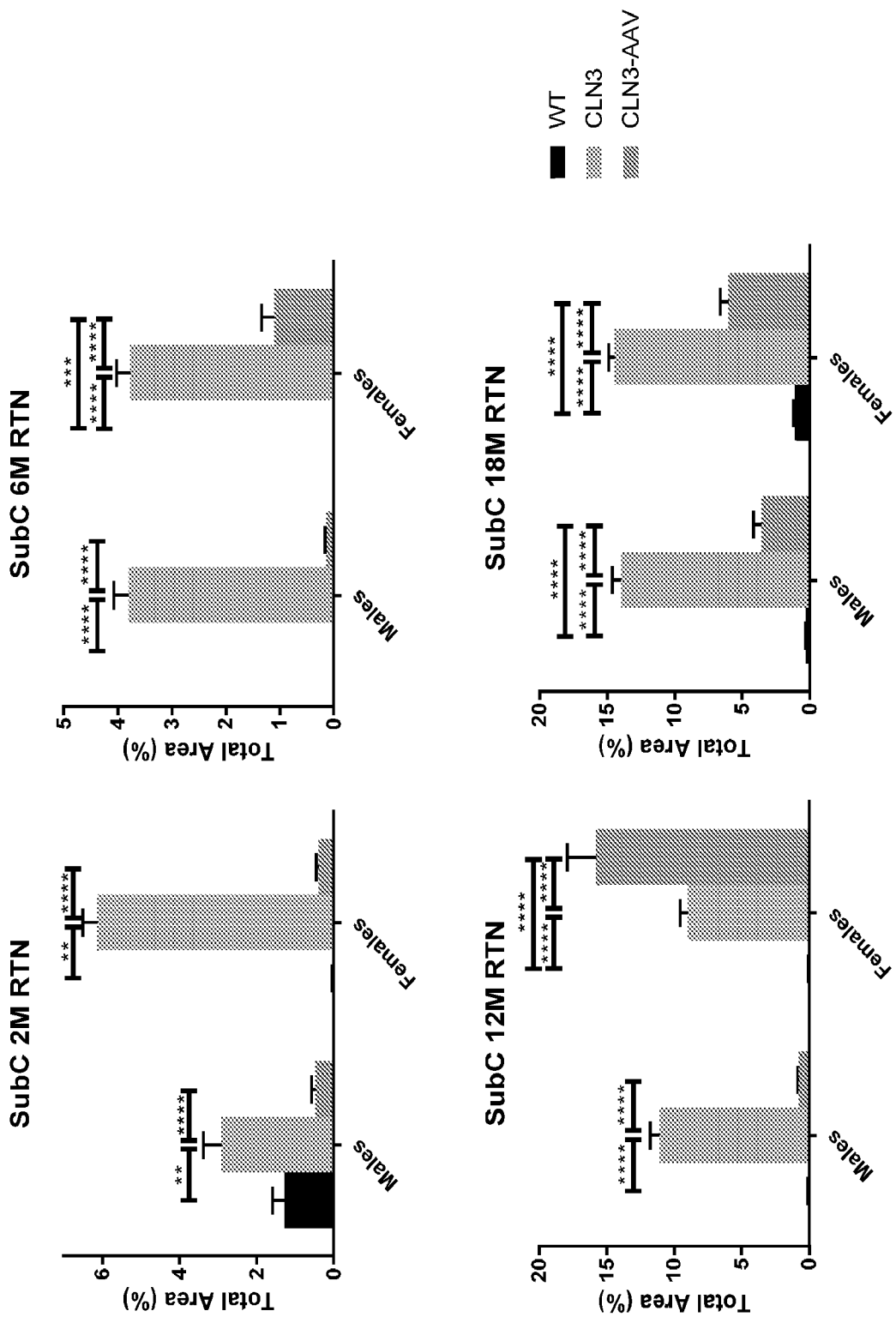
FIG. 27 demonstrates scAAV9.p546.CLN3 mice show differing levels of SubC accumulation in the Reticular Thalamic Nucleus (RTN) based on sex at multiple time points. Mean±SEM, Ordinary Two-way ANOVA with Tukey's post-hoc test, $*p<0.05$, $p<0.01$, $*p<0.001$, $****p<0.0001$.

FIG. 27 demonstrates scAAV9.p546.CLN3 treated mice showed differing levels of SubC accumulation in the Reticular Thalamic Nucleus (RTN) based on sex at multiple time points. At 6 months of age, treated female mutant CLN3 mice accumulated significantly more SubC than wild type, while the accumulation of SubC in treated males does not differ from wild type. At 12 months of age, treated males remained at wild type levels, while treated females have significantly more SubC than both wild type and untreated mutant mice. This difference between female treated and untreated mutants was not present at 18 months, where SubC was significantly higher than WT but significantly lower than untreated mutants in both males and females.

Figure 28:
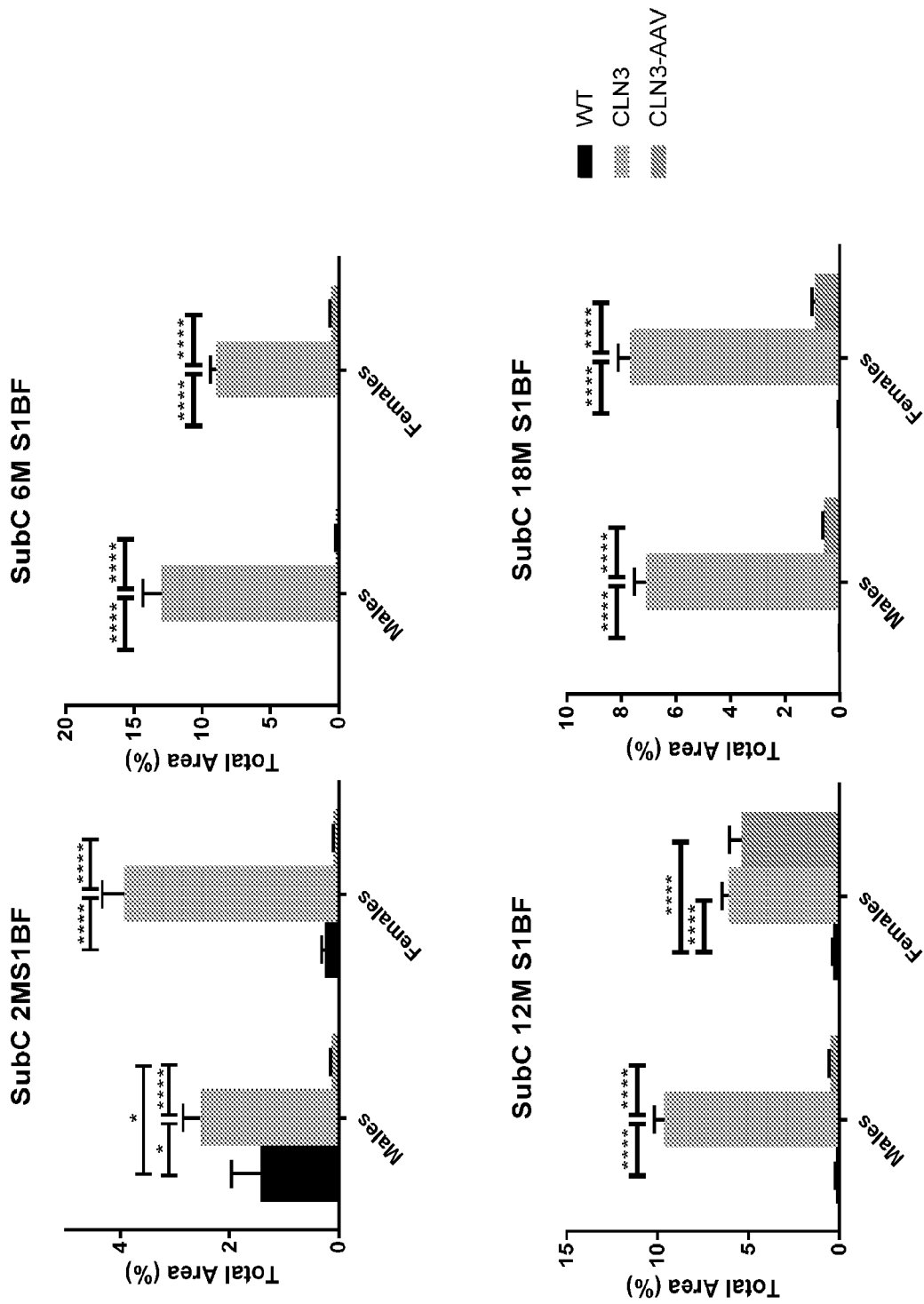
FIG. 28 demonstrates scAAV9.p546.CLN3 mice show differing levels of SubC accumulation in the Somatosensory Cortex based on sex at 12 months. Mean±SEM, Ordinary Two-way ANOVA with Tukey's post-hoc test, $*p<0.05$, $p<0.01$, $*p<0.001$, $****p<0.0001$.

FIG. 28 demonstrates that scAAV9.p546.CLN3 treated mice show differing levels of SubC accumulation in the Somatosensory Cortex based on sex at 12 months. At 12 months of age, treatment with AAV did not reduce SubC accumulation compared to untreated mutant females, while accumulation of SubC in treated males was prevented and did not differ from wild type. However, this difference was not seen at any other time point analyzed.

Figure 29:
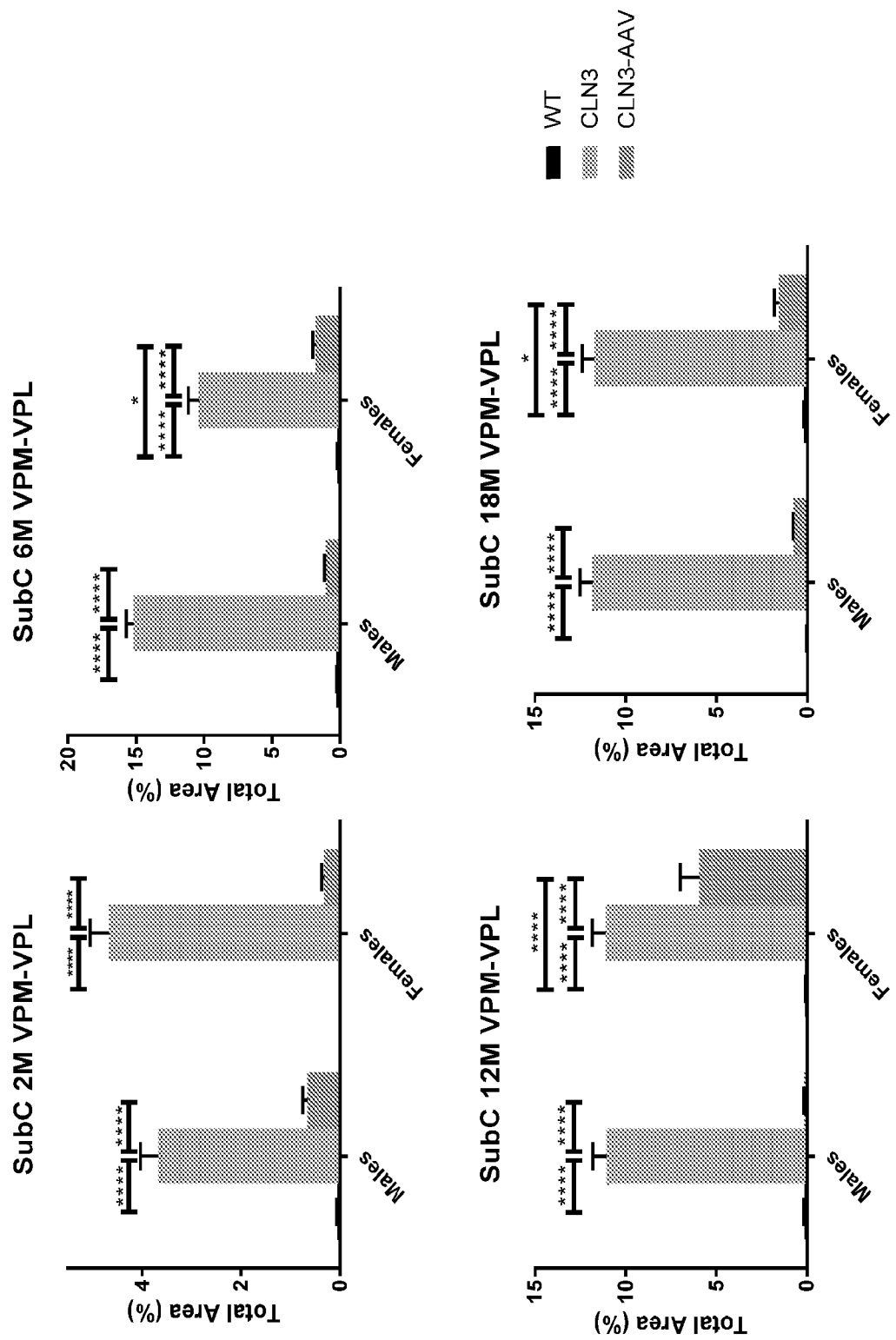
FIG. 29 demonstrates scAAV9.p546.CLN3 mice show differing levels of SubC accumulation in the VPM/VPL of the thalamus based on sex at 12 months. Mean±SEM, Ordinary Two-way ANOVA with Tukey's post-hoc test, $*p<0.05$, $p<0.01$, $*p<0.001$, $****p<0.0001$.

FIG. 29 demonstrates mice treated with scAAV9.p546.CLN3 showed differing levels of SubC accumulation in the VPM/VPL of the thalamus based on sex at 12 months. At 6 months of age, treated females accumulated significantly less SubC than untreated mutant females, but significantly more than wild type females. This difference continued through 12 and 18 months, with no differences between wild type and treated males at any time point analyzed.

Figure 30:
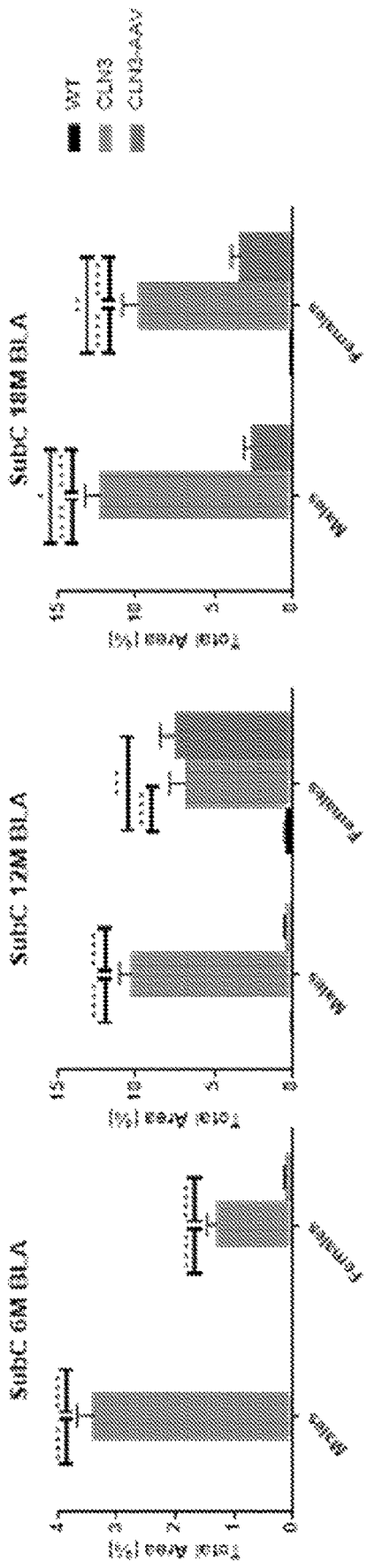
FIG. 30 demonstrates scAAV9.p546.CLN3 mice show differing levels of SubC accumulation in the Basolateral Amygdala (BLA) based on sex at 12 months. Mean±SEM, Ordinary Two-way ANOVA with Tukey's post-hoc test, $*p<0.05$, $p<0.01$, $*p<0.001$, $****p<0.0001$.

FIG. 30 demonstrates mice treated with scAAV9.p546.CLN3 show differing levels of SubC accumulation in the Basolateral Amygdala (BLA) based on sex at 12 months. At 12 months of age, AAV did not significantly prevent accumulation of SubC in treated female animals. At 18 months, SubC accumulation in treated females remained significantly higher than wild type, but was lower than untreated females. By 18 months treated males also begin to have significantly more SubC than their wild type counterpart, mimicking what was seen in female groups.

Figure 31:
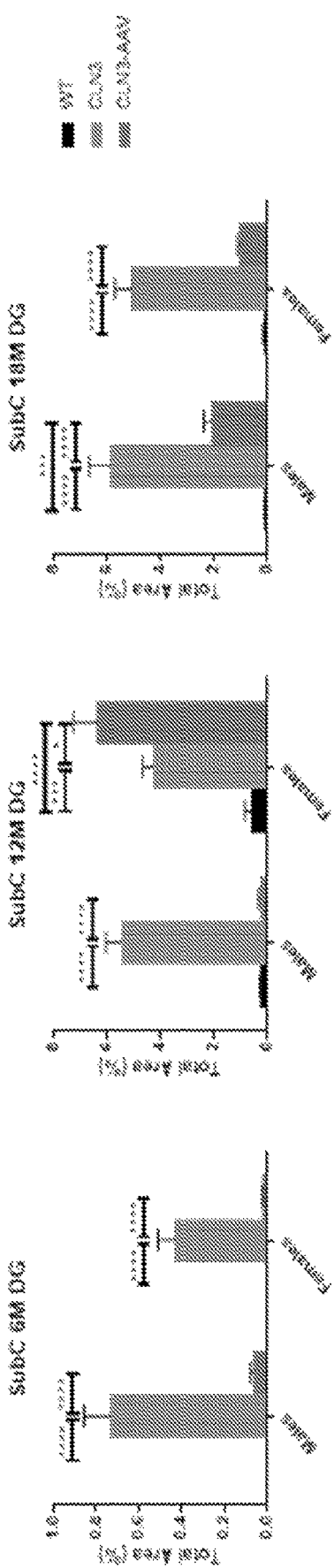
FIG. 31 provides scAAV9.p546.CLN3 mice show differing levels of SubC accumulation in the Polymorphic Layer of the Dentate Gyrus (DG) based on sex at 12 and 18 months. Mean±SEM, Ordinary Two-way ANOVA with Tukey's post-hoc test, $*p<0.05$, $p<0.01$, $*p<0.001$, $****p<0.0001$.

FIG. 31 demonstrates scAAV9.p546.CLN3 treated mice showed differing levels of SubC accumulation in the Polymorphic Layer of the Dentate Gyrus (DG)based on sex at 12 and 18 months. At 12 months of age, treated females appeared to have accumulated significantly more SubC than both wild type females and untreated mutant females. Raw images (not shown) revealed a darkened granule cell layer surrounding the polymorphic layer of the dentate gyrus that may impact the thresholding results. This darkening was present only in this group and only at the 12 month time point. This increase was also no longer seen at 18 months in females, however, at 18 months treated males began to have more SubC accumulation than wild type males.

Figure 32:
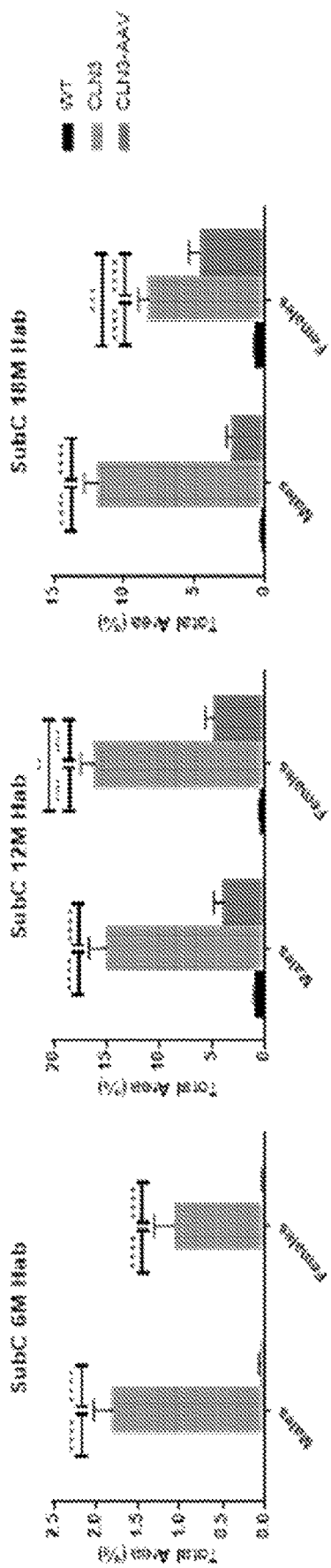
FIG. 32 demonstrates scAAV9.p546.CLN3 mice show differing levels of SubC accumulation in the Habenula (Hab) based on sex at 12 and 18 months. Mean±SEM, Ordinary Two-way ANOVA with Tukey's post-hoc test, $*p<0.05$, $p<0.01$, $*p<0.001$, $****p<0.0001$.

FIG. 32 demonstrates scAAV9.p546.CLN3 treated mice show differing levels of SubC accumulation in the Habenula based on sex at 12 and 18 months. At 12 months of age, treated females accumulated significantly less SubC than untreated mutant females, but significantly more than wild type females. This difference was also seen at 18 months, with no differences between wild type and treated males at any time point analyzed.

Figure 33:
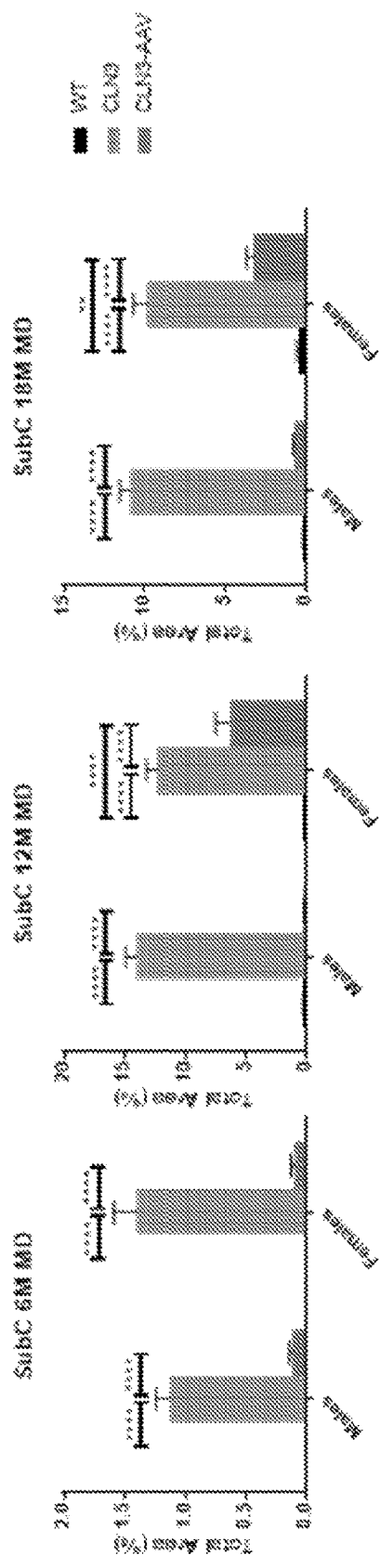
FIG. 33 provides data demonstrating scAAV9.p546.CLN3 mice show differing levels of SubC accumulation in the Mediodorsal Nucleus (MD) based on sex at 12 and 18 months. Mean±SEM, Ordinary Two-way ANOVA with Tukey's post-hoc test, $*p<0.05$, $p<0.01$, $*p<0.001$, $****p<0.0001$.

FIG. 33 demonstrates mice treated with scAAV9.p546.CLN3 showed differing levels of SubC accumulation in the Mediodorsal Nucleus based on sex at 12 and 18 months. At 12 months of age, treated females accumulated significantly less SubC than untreated mutant females, but significantly more than wild type females. This difference was also seen at 18 months, with no differences between wild type and treated males at any time point analyzed.

Figure 34:
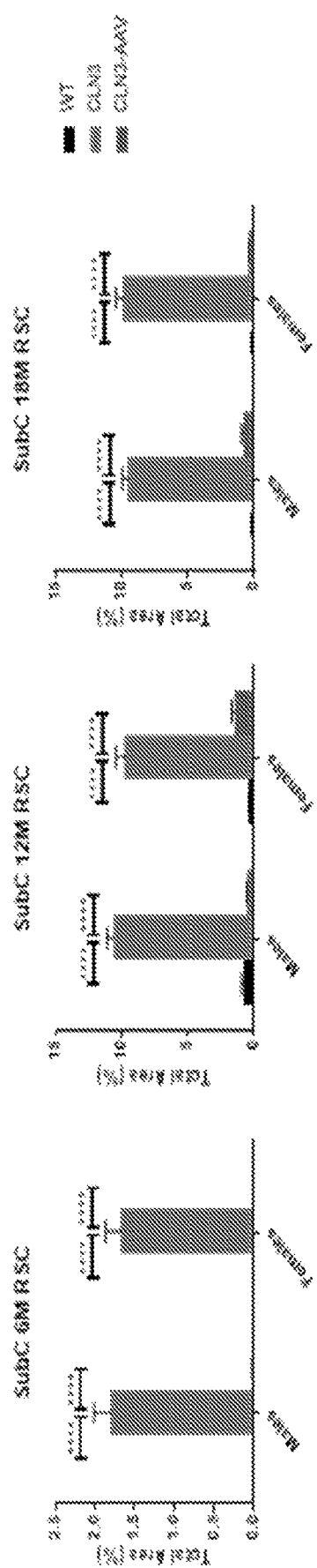
FIG. 34 demonstrates that scAAV9.p546.CLN3 mice show no difference in levels of SubC accumulation in the Retrosplenial Cortex (RSC) based on sex. Mean±SEM, Ordinary Two-way ANOVA with Tukey's post-hoc test, $*p<0.05$, $p<0.01$, $*p<0.001$, $****p<0.0001$.

FIG. 34 demonstrates mice treated with scAAV9.p546.CLN3 showed no difference in levels of SubC accumulation in the Retrosplenial Cortex (RSC) based on sex. There were no differences between wild type and treated males at any time point analyzed.

Figure 35:
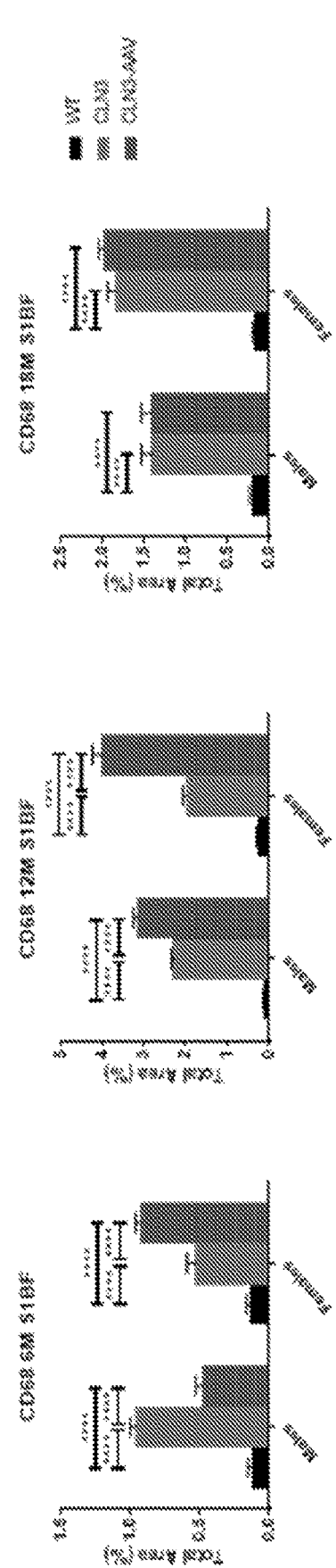
FIG. 35 demonstrates that scAAV9.p546.CLN3 mice show differing levels of activated microglia (CD68+) in the Somatosensory Cortex (S1BF) based on sex at 6 months. Mean±SEM, Ordinary Two-way ANOVA with Tukey's post-hoc test, $*p<0.05$, $p<0.01$, $*p<0.001$, $****p<0.0001$.

FIG. 35 demonstrates mice treated with scAAV9.p546.CLN3 showed differing levels of activated microglia (CD68$^+$) in the Somatosensory Cortex (S1BF) based on sex at 6 months. At 6 months of age, treated females had increased microglial activation compared to wild type and untreated females, with treated males higher than wild type but lower than untreated. No sex differences were seen at 12 and 18 months of age.

FIG. 36 demonstrates mice treated with scAAV9.p546.CLN3 show differing levels of microglia activation in the VPM-VPL, thalamus based on sex. At 6 months of age, treated females have increased microglial activation compared to wild type and untreated females, with treated males higher than wild type but lower than untreated. This difference is also seen at 12 months. The same is seen in female groups at 18 months, however, treated males did not significantly differ from wild type at this time point.

FIG. 37 demonstrates scAAV9.p546.CLN3 mice show differing levels of activated microglia (CD68+) in the Mediodorsal Nucleus (MD) based on sex. At 6 months of age, treated females had increased microglial activation compared to wild type and untreated females, with treated males higher than wild type but not different than untreated males. At both 12 and 18 months of age, treated males had higher microglial activation than wild type and lower activation than untreated males, while treatment appeared to have no effect on females.

FIG. 38 demonstrates mice treated with scAAV9.p546.CLN3 showed differing levels of activated microglia in the Submedial Nucleus (SM) based on sex. At 6 months of age, treated females had increased microglial activation compared to wild type and untreated females, while treated males were not significantly different from untreated males, both having more activation than wild type. By 12 months, treatment appeared to not have an impact on degree of microglial activation in either sex. By 18 months, treated males have microglial activation reduced to wild type levels, while treated females remained activated to the same extent as untreated females.

The foregoing data demonstrates that scAAV9.p546.CLN3 treated animals have differential sex-based pathology related to ATP-Synthase Subunit C accumulation and CD68$^+$ microglial activation in several regions of the Cln3$^{\Delta 7/8}$ mouse brain. Differential sex-based pathological differences appear to be more female specific. The 12 month time point is where a majority of differences are most consistently seen, with many appearing only at 12 months and no longer present by 18 months.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby. All documents referred to in this application are hereby incorporated by reference in their entirety.

What is claimed is:

1. A nucleic acid molecule comprising at least 90% sequence similarity to the nucleic acid sequence of SEQ ID NO: 4.

2. The nucleic acid molecule of claim 1, wherein the AAV inverted terminal repeats are AAV2 inverted terminal repeats.

3. A self-complementary recombinant adeno-associated virus 9 (scAAV9) comprising a nucleic acid molecule of claim 1.

4. The scAAV9 of claim 3, wherein the scAAV9 comprises a single-stranded genome.

5. An rAAV9 particle comprising a nucleic acid molecule of claim 1.

6. The rAAV particle of claim 5, wherein the rAAV particle comprises a single-stranded genome.

7. A method of treating CLN3-Batten Disease in a subject comprising administering to the subject a composition comprising a therapeutically effective amount of the rAAV9 particle of claim 5.

8. The method of claim 7, wherein the composition is administered via a route selected from the group consisting of intrathecal, intracerebroventricular, intraparenchymal, intravenous, and a combination thereof.

9. The method of claim 7, wherein the composition is administered intrathecally.

10. The method of claim 7, wherein the composition is administered intracerebroventricularly.

11. The method of claim 7, wherein the composition is administered intravenously.

12. The method of claim 7, wherein $1 \times 10^{12}$ to $1 \times 10^{15}$ vg of the rAAV9 viral particle is administered.

13. The method of claim 7, wherein $6 \times 10^{13}$ to $1.2 \times 10^{14}$ of the rAAV9 viral particle is administered.

14. The method of claim 7, further comprising a step of measuring one or more symptoms of CLN3-Batten Disease, wherein the treatment reduces or slows one or more symptoms of CLN3-Batten Disease, wherein the symptom comprises:
(a) lysosomal accumulation of autofluorescent storage material,
(b) lysosomal accumulation of ATP Synthase Subunit C,
(c) glial activation (astrocytes and/or microglia) activation,
(d) astrocytosis,
(e) brain volume loss measured by magnetic resonance imaging (MRI),
(f) onset of seizures, or
(g) one or more symptom of the Unified Batten Disease Rating Scale (UBDRS),
wherein the symptom is as compared to the subject prior to administering the composition or to an untreated CLN3-Batten Disease patient.

15. The method of claim 7, further comprising placing the subject in the Trendelenburq position after administering the rAAV9 viral particle.

16. A method of treating a CLN3 disease in a subject in need thereof comprising, delivering a composition comprising the rAAV9 viral particle of claim 5 to a brain or spinal cord of a subject in need thereof.

17. The method of claim 16, wherein the composition is delivered by intrathecal injection, intracerebroventricular injection, intraparenchymal injection, intravenous injection, or a combination thereof.

18. The method of claim 17, further comprising placing the subject in the Trendelenburq position after intrathecal injection of the composition.

19. The method of claim 16, wherein the composition comprises a non-ionic low-osmolar contrast agent.

20. The method of claim 19, wherein the non-ionic, low-osmolar contrast agent is selected from the group consisting of iobitridol, iohexol, iomeprol, iopamidol, iopentol, iopromide, ioversol, ioxilan, and combinations thereof.

21. The method of claim 16, wherein delivering to the brain or spinal cord comprises delivery to a brain stem.

22. The method of claim 16, wherein delivering to the brain or spinal cord comprises delivery to a cerebellum.

23. The method of claim 16, wherein delivering to the brain or spinal cord comprises delivery to a) a visual cortex, b) a motor cortex, c) a nerve cell or glial cell or both, d) a neuron, a lower motor neuron, a microglial cell, an oligodendrocyte, an astrocyte, a Schwann cell, or a combination thereof.

24. The method of claim 16 further comprising a step of measuring one or more symptoms of CLN3-Batten Disease, wherein the treatment reduces or slows one or more symptoms of CLN3-Batten Disease, wherein the symptom comprises:
   (a) lysosomal accumulation of autofluorescent storage material,
   (b) lysosomal accumulation of ATP Synthase Subunit C,
   (c) glial activation (astrocytes and/or microglia) activation,
   (d) astrocytosis,
   (e) brain volume loss as measured by magnetic resonance imaging (MRI),
   (f) onset of seizures, and
   (g) one or more symptom of the Unified Batten Disease Rating Scale (UBDRS),
      wherein the symptom is as compared to the subject prior to delivering the composition or to an untreated CLN3-Batten Disease patient.

25. A composition comprising the nucleic acid molecule of claim 1 and a pharmaceutically acceptable excipient, carrier, or diluent.

26. The composition of claim 25, wherein the excipient comprises a non-ionic low osmolar compound, a buffer, a polymer, a salt, or a combination thereof.

* * * * *